US008268828B2

(12) United States Patent
Thorpe et al.

(10) Patent No.: US 8,268,828 B2
(45) Date of Patent: Sep. 18, 2012

(54) INHIBITORS OF THE CHEMOKINE RECEPTOR CXCR3

(75) Inventors: David Squire Thorpe, Tucson, AZ (US); Martin Smrcina, Tucson, AZ (US); Dagmar Dasha Cabel, Tucson, AZ (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 12/852,076

(22) Filed: Aug. 6, 2010

(65) Prior Publication Data
US 2010/0305088 A1    Dec. 2, 2010

Related U.S. Application Data

(63) Continuation of application No. PCT/US2009/034340, filed on Feb. 18, 2009.

(60) Provisional application No. 61/029,738, filed on Feb. 19, 2008.

(51) Int. Cl.
| | |
|---|---|
| *A61K 31/495* | (2006.01) |
| *A61K 31/496* | (2006.01) |
| *C07D 295/185* | (2006.01) |
| *C07D 295/033* | (2006.01) |
| *A61K 31/48* | (2006.01) |
| *C07D 471/10* | (2006.01) |

(52) U.S. Cl. ......... 514/252.13; 514/253.01; 514/254.01; 514/254.09; 514/255.01; 544/360; 544/372; 544/373; 544/379; 544/391; 546/16; 546/225

(58) Field of Classification Search .......................... None
See application file for complete search history.

(56) References Cited

U.S. PATENT DOCUMENTS

| | | | |
|---|---|---|---|
| 3,719,660 | A | 3/1973 | Imai et al. |
| 3,840,556 | A | 10/1974 | Kujolja et al. |
| 6,124,319 | A | 9/2000 | MacCoss et al. |
| 7,067,662 | B2 | 6/2006 | Medina et al. |
| 2007/0021611 | A1 | 1/2007 | McGuinness et al. |
| 2007/0054919 | A1 | 3/2007 | Rosenblum et al. |
| 2007/0082913 | A1 | 4/2007 | Kim et al. |

FOREIGN PATENT DOCUMENTS

| | | |
|---|---|---|
| WO | WO 02/085861 A1 | 10/2002 |
| WO | WO 03/070242 A1 | 8/2003 |
| WO | WO 03/101970 A1 | 12/2003 |
| WO | WO 2006/088840 A1 | 8/2006 |
| WO | 2007/002742 * | 1/2007 |
| WO | WO 2007/002742 A1 | 1/2007 |
| WO | WO 2007/064553 A2 | 6/2007 |
| WO | WO 2007/109238 A1 | 9/2007 |
| WO | WO 2008/008453 A1 | 1/2008 |
| WO | WO 2009/105435 A1 | 8/2009 |

OTHER PUBLICATIONS

Burger's Medicinal Chemistry, edited by Manfred E. Wolff, 5th Ed. Part 1, pp. 975-977 (1995).*
Banker et al. "Modern Pharmaceutics", 3rd Ed. p. 596 (1996).*
Vippagunta et al Advanced Drug Delivery Reviews, vol. 48, pp. 3-26 (2001).*
Yang, et al., A Non-Peptide CCR5 Antagonist Inhibits Collagen-Induced Arthritis by Modulating T Cell Migration Without Affecting Anti-Collagen T Cell Responses, Eur. J. Immunol., (2002), vol. 32, pp. 2124-2132.
Allen, et al., Identification and Structure-Activity Relationships of 1-aryl-3-Piperidin-4-yl-Urea Derivatives as CXCR3 Receptor Antagonists, Bioorganic & Medicinal Chemistry Letters, vol. 17. (2007), pp. 697-701.
Annunziato, et al., Chemokine Receptors and Other Surface Molecules Preferentially Associated With Human Th1 or Th2 Cells, Microbes and Infection, vol. 1, (1999), pp. 103-106.
Berge, et al., Pharmaceutical Salts, J. Pharmaceutical Sciences. (1977), vol. 66, No. 1, pp. 1-19.
Bundgaard, et. al., (C) Means to Enhance Penetration, Advanced Drug Delivery Reviews, vol. 8, (1992), pp. 1-38.
Chensue, Molecular Machinations: Chemokine Signals in Host-Pathogen Interactions. Clin. Microbiol. Rev., (2001), vol. 14, No. 4, pp. 821-835.
Cole, et al., Identification and Initial Evaluation of 4-N-aryl-[1,4]Diazepane Ureas as Potent CXCR3 Antagonists, Bioorganic & Medicinal Chemistry Letters, vol. 16, (2006), pp. 200-203.
Fernandez, et al., Solid-Phase Versus Solution Synthesis of Asymmetrically, Disubstituted Furazano[3,4-b]Pyrazines, Tetrahedron Letters, vol. 43, pp. 4741-4745, (2002).
Gao, et al., The Unique Target Specificity of a Nonpeptide Chemokine Receptor Antagonist: Selective Blockade of Two Th1 Chemokine Receptors CCR5 and CXCR3, Journal of Leukocyte Biology, vol. 73, (2003), 273-280.
Houshmand, et al., Therapeutic Applications in the Chemokine Superfamily, Current Opinion in Chemical Biology, vol. 7, pp. 457-460. (2003).
Kakeya, et al., Studies on Prodrugs of Cephalosporins. I. Synthesis and Biological Properties of Glycyloxybenzoyloxymethyl and Glycyiaminobenzoyloxymethyl Esters of 7B-[2-(2-Aminothiaxol-4-yl)-(Z)-2-Methoxyiminoacetamido]-3-Methyl-3-Cephem-4-Carboxylic Acid, Chem. Pharm. Bull., vol. 32, No. 2, pp. 692-698, (1984).
Lasagni, et al., An Alternatively Spliced Variant of CXCR3 Mediates The Inhibition of Endothelial Cell Growth Induced by IP-10, Mig. and I-TAC, and Acts as Functional Receptor for Platelet Factor 4, J. Exp. Med., vol. 197, No. 11, (2003), pp. 1537-1549.
Loetscher, et al., The Ligands of CXC Chemokine Receptor 3, I-TAC, Mig, and IP10, Are Natural Antagonists for CCR3, The Journal of Biological Chemistry, vol. 276, No. 5, pp. 2986-2991, (2001).
Nielsen, et al., Glycolamide Esters as Biolabile Prodrugs of Carboxylic Acid Agents: Synthesis, Stability, Bioconversion, and Physioochemical Properties, Journal of Pharmaceutical Sciences, vol. 77, No. 4, (1988), pp. 285-298.
Patel, et al., CXR3 and CCR5 Ligands in Rheumatoid Arthritis Synovium, Clinical Immunology, vol. 98, No. 1, pp. 39-45, (2001).
Pease, et al., The Attraction of Chemokines as a Target for Specific Anti-Inflammatory Therapy, British Journal of Pharmacology, vol. 147, (2006), S212-S221.

(Continued)

*Primary Examiner* — Emily Bernhardt
(74) *Attorney, Agent, or Firm* — Ronald G. Ort; Barbara E. Kurys

(57) ABSTRACT

This invention is directed to a 3-(amido or sulphamido)-4-(4-substituted-azinyl)benzamide or benzsulphonamide compound as defined herein. The 3-(amido or sulphamido)-(4-substituted-azinyl)benzamide or benzsulphonamide compound is useful as a inhibitor of the chemokine receptor CxCR3, and for preventing or treating a CxCR3 chemokine receptor mediated disease or condition related thereto in a patient in need of such.

2 Claims, No Drawings

OTHER PUBLICATIONS

Proudfoot, Chemokine Receptors: Multifaceted Therapeutic Targets, Nature Reviews Immunol., vol. 2, (2002), pp. 106-115.

Singh, et al., Inhibition of IFN-Y-Inducible Protein-10 Abrogates Colitis in IL-10 -/- Mice, J. Immunol., (2003), vol. 171, pp. 1401-1406.

Veillard, et al, Differential Influence of Chemokine Receptors CCR2 and CXCR3 in Development of Atherosclerosis In Vivo, Circulation, (2005), vol. 112, pp. 870-878.

Walser, et al., Antagonism of CXCR3 Inhibits Lung Metastasis in a Murine Model of Metastatic Breast Cancer, Cancer Research, vol. 66, pp. 7701-7707, (2006).

Weber, et al., Systematic Optimization of a Lead-Structure Identities for a Selective Short Peptide Agonist for the Human Orphan Receptor BRS-3, Journal of Peptide Science, vol. 8, pp. 461-475, (2002).

Westermann, et al., Migration of T Cells In Vivo: Molecular Mechanisms and Clinical Implications, Annals of Internal Medicine, vol. 135, No. 4, pp. 279-295, (2001).

* cited by examiner

INHIBITORS OF THE CHEMOKINE RECEPTOR CXCR3

FIELD OF THE INVENTION

This invention is directed to a 3-(amido or sulphamido)-4-(4-substituted-azinyl)benzamide compound as defined herein. 3-(amido or sulphamido)-(4-substituted-azinyl)benzamide compound is useful as a inhibitor of the chemokine receptor CxCR3, and for preventing or treating a CxCR3 chemokine receptor mediated disease or condition related thereto in a patient in need of such.

BACKGROUND OF THE INVENTION

Chronic inflammatory disorders are a common medical problem, and their incidence increases with aging. The best recognized inflammatory disorder associated with aging is arthritis, a syndromic concept that embraces distinct disorders such as osteoarthritis (e.g. of the knees) and rheumatoid arthritis (e.g., the joints of the fingers). Apart from arthritis, there are other diseases that present with less obvious signs of inflammation. These include chronic obstructive pulmonary disease (COPD), which is a syndromic designation mainly comprised of emphysema, chronic bronchitis and asthma, a disorder of relapsing and remitting neural dysfunction, multiple sclerosis (MS), arteriosclerosis, psoriasis, a desquamating skin condition, and inflammatory bowel disorders (IBD) such as Crohn's disease and ulcerative colitis, both debilitating conditions affecting the upper and lower intestinal tract, respectively. Ulcerative colitis, moreover, is a risk factor for the evolution of colorectal cancer, a leading cause of terminal morbidity and mortality among industrial populations. Being hidden from view, these conditions are not typically known by lay people to be inflammatory in nature, yet pathologists have long demonstrated inflammatory processes in each of these. T-lymphocytes are important players in all of these diseases (Westermann, et al, Ann. Intern. Med. 2001, 135, 279). Many other disorders involve inflammatory phenomena, and they will not be reviewed exhaustively here.

The gross hallmarks of inflammation have been known since antiquity, when Roman physicians codified the four cardinal signs, the "four ors", apparent by physical examination: dolor, rubor, calor and tumor. Dolor is pain, which is demonstrable while working with the patient. Rubor is the red appearance of the affected part, and this hyperemia is caused by the vascular dilatation and increased perfusion of inflamed tissue. This is the body's response to the demands of metabolically stimulated tissues. The dynamics of trafficking of cellular and subcellular components into the field of inflammation and out of it is dramatically increased relative to the basal state, and healing has significant costs in energy and nutritional requirements. The affected region is warmer to the touch than surrounding areas, and this is a reflection of the metabolic burden tissue injury entails. This increased metabolic demand and its consequent supply leads to the third sign, calor, or heat, as the tissue is warm to the touch. Finally, the fourth cardinal sign of inflammation is tumor, or swelling. The net effect of the inflammatory process is an increased amount of material in the affected part. The tissue is swollen with fluid because of increased vascular permeability, and the blood supply delivers a coordinated cast of cellular players such as leukocytes, and later, fibroblasts, first to deal with the cause of injury, and later to heal the injured part.

The traffic of cellular components into inflamed tissue, and their behavior there are highly regulated and orderly. It is not a haphazard process, and the details are becoming better understood. Part of the trafficking of inflamed tissue is a veritable symphony of pro-inflammatory signaling molecules. The cast of cellular players is controlled by factors such as hormones, cytokines and chemokines, and these afford opportunities for therapeutic intervention. The recruitment of specific leukocyte subpopulations, such as T-cells, is regulated by small proteins called chemokines.

Chemokines are a large family of small protein hormones that are among the various factors involved in inflammatory processes (Alexander et al, Br. J. Pharmacol., 2007, 150 (Suppl. 1) S25). The word chemokine is a contraction of the words chemotactic cytokine, and this belies their role. Chemokines attract leukocytes to areas of inflammation. Chemokines also have other effects, modulating the adhesion to extracellular proteins, proliferation and secretion of other factors (e.g., interferon-γ).

Chemokines regulate diverse processes (http://en.wikipedia.org/wiki/Chemokine). A major role of chemokines is to guide cellular migration. Cellular chemotaxis involves the movement of cells from an area with a low concentration of chemokine, to an area with a higher concentration of chemokine. Some chemokines seem to be more homeostatic in function: for example, they direct lymphocytes to the lymph nodes, where they participate in immune surveillance by interacting with antigen-presenting cells within the nodes. Some chemokines have effects on development, such as promoting or inhibiting the growth of new blood vessels—angiogenic and angiostatic effects. Such homeostatic chemokines seem to regulate the trafficking of cells in a day to day manner. Others are expressed in response to injury, and these inflammatory chemokines generally have chemoattractant and other actions on target leukocyte populations. These chemokines are typically induced by interleukin-1 or interferon-γ by various types of cells. Finally, many of the chemokines cause immune cells to release enzymatic and other factors.

Chemokines are small proteins of about 8 to 10 kDa in size stratified according to their protein sequence, and different cell populations respond to them based on the relevant receptors expressed on the cell surface (and Pease and Williams, Br. J. Pharmacol. 2006, 147, S212). To date, at least 47 chemokines are known, and they all have a basic "Greek key" protein folding motif consisting of three anti-parallel β-pleated sheets overlaid by a C-terminal α-helix. This protein fold depends upon conserved intra-chain disulfide bonds. The cysteines that form these bridges are the basis for chemokine nomenclature. Chemokines that have two consecutive cysteines near the amino terminus involved in disulfide bridges are called CC chemokines, and have the systematic name of CCL1 through $CCl_28$. They bind to receptors that are similarly named, CCR1, CCR2, etc, although the numbering of the receptor is not the same as the binding chemokine, and multiple chemokines can bind to each receptor.

Chemokines with an amino acid between the first two cysteines of the amino terminus are called CxC chemokines. The systematic names for these hormones and their receptors are of the type CxCL1 through CxCL16 and the cognate receptors are CxCR1 through CxCR16. While other intercysteinyl spacings are plausible, the next class of chemokine known is $Cx_3CL1$, called fractalkine, and it binds to the receptor $Cx_3CR1$. Finally, there is at least one member of a class of chemokines with only one cysteine of the amino terminal region involved in a disulfide bond, called XCL1, lymphotactin, and its receptor XCR1. Taken altogether, there are 18 receptors known for the 47 known chemokines.

Importantly, splice variants have now become recognized, further subdividing the various chemokines and receptors that can exist. For CxCR3, there are two splice variants known: CxCR3A and CxCR3B. Chemokine receptors are 340-350 amino acids long, and all of them are G-protein coupled receptors (GPCRs). GPCRs are an important class of proteins targeted by various therapeutic agents including small molecule drugs. There is a long-felt need to modulate inflammation, and GPCRs are well-known to offer tractable targets for therapeutic intervention. Thus, there is much hope for the selective modulation of inflammatory processes by the use of modulators of chemokine receptors.

CxCR3A receptors are predominantly expressed on activated Th1 lymphocytes, but it is also present on NK (natural killer) cells, macrophages, DC (dendritic cells) and B lymphocytes. CxCR3A is known to be stimulated by three chemokines: CxCL9 (Monokine induced by interferon-γ, aka Mig), CxCL10, (Interferon-γ inducible 10 kDa protein, aka IP-10) and CxCL11 (Interferon-inducible T-cell α-chemoattractant, aka I-TAC). The observation of angiostatic effects of these chemokines presaged the possibility of a different receptor subtype, and indeed, a splice variant is discovered. CxCR3A signaling is mediated by a pertussis toxin sensitive G protein ($G_\alpha i$), which causes a flux of calcium ions. The splice variant CxCR3B is found to be expressed on endothelial cells and mediates angiostatic effects of IP-10, Mig, I-TAC and Platelet Factor 4 (Lasagni et al, J. Exp. Med. 2003, 197, 1537). Platelet Factor 4, the first chemokine to be sequenced, has no effect on CxCR3A, and signaling through CxCR3B causes a rise of cAMP mediated by $G_\alpha s$.

T lymphocytes have long been known to function as a command and control center of the immune system. Indeed, HIV causes AIDs by the selective destruction of T-cell populations. Given this central regulatory position, it is not surprising that of 18 chemokine receptors, 15 are expressed among the various subpopulations of T lymphocytes (Pease & Williams Br. J. Pharmacol. 2006, 147, S212).

Other pathogens are known to subvert the chemokine system to evade immune surveillance, suppress immune reactions and avoid elimination. Chemokine action is undermined by pathogens in at least four different ways: First, by production of chemokine mimics that act as receptor antagonists. Second, by producing chemokine mimics that act as inappropriate agonists. Third, by producing receptor mimics and fourth, by producing proteins that bind and neutralize chemokine activities (Chensue, Clin. Microbiol. Rev. 2001, 14, 821). CxCR3 and its ligands are among the factors that pathogens usurp. Thus, Nature has found ways to exploit chemokines to modulate functions of the immune system, and the subject of the present invention also exploits it.

Another important property of a control element of a physiological system is the presence of positive and negative regulatory inputs. These balancing points of integration are found among chemokines, too. Eotaxin/CCL11 and MCP-3/CCL7, while stimulatory for other chemokine receptors (CCR3 and CCR1, respectively), antagonize signaling by CxCR3A, and two other CCRs (CCR2 & CCR5). Importantly, the chemokines that stimulate CxCR3A (IP10/CxCL10, I-TAC/CxCL11 and Mig/CxCL9) antagonize signaling through CCR3 expressed on Eosinophils, Basophils and Mast cells (Alexander et al, Br. J. Pharmacol., 2007, 150 (Suppl. 1) S25). Thus, CxCR3A and its ligands are unique in how they are regulated and modulate the behavior of other chemokine signaling pathways. This receptor is at a highly interconnected node within the network of signaling molecules that coordinate inflammation. Indeed, the balance struck between CxCR3A versus CCR3 signaling determines the direction of the inflammatory response, polarizing it from parasite-fighting, allergic responses of the Th2 (CCR3) variety or towards the cell-mediated responses of Th1 (CxCR3A) type. This accounts for the "polarization" of the cellular component of inflammation (Loetscher, et al, J. Biol. Chem. 2001, 276, 2986). Thus, there is a long felt need to discover therapeutic agents that can intervene at this part of the immune response.

The highest level of expression of CxCR3A is seen in T cells, and it is one marker of Th1 lymphocytes (Annunziato, et al, Microbes and Infection, 1999, 1, 103; Lasagni et al, J. Exp. Med. 2003, 197, 1537). T cells are implicated in many diseases listed here in decreasing order of incidence: asthma, Grave's disease, Rheumatoid arthritis, atopic dermititis, Sjogren's syndrome, systemic lupus erythematosis, multiple sclerosis, ulcerative colitis, Type 1 diabetes mellitus, Crohn's disease, sarcoidosis, primary biliary cirrhosis, glomerulonephritis, myasthenia gravis, temporal arteritis, and allogeneic organ transplant rejection (Westermann, et al, Ann. Intern. Med. 2001, 135, 279). The therapeutic potential of CxCR3A modulators now will be illustrated by a few examples of experimental pharmacology.

CxCR3 and its ligands are associated with inflammatory bowel disease. Antibodies to IP10 decreased inflammation in murine models of colitis (Singh, et al, J. Immunol. 2003, 171, 1401). Knockout mice lacking IL-10 ($IL-10^{-/-}$) spontaneously develop colitis that resembles Crohn's Disease. At about 12 weeks of age, these mice begin to lose weight, have chronic diarrhea and circulating levels of serum amyloid A, IL-6 and six other cytokines rise. Treatment with an IP10-neutralizing monoclonal antibody abrogated all of these effects. Histological examination also revealed that the antibody significantly reduced the extent of lymphocytic infiltration into the colonic mucosa.

In rheumatoid arthritis, CxCR3A agonist chemokines are elevated 100 fold in synovial fluid compared to samples from traumatic joint injury or osteoarthritis (Patel, et al, Clin. Immunol., 2001, 98, 39). They also are present in concentrations consistent with a gradient, high to low, from synovial fluid to plasma, and 94% of perivascular T cells express CxCR3A on their surface membranes, and this frequency is enriched over the 40% of T cells with the receptor on their plasma membranes in the blood stream. These findings are consistent with the theory that CxCR3A-binding chemokines are directing the recruitment of Th1 type T cells to the inflamed joints. Thus, for RA, the potential value of intervening at CxCR3A signaling is recognized by several authors (Houshmand & Zlotnik, Curr. Opinion Chem. Biol. 2003, 7, 457; Proudfoot, Nature Reviews Immunol., 2002, 2, 106).

A small molecule inhibitor of the CxCR3A system in arthritic models has been reported. Tak779, which antagonizes CCR5 and CxCR3A (both selectively expressed on Th1 cells—Hashmand & Zlotnick) inhibit pathology of CIA in mice (Yang, et al, Eur. J. Immunol. 2002, 32, 2124; and Gao, et al, J. Leukoc. Biol. 2003, 73, 273). The Collagen Induced Arthritis (CIA) model is a well-established acute arthritis model in mice with a course of 26 days. Mice are immunized with collagen, and within 13 days of the booster injection, nearly all animals have swollen red joints in their limbs. This classical picture of inflammation is ablated by treating CIA mice with TAK-779, a quarternary ammonium salt of a substituted benzocycloheptene originally developed as a drug to block HIV infection. TAK-779 also blocked the leukocytic infiltration of joints as determined by histologic evaluation. Although TAK-779 is originally developed as a CCR5 inhibitor to treat AIDS, it is found to be a CxCR3A blocker with similar potencies as measured in competitive radioligand binding, chemotaxis, and cellular adhesion assays. Two other chemokines expressed in the cell type studied by Gao et al had no effect on these parameters. Thus, TAK-779 is a dual inhibitor for both CCR5 and CxCR3A.

A small molecule compound, AMG-487, has been tested in a murine model of metastatic cancer (Walser, et al, Cancer Res., 2006, 66, 7701). Interestingly, tumor cells often aberrantly express chemokines or their receptors. Investigators believe that this may promote growth or affect tropism of metastatic disease. CxCR3A is expressed in breast cancer cell lines from humans and mice, they functionally couple to calcium responses and impart chemotactic activity to these cells responsive to CxCR3A-specific chemokines. In a mouse model of metastatic breast cancer, AMG-487 reduced the number of metastases by 60%. Interestingly, the compound had no direct effect on proliferation, emphasizing that metastatic tropism and proliferation are dissociable phenomena.

Finally, recent gene knockout experiments in mice predict utility for CxCR3 inhibitors in the treatment of arteriosclerosis (Veillard, et al, Circulation 2005, 112, 870). Mice lacking the ApoE gene rapidly develop atherosclerotic lesions in the aorta when given a high fat diet. When the gene for CxCR3 is knocked out in these mice, the extent of lipid deposits in the thoracoabdominal aorta is reduced from 7.9% of the area to 4.5%.

Thus, there is good reason to believe that modulators of CxCR3A will likely be useful for the treatment of patients with diverse diseases.

Assorted patent applications and issued patents discloses inhibitors of chemokines or CxCR3.

WO 2002/085861, WO 2003/101970, U.S. Pat. No. 7,067,662 B2, U.S. Pat. No. 6,124,319, WO 031070242 A1 and WO 2007/064553 A2 disclose respectively compounds of the following formulae:

US 20070021611 A1, US 20070054919 A1, US 20070082913 A1, WO2008008453 A1, and WO2007/109238 A1 disclose respectively compounds of the following formulae:

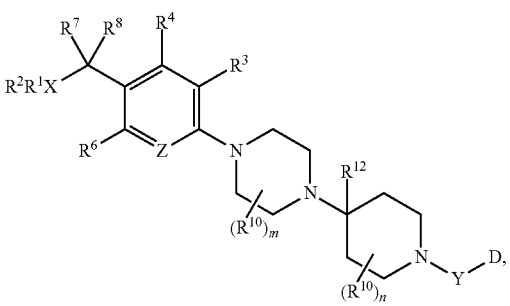

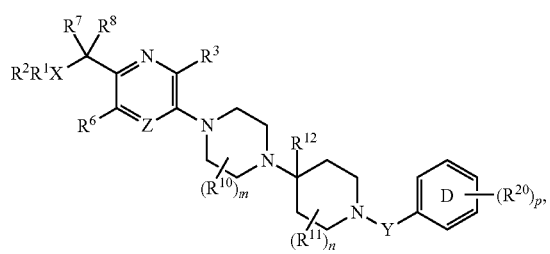

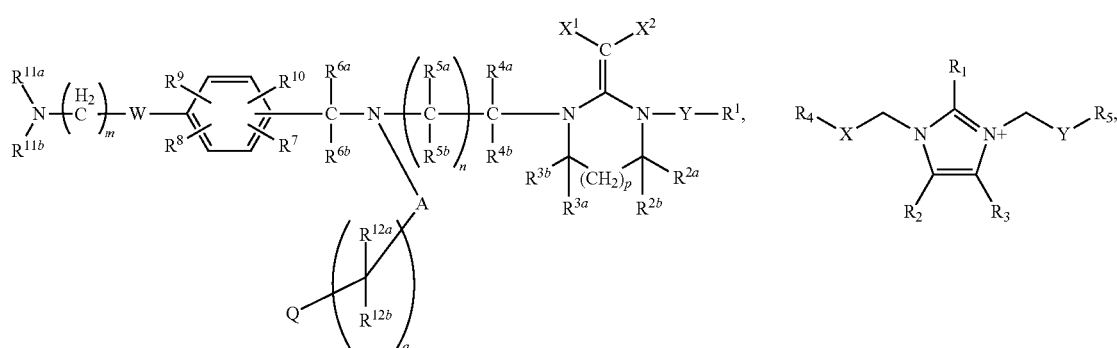

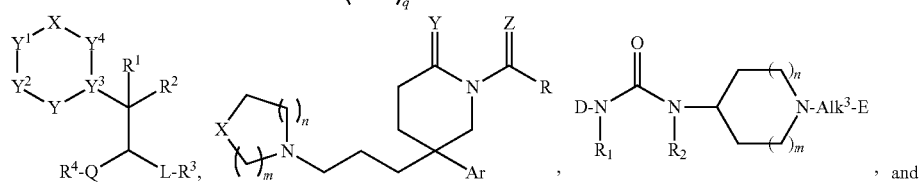

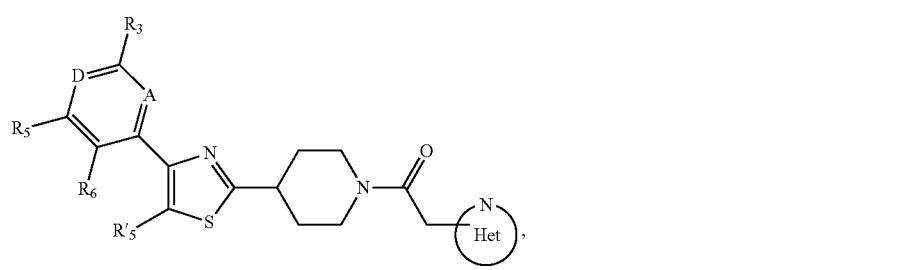

as chemokine receptor inhibitors.

-continued

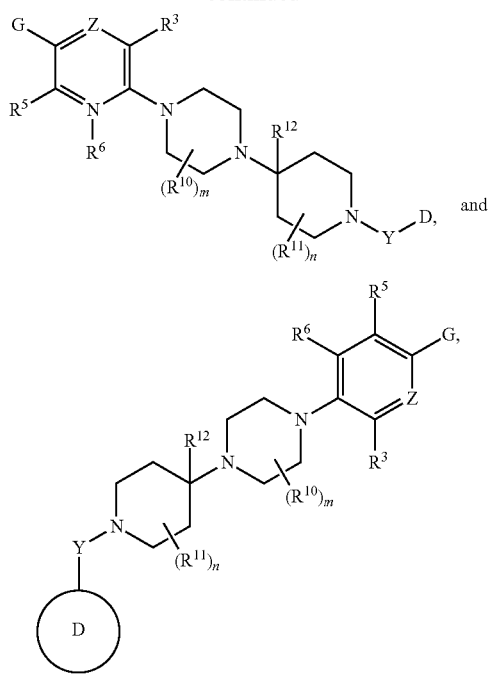

as CxCR3 inhibitor. All these compounds have a (piperidin-4-ylpiperazin-1yl) aromatic moiety core structure.

WO 2007/002742 A1 discloses compounds of the following formula:

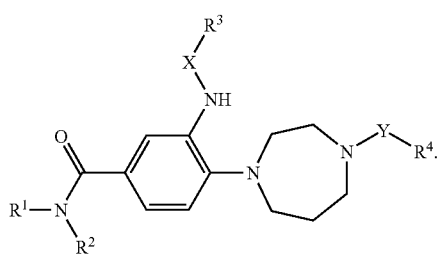

An illustrative compound of that series is as follows:

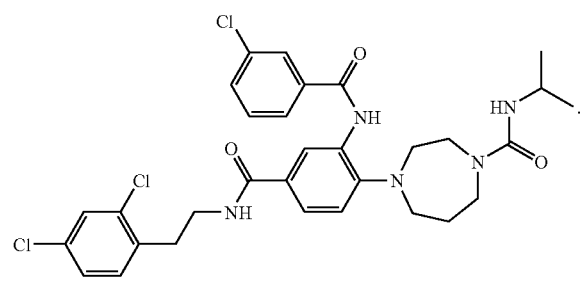

Cole, et al, J. Bioorg. Med. Chem. Lett. 16, 2006, 200-203, noted relative to the aforesaid series that the seven-membered homopiperazine ring is required for activity as the piperazinyl analogue exhibited not activity. Thus, the change of the homopiperazine ring to a piperazine ring is taught against.

SUMMARY OF THE INVENTION

The present invention relates to a 3-(amido or sulphamido)-4-(4-substituted-azinyl)benzamide or benzsulphonamide compound having the formula I

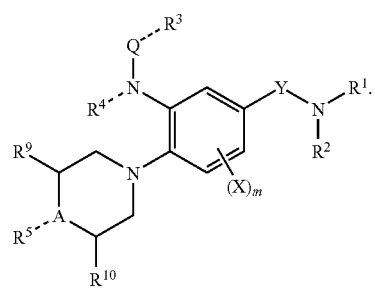

(I)

wherein
Q and $Q^1$ are independently CO or $SO_2$;
Y is CO or $SO_2$;
X is halo;
m is 1, 2 or 3;
$R^1$ is (optionally substituted (aromatic or lower cyclyl)) lower alkyl $C_{1-3}$;
$R^2$, $R^4$ and $R^6$ are independently H or optionally substituted lower alkyl;
$R^3$ is optionally substituted aromatic group;
A is CH or N, or A and $R^5$ taken together form a 4-7 membered spiro azaheterocyclyl of the following formula

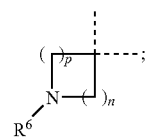

n and p are independently 0, 1, 2, 3, 4 or 5, so long as n and p≧2 but ≦5;
$R^5$ is JGZ, $R^8R^7NQ^1$ lower alkyl or optionally substituted 3-7 membered azaheterocyclyl;
Z is bond, CO or $SO_2$;
G is lower alkyl, $C_{3-7}$ cycloalkyl or 3-7 membered heterocyclyl; and
J is aromatic group, lower alkoxycarbonyl, lower alkylthio, lower alkylsulfinyl, lower alkylsulfonyl, lower alkoxy, $R^8R^7N$ or optionally (lower alkyl or halo) substituted 3-7 membered heterocyclyl;
$R^7$ and $R^8$ are independently H or lower alkyl;
$R^9$ and $R^{10}$ are independently H or lower alkyl; or
a pharmaceutically acceptable salt, solvate, N-oxide, quarternary derivative or prodrug thereof, or any combination thereof.

The invention is also directed to a pharmaceutical composition comprising a pharmaceutically acceptable amount of a compound of formula I, or a pharmaceutically acceptable salt, solvate, N-oxide, quarternary derivative or prodrug thereof, or any combination thereof, and pharmaceutically acceptable additive.

The invention is also directed to a method of preventing or treating a CxCR3 chemokine receptor mediated disease or condition related thereto in a patient in need of such comprising administering to the patient a pharmaceutically effective amount of the compound of formula I, or a pharmaceutically acceptable salt, solvate, N-oxide, quarternary derivative or prodrug thereof, or any combination thereof.

The invention is also directed to the use of one or more compounds of claim 1, to prepare a medicament for treating or preventing a condition where CxCR3 has a role in a patient in need thereof.

The present invention is also directed to a kit or pharmaceutical pack for treating of preventing a physiological condition or a disease state in a patient, wherein the kit or pharmaceutical pack comprises a plurality of separate containers, wherein at least one of said containers contains one or more compounds of claim 1 (alone or in combination with a pharmaceutically acceptable carrier), at least another of said containers contains one or more other compounds capable of treating or preventing the physiological condition or a disease state.

DETAILED DESCRIPTION OF THE INVENTION

List of Abbreviations

As used above, and throughout the description of the invention, the following abbreviations, unless otherwise indicated, shall be understood to have the following meanings:
DIC=diisopropylcarbodiimide
FMOC=9-fluorenylmethyloxycarbonyl
TMOF=trimethylorthoformiate
DIEA=diisopropylethylamine
$NaBH_3CN$=sodium cyanoborohydride
DMF: N,N-Dimethylformamide
THF: Tetrahydrofuran
DMSO: Dimethyl sulfoxide
DCM: Dichloromethane which can also be referred to as methylene chloride
NMP=N-methyl pyrrolidone
MeOH=methanol
HOAt=1-hydroxy-7-azabenzotriazole
HATU=Dimethylamino-([1,2,3]triazolo[4,5-b]pyridin-3-yloxy)-methylene]-dimethyl-ammonium hexafluoro phosphate
HOAc=acetic acid
AN=acetonitrile
TFA=trifluoroacetic acid
HPLC=High Performance Liquid Chromatography
LC/MS=tandem high performance liquid chromatography coupled with mass spectrometry
NMR=nuclear magnetic spectroscopy

Definitions

As used above, and throughout the description of the invention, the following terms, unless otherwise indicated, shall be understood to have the following meanings:—

"Acid protecting group" means an easily removable group that is known in the art to protect an acidic hydrogen of a carboxyl group against undesirable reaction during synthetic procedures, e.g., to block or protect the acid functionality while the reactions involving other functional sites of the compound are carried out, and to be selectively removable. Such acid protecting groups are well known to those skilled in the art, having been extensively used in the protection of carboxyl groups, as described in U.S. Pat. Nos. 3,840,556 and 3,719,66, the disclosures of which are hereby incorporated herein by reference. For suitable acid protecting groups, see T. W. Green and P. G. M. Wuts in "Protective Groups in Organic Chemistry" John Wiley and sons, 1991. Acid protecting group also includes hydrogenation labile acid protecting group as defined herein. Exemplary acid protecting groups include esters such as substituted and unsubstituted $C_{1-8}$ lower alkyl, e.g., methyl, ethyl, t-butyl, methoxymethyl, methylthiomethyl, 2,2,2-trichloroethyl and the like, tetrahydropyranyl, substituted and unsubstituted phenylalkyl such as benzyl and substituted derivatives thereof such as alkoxybenzyl or nitrobenzyl groups and the like, cinnamyl, dialkylaminoalkyl, e.g., dimethylaminoethyl and the like, trimethylsilyl, substituted and unsubstituted amides and hydrazides, e.g., amides and hydrazides on N,N-dimethylamine, 7-nitroindole, hydrazine, N-phenylhydrazine and the like, acyloxyalkyl groups such as pivaloyloxymethyl or propionyloxymethyl and the like, aroyloxyalkyl such as benzoyloxyethyl and the like, alkoxycarbonylalkyl such as methoxycarbonylmethyl, cyclohexyloxycarbonylmethyl and the like, alkoxycarbonyloxyalkyl such as t-butyloxycarbonyloxymethyl and the like, alkoxycarbonylaminoalkyl such as t-butyloxycarbonylaminomethyl and the like, alkylaminocarbonylaminoalkyl, such as methylaminocarbonylaminomethyl and the like, acylaminoalkyl such as acethylaminomethyl and the like, heterocyclylcarbonyloxyalkyl such as 4-methylpiperazinyl-carbonyloxymethyl and the like, dialkylaminocarbonyalkyl such as dimethylaminocarbonyl-methyl and the like, (5-(lower alkyl)-2-oxo-1,3-dioxolen-4-yl)alkyl such as (5-t-butyl-2-oxo-1,3-dioxolen-4-yl)methyl and the like, and (5-phenyl-2-oxo-1,3-dioxolen-4-yl)alkyl such as (5-phenyl-2-oxo-1,3-dioxolen-4-yl)methyl and the like.

"Acid labile amine protecting group" means an amine-protecting group as defined herein that is readily removed by treatment with acid while remaining relatively stable to other reagents. A preferred acid labile amine-protecting group is BOC.

"Acyl" means an H—CO— or (aliphatic or cyclyl)-CO— group wherein the aliphatic group is as herein described. Preferred acyls contain a lower alkyl. Exemplary acyl groups include formyl, acetyl, propanoyl, 2-methylpropanoyl, butanoyl, palmitoyl, acryloyl, propynoyl, cyclohexylcarbonyl, and the like.

"Alkenoyl" means an alkenyl-CO— group wherein alkenyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. Branched means that one or more lower alkyl groups such as methyl, ethyl or propyl are attached to a linear alkenyl chain. "Lower alkenyl" means about 2 to about 4 carbon atoms in the chain that may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl, decenyl, and the like. "Substituted alkenyl" means an alkenyl group as defined above which is substituted with one or more "aliphatic group substituents" (preferably 1 to 3) which may be the same or different and are as defined herein. Exemplary alkenyl aliphatic group substituents include halo or cycloalkyl groups.

"Alkenyloxy" means an alkenyl-O— group wherein the alkenyl group is as herein described. Exemplary alkenyloxy groups include allyloxy, 3-butenyloxy, and the like.

"Alkoxy" means an alkyl-O— group wherein the alkyl group is as herein described. Exemplary alkoxy groups include methoxy, ethoxy, n-propoxy, i-propoxy, n-butoxy, heptoxy, and the like.

"Alkoxycarbonyl" means an alkyl-O—CO— group, wherein the alkyl group is as herein defined. Exemplary alkoxycarbonyl groups include methoxycarbonyl, ethoxycarbonyl, t-butyloxycarbonyl, and the like.

"Alkyl" means an aliphatic hydrocarbon group which may be straight or branched having about 1 to about 20 carbon atoms in the chain. Preferred alkyl groups have 1 to about 12 carbon atoms in the chain, more preferred is lower alkyl as defined herein. Branched means that one or more lower alkyl groups such as methyl, ethyl or propyl are attached to a linear alkyl chain. "Lower alkyl" means about 1 to about 4 carbon atoms in the chain that may be straight or branched. "Substituted alkyl" means an alkyl group as defined above which is substituted with one or more phenyl or halo substituents (preferably 1 to 3), including perfluorinated substituted alkyl, as are defined herein.

"Alkylsulfinyl" means an alkyl-SO— group wherein the alkyl group is as defined above. Preferred groups are those wherein the alkyl group is lower alkyl.

"Alkylsulfonyl" means an alkyl-$SO_2$— group wherein the alkyl group is as defined above. Preferred groups are those wherein the alkyl groups is lower alkyl.

"Alkylsulfonylcarbamoyl" means an alkyl-$SO_2$—NH—C(=O)— group wherein the alkyl group is as herein described. Preferred alkysulfonylcarbamoyl groups are those wherein the alkyl group is lower alkyl.

"Alkylthio" means an alkyl-S— group wherein the alkyl group is as herein described. Exemplary alkylthio groups include methylthio ethylthio i-propylthio and heptylthio.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about r carbon atoms in the chain. Branched means that one or more lower alkyl groups such as methyl, ethyl or propyl are attached to a linear alkynyl chain. "Lower alkynyl" means about 2 to about 4 carbon atoms in the chain that may be straight or branched. The alkynyl group may be substituted by one or more halo. Exemplary alkynyl groups include ethynyl, propynyl, n-butynyl, 2-butynyl, 3-methylbutynyl, n-pentynyl, heptynyl, octynyl, decynyl, and the like. "Substituted alkynyl" means alkynyl as defined above which is substituted with one or more "aliphatic group substituents" (preferably 1 to 3) which may be the same or different, and are as defined herein.

"Amine protecting group" means an easily removable group that is known in the art to protect a nitrogen moiety of an amino group against undesirable reaction during synthetic procedures and to be selectively removable. The use of amine protecting groups is well known in the art for protecting groups against undesirable reactions during a synthetic procedure and many such protecting groups are known, for example, T. W. Greene and P. G. M. Wuts, Protective groups in Organic synthesis, $2^{nd}$ edition, John Wiley & Sons, New York (1991), incorporated herein by reference. Amine protecting group also includes "acid labile amine protecting group" and "hydrogenation labile amine protecting group". Exemplary amine protecting groups are acyl, including formyl, acetyl, chloroacetyl, trichloroacetyl, o-nitrophenylacetyl, o-nitrophenoxy-acetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy including methoxy-carbonyl, 9-fluorenylmethoxycarbonyl, 2,2,2-trifluoroethoxycarbonyl, 2-trimethylsilylethoxy-carbonyl, vinyloxycarbonyl, allyloxycarbonyl, t-butyloxycarbonyl (BOC), 1,1-dimethyl-propynyloxycarbonyl, benzyloxycarbonyl (CBZ), p-nitrobenzyloxycarbonyl, 2,4-dichloro-benzyloxycarbonyl, and the like.

"Amide protecting group" means an easily removable group that is known in the art to protect a nitrogen moiety of an amide group against undesirable reaction during synthetic procedures and to be selectively removable after its conversion to the amide. The use of amide protecting groups is well known in the art for protecting groups against undesirable reactions during a synthetic procedure and many such protecting groups are known for example, T. W. Greene and P. G. M. Wuts, Protective Groups in Organic Synthesis, $2^{nd}$ edition, John Wiley & Sons, New York (1991), incorporated herein by reference. Amide protecting group also includes "acid labile amide protecting group" and "hydrogenation labile amide protecting group". Exemplary amide protecting groups are o-nitrocinnamoyl, picolinoyl, aminocaproyl, benzoyl and the like, and acyloxy including methoxy-carbonyl, 9-fluorenylmethoxycarbonyl, 2,2,2-trifluoroethoxycaronyl, 2-trimethylsilyethoxy-carbonyl, vinyloxycarbonyl, allyloxycarbonyl, t-butyloxycarbonyl (BOC), 1,1-dimethyl-propynyloxycarbonyl, benzyloxycarbonyl (CBZ), p-nitrobenzyloxycarbonyl, 2,4-dichloro-benzyloxycarbonyl, and the like.

"Aromatic" group means aryl or heteroaryl as defined herein. Exemplary aromatic groups include phenyl, halo substituted phenyl, azaheteroaryl, and the like.

"Aroyl" means an aryl-CO-group wherein the aryl group is as herein described. Exemplary aroyl groups include benzoyl, 1- and 2-naphthoyl, and the like.

"Aryl" means an aromatic monocyclic or multicyclic ring system of about 6 to about 14 carbon atoms, preferably of about 6 to 10 carbon atoms. Encompassed by aryl are fused cycloalkenylaryl, fused cycloalkylaryl, fused heterocyclenylaryl and fused heterocyclylaryl as defined herein when bonded through the aryl moiety thereof. The aryl is optionally substituted with one or more "ring group substituents" (preferably 1 to 3 substituents which may be the same or different, and are as defined herein. A "Substituted aryl" means an aryl group which is substituted as defined above. Exemplary aryl groups include phenyl, or substituted phenyl.

"Aryldiazo" means an aryl-diazo-group wherein the aryl and diazo groups are as defined herein.

"Aryloxy" means an aryl-O— group wherein the aryl group is as defined herein. Exemplary aryloxy groups include phenoxy and 2-naphtyloxy.

"Aryloxycarbonyl" means an aryl-O—CO— group wherein the aryl group is as defined herein. Exemplary aryloxycarbonyl groups include phenoxycarbonyl and naphthoxycarbonyl.

"Arylsulfonyl" means an aryl-$SO_2$— group wherein the aryl group is defined herein.

"Arylsulfonylcarbamoyl" means an aryl-$50_2$—NH—C(=O)-group wherein the aryl group is herein described. An exemplary arylsulfonylcarbamoyl group is phenylsulfonylcarbamoyl.

"Arylsulfinyl" means an aryl-$SO_2$— group wherein the aryl group is as defined herein.

"Arylthio" means an aryl-S— group wherein the aryl group is as herein described. Exemplary arylthio groups include phenylthio and naphthylthio.

"Basic nitrogen atom" means a $sp^2$ or $sp^3$ hybridized nitrogen atom having a non-bonded pair of electrons which is capable of being protonated. Exemplary basic nitrogen atoms include optionally substituted imino, optionally substituted amino and optionally substituted amidino groups.

"Carboxy" means an HO(O)C— (carboxylic acid) group.

"Coupling agent" means a compound that reacts with the hydroxyl moiety of a carboxy moiety thereby rendering it susceptible to nucleophilic attack. Exemplary coupling agents include DIC, EDCI, DCC, and the like.

"Cycloalkenyl" means an optionally substituted non aromatic mono- or multicyclic ring system of about 3 to about 10 carbon atoms, preferably of about 3 to about 6 carbon atoms (lower cycloalkenyl), and which contains at least one carbon-carbon double bond and which can be optionally fused by an aromatic group as defined herein. "Fused (aromatic) "cycloalkenyl" means fused arylcycloalkenyl and fused heteroarylcycloalkenyl as defined herein bonded through the cycloalkenyl moiety thereof. Preferred sizes or the rings of the ring system are about 5 to about 6 ring atoms; and such preferred ring sizes are also referred to as "lower". "Substituted cycloalkenyl" means an cycloalkenyl group as defined above which is substituted with one or more "ring group substituents" (preferably 1 to 3) which may be the same or different and are defined herein. Exemplary monocyclic cycloalkenyl include cyclopentenyl, cyclohexenyl, cycloheptenyl, and the like. An exemplary multicyclic cycloalkenyl is norbornylenyl.

"Cycloalkyl" means a non-aromatic mono- or multicyclic ring system of about 3 to about 10 carbon atoms, preferably of about 3 to about 6 carbon atoms (lower cycloalkyl), and which can be optionally fused by an aromatic group as defined herein. "Fused (aromatic) cycloalkyl" means fused arylcycloalkyl and fused heteroarylcycloalkyl as defined herein bonded through the cycloalkyl moiety thereof. "Substituted cycloalkyl" means a cycloalkyl group as defined above which is substituted with one or more "ring group substituents" (preferably 1 to 3) which may be the same or different and are defined herein. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

"Cyclic" or "Cyclyl" means cycloalkyl, cycloalkenyl, heterocyclyl or heterocyclenyl as defined herein. The term "lower" as used in connection with the term cyclic is the same as noted herein regarding the cycloalkyl, cycloalkenyl, heterocyclyl or heterocyclenyl.

"Cyclyloxy" means a cyclyl-O— group wherein the cyclyl group is as herein described. Exemplary cycloalkoxy groups include cyclopentyloxy, cyclohexyloxy, quinuclidyloxy, pentamethylenesulfidoxy, tetrahydropyranyloxy, tetrahydrothiophenyloxy, pyrrolidinyloxy, tetrahydrofuranyloxy, or 7-oxabicyclo[2.2.1]heptanyloxy, hydroxytetrahydropyranyloxy, hydroxy-7-oxabicyclo[2.2.1]heptanyloxy, and the like.

"Cyclylsulfinyl" means a cyclyl-S(O)— group wherein the cyclyl group is as herein described.

"Cyclylsulfonyl" means a cyclyl-S(O)$_2$— group wherein the cyclyl group is as herein described.

"Cyclylthio" means a cyclyl-S— group wherein the cyclyl group is as herein described.

"Diazo" means a bivalent —N═N— radical.

"Effective amount" is means an amount of a compound/composition according to the present invention effective in producing the desired therapeutic effect.

"Fused arylcycloalkenyl" means a fused aryl and cycloalkenyl as defined herein. Preferred fused arylcycloalkenyls are those wherein the aryl thereof is phenyl and the cycloalkenyl consists of about 5 to about 6 ring atoms. A fused arylcycloalkenyl as a variable may be bonded through any atom of the ring system thereof capable of such. "Substituted fused arylcycloalkenyl" means a fused arylcycloalkenyl group as defined above which is substituted with one or more "ring group substituents" (preferably 1 to 3) which may be the same or different and are as defined herein. Exemplary fused arylcycloalkenyl include 1,2-dihydronaphthylene, indene, and the like.

"Fused arylcycloalkyl" means a fused aryl and cycloalkyl as defined herein. Preferred fused arylcycloalkyls are those wherein the aryl thereof is phenyl and the cycloalkyl consists of about 5 to about 6 ring atoms. A fused arylcycloalkyl as a variable may be bonded through any atom of the ring system thereof capable of such. "Substituted fused arylcycloalkyl" means a fused arylcycloalkyl group as defined above which is substituted with one or more "ring group substituents" (preferably 1 to 3) which may be the same or different and are as defined herein. Exemplary fused arylcycloalkyl includes 1,2,3,4-tetrahydro-naphthylene, and the like.

"Fused arylheterocyclenyl" means a fused aryl and heterocyclenyl as defined herein. Preferred fused arylheterocyclenyls are those wherein the aryl thereof is phenyl and the heterocyclenyl consists of about 5 to about 6 ring atoms. A fused arylheterocyclenyl as a variable may be bonded through any atom of the ring system thereof capable of such. The designation of the aza, oxa or thia as a prefix before heterocyclenyl portion of the fused arylheterocyclenyl define that at least a nitrogen, oxygen or sulfur atom is present, respectively, as a ring atom. "Substituted fused arylheterocyclenyl" means a fused arylheterocyclenyl group as defined above which is substituted with one or more "ring group substituents" (preferably 1 to 3) which may be the same or different and are as defined herein. The nitrogen atom of a fused arylheterocyclenyl may be a basic nitrogen atom. The nitrogen or sulfur atom of the heterocyclenyl portion of the fused arylheterocyclenyl may also be optionally oxidized to the corresponding N-oxide, S-oxide or S,S-dioxide. Exemplary fused arylheterocyclenyl include 3H-indolinyl, IH-2-oxoquinolyl, 2H-1-oxoisoquinolyl, 1,2-di-hydroquinolinyl, 3,4-dihydroquinolinyl, 1,2-dihydroisoquinolinyl, 3,4-dihydroisoquinolinyl, and the like.

"Fused arylheterocyclyl" means a fused aryl and heterocyclyl as defined herein. Preferred fused arylheterocyclyls are those wherein the aryl thereof is phenyl and the heterocyclyl consists of about 5 to about 6 ring atoms. A fused arylheterocyclyl as a variable may be bonded through any atom of the ring system thereof capable of such. The designation of the aza, oxa or ilia as a prefix before heterocyclyl portion of the fused arylheterocyclyl define that at least a nitrogen, oxygen or sulfur atom is present, respectively, as a ring atom. "Substituted fused arylheterocyclyl" means a fused arylheterocyclyl group as defined above which is substituted with one or more "ring group substituents" (preferably 1 to 3) which may be the same or different and are as defined herein. The nitrogen atom of a fused arylheterocyclyl may be a basic nitrogen atom. The nitrogen or sulfur atom of the heterocyclyl portion of the fused arylheterocyclyl may also be optionally oxidized to the corresponding N-oxide, S-oxide or S,S-dioxide. Exemplary fused arylheterocyclyl ring systems include indolinyl, 1,2,3,4-tetrahydroisoquinoline, 1,2,3,4-tetrahydroquinoline, 1H-2,3-dihydroisoindol-2-yl, 2,3-dihydrobenz[f]isoindol-2-yl, 1,2,3,4-tetrahydrobenz[g]-isoquinolin-2-yl, and the like.

"Fused heteroarylcycloalkenyl" means a fused heteroaryl and cycloalkenyl as defined herein. Preferred fused heteroarylcycloalkenyls are those wherein the heteroaryl thereof is phenyl and the cycloalkenyl consists of about 5 to about 6 ring atoms. A fused heteroaryl-cycloalkenyl as a variable may be bonded through any atom of the ring system thereof capable of such. The designation of the aza, oxa or thia as a prefix before heteroaryl portion of the fused heteroarylcycloalkenyl define that at least a nitrogen, oxygen or sulfur atom is present, respectively, as a ring atom. "Substituted fused heteroarylcycloalkenyl" means a fused heteroarylcycloalkenyl group as defined above which is substituted with one or more "ring group substituents" (preferably 1 to 30 which may be the same or different and are as defined herein. The nitrogen atom of a fused heteroarylcycloalkenyl may be a basic nitrogen atom. The nitrogen atom of the heteroaryl portion of the fused heteroarylcycloalkenyl may also be optionally oxidized to the corresponding N-oxide. Exemplary fused heteroarylcycloalkenyls include 5,6-dihydroquinolyl, 5,6-dihydroisoquinolyl, 5,6-dihydroquinoxalinyl, 5,6-dihydroquinazolinyl, 4,5-dihydro-1H-benzimidazolyl, 4,5-di-hydrobenzoxazolyl, and the like.

"Fused heteroarylcycloalkyl" means a fused heteroaryl and cycloalkyl as defined herein. Preferred fused heteroarylcycloalkyls are those wherein the heteroaryl thereof consists of about 5 to about 6 ring atoms and the cycloalkyl consists of about 5 to about. 6 ring atoms. A fused heteroarylcycloalkyl as a variable may be bonded through any atom of the ring system thereof capable of such. The designation of the aza, oxa or ilia as a prefix before heteroaryl portion of the fused heteroarylcycloalkyl define that at least a nitrogen, oxygen or sulfur atom is present, respectively, as a ring atom. "Substituted fused heteroarylcycloalkyl" means a fused heteroarylcycloalkyl group as defined above which is substituted with one or more "ring group substituents" (preferably 1 to 3) which may be the same or different and are as defined herein. The nitrogen atom of a fused heteroarylcycloalkyl may be a basic nitrogen atom. The nitrogen atom of the heteroaryl portion of the fused heteroarylcycloalkyl may also be optionally oxidized to the corresponding N-oxide. Exemplary fused heteroarylcycloalkyl include 5,6,7,8-tetrahydroquinolinyl, 5,6,7,8-tetra-hydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, and the like.

"Fused heteroarylheterocyclenyl" means a fused heteroaryl and heterocyclenyl as defined herein. Preferred fused heteroarylheterocyclenyls are those wherein the heteroaryl thereof consists of about 5 to about 6 ring atoms and the heterocyclenyl consists of about 5 to about 6 ring atoms. A fused heteroarylheterocyclenyl as a variable may be bonded through any atom of the ring system thereof capable of such. The designation of the aza, oxa or thia as a prefix before the heteroaryl or heterocyclenyl portion of the fused heteroarylheterocyclenyl define that at least a nitrogen, oxygen or sulfur atom is present, respectively, as a ring atom "Substituted fused heteroarylheterocyclenyl" means a fused heteroarylheterocyclenyl group as defined above which is substituted with one or more "ring group substituents" (preferably 1 to 3) which may be the same or different and are as defined herein. The nitrogen atom of a fused heteroarylazaheterocyclenyl may be a basic nitrogen atom. The nitrogen or sulfur atom of the heteroaryl portion of the fused heteroarylheterocyclyl may also be optionally oxidized to the corresponding N-oxide. The nitrogen or sulfur atom of the heteroaryl or heterocyclyl portion of the fused heteroarylheterocyclyl may also be optionally oxidized to the corresponding N-oxide, S— oxide or S,S-dioxide. Exemplary fused heteroarylheterocyclenyl include 7,8-dihydro[1,7]naphthyridinyl, 1,2-dihydro[2,7]-naphthyridinyl, 6,7-dihydro-3H-imidazo[4,5-c]pyridyl, 1,2-dihydro-1,5-naphthyridinyl, 1,2-dihydro-1,6-naphthyridinyl, 1,2-dihydro-1,7-naphthyridinyl, 1,2-dihydro-1,8-naphthyridinyl. 1,2-dihydro-2,6-naphthyridinyl, and the like.

"Fused heteroarylheterocyclyl" means a fused heteroaryl and heterocyclyl as defined herein. Preferred fused heteroarylheterocyclyls are those wherein the heteroaryl thereof consists of about 5 to about 6 ring atoms and the heterocyclyl consists of about 5 to about 6 ring atoms. A fused heteroarylheterocyclyl as a variable may be bonded through any atom of the ring system thereof capable of such. The designation of the aza, oxa or ilia as a prefix before the heteroaryl or heterocyclyl portion of the fused heteroarylheterocyclyl define that at least a nitrogen, oxygen or sulfur atom is present, as a ring atom. "Substituted fused heteroarylheterocyclyl" means a fused heteroarylheterocyclyl group as defined above which is substituted with one or more "ring group substituents" (preferably 1 to 3) which may be the same or different and are as defined herein The nitrogen atom of a fused heteroarylheterocyclyl may be a basic nitrogen, atom. The nitrogen or sulfur atom of the heteroaryl portion of the fused heteroarylheterocyclyl may also be optionally oxidized to the corresponding N-oxide. The nitrogen or sulfur atom of the heteroaryl or heterocyclyl portion of the fused heteroarylheterocyclyl may also be optionally oxidized to the corresponding N-oxide, S-oxide or S,S-dioxide. Exemplary fused heteroarylheterocyclyl include 2,3-dihydro-1H pyrrol[3,4-b] quinolin-2-yl, 1,2,3,4-tetrahydrobenz[b][1,7]naphthyridin-2-yl, 1,2,3,4-tetrahydrobenz[b][1,6]naphthyridin-2-yl, 1,2,3, 4-tetra-hydro-9H-pyrido[3,4-b]indol-2yl, 1,2,3,4-tetrahydro-9H-pyrido[4,3-b]indol-2yl, 2,3-dihydro-1H-pyrrolo[3,4-b]indol-2-yl, 1H-2,3,4,5-tetrahydroazepino[3,4-b]indol-2-yl, 1H-2,3,4,5-tetra-hydroazepino[4,3-b]indol-3-yl, 1H-2,3,4,5-tetrahydroazepino[4,5-b]indol-2yl, 5,6,7,8-tetra-hydro[1,7]naphthyridyl, 1,2,3,4-tetrhydro[2,7]naphthyridyl, 2,3-dihydro[1,4]dioxino[2,3-b]pyridyl, 2,3-dihydro-[1,4]dioxino[2,3-b]pyridyl, 3,4-dihydro-2H-1-oxa[4,6]diazanaphthalenyl, 4,5,6,7-tetrahydro-3H-imidazo[4,5-c]pyridyl, 6,7-dihydro[5,8]diazanaphthalenyl, 1,2,3,4-tetrahydro[1,5]-naphthyridinyl, 1,2,3,4-tetrahydro[1,6] naphthyridinyl, 1,2,3,4-tetrahydro[1,7]naphthyridinyl, 1,2,3, 4-tetrahydro[1,8]naphthyridinyl, 1,2,3,4-tetra-hydro[2,6] naphthyridinyl, and the like.

"Halo" means fluoro, chloro, bromo, or iodo. Preferred are fluoro, chloro or bromo, and more preferred are fluoro or chloro.

"Heteroaroyl" means an heteroaryl-CO— group wherein the heteroaryl group is as herein described. Exemplary heteroaroyl groups include thiophenoyl, nicotinoyl, pyrrol-2-ylcarbonyl, 1- and 2-naphthoyl, pyridinoyl, and the like.

"Heteroaryl" means an aromatic monocyclic or multicyclic ring system of about 5 to about 14 carbon atoms, preferably about 5 to about 10 carbon atoms, in which one or more of the carbon atoms in the ring system is/are hetero element(s) other than carbon, for example nitrogen, oxygen or sulfur. Preferably the ring system includes 1 to 3 heteroatoms. Preferred ring sizes of rings of the ring system include about 5 to about 6 ring atoms. Encompassed by heteroaryl are fused heteroarylcycloalkenyl, fused heteroarylcycloalkyl, fused heteroarylheterocyclenyl and fused heteroarylheterocyclyl as defined herein when bonded through the heteroaryl moiety thereof. "Substituted heteroaryl" means a heteroaryl group as defined above which is substituted with one or more "ring group substituents" (preferably 1 to 3) which may be the same or different and are as defined herein. The designation of the aza, oxa or thia as a prefix before heteroaryl define that at least a nitrogen, oxygen or sulfur atom is present, respectively, as a ring atom. A nitrogen atom of an heteroaryl may be a basic nitrogen atom and may also be optionally oxidized to the corresponding N-oxide. Exemplary heteroaryl and substituted heteroaryl groups include pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a]pyridine, imidazo[2,1-b]thiazolyl, benzofurazanyl, azaindolyl, benzimidazolyl, benzothienyl, thienopyridyl, thienopyrimidyl, pyrrolopyridyl. imidazopyridyl, benzoazaindolyl, 1,2,4-triazinyl, benzthiazolyl, furanyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl, triazolyl, and the like. A preferred heteroaryl group is pyrazinyl.

"Heteroaryldiazo" means a heteroaryl-azo-group" wherein the heteroaryl and azo groups are as defined herein.

"Heteroarylsulfonylcarbamoyl" means a heteroaryl-$SO_2$—NH—C(=O)— group wherein the heteroaryl group is as herein described.

"Heterocyclenyl" means a non-aromatic monocyclic or multicyclic hydrocarbon ring system of about 3 to about 10 carbon atoms, preferably about 4 to about 6 carbon atoms (lower heterocyclenyl), in which one or more of the carbon atoms in the ring system is/are hetero element(s) other than carbon, for example nitrogen, oxygen or sulfur atoms, and which contains at least one carbon-carbon double bond or carbon-nitrogen double bond. Preferably, the ring includes 1 to 3 heteroatoms. Encompassed by heterocyclenyl are fused arylheterocyclenyl and fused heteroarylheterocyclenyl as defined herein when bonded through the heterocyclenyl moiety thereof. The designation of the aza, oxa or thia as a prefix before heterocyclenyl define that at least a nitrogen, oxygen or sulfur atom is present, respectively, as a ring atom. "Substituted heterocyclenyl" means a heterocyclenyl group as defined above which is substituted with one or more "ring group substituents" (preferably 1 to 3) which may be the same or different and are as defined herein. The nitrogen atom of an heterocyclenyl may be a basic nitrogen atom. The nitrogen or sulfur atom of the heterocyclenyl may also be optionally oxidized to the corresponding N-oxide, S-oxide or S,S-dioxide. Exemplary monocyclic azaheterocyclenyl groups include 1,2,3,4-tetrahydrohydropyridine, 1,2-dihydropyridyl, 1,4-dihydropyridyl, 1,2,3,6-tetra-hydropyridine, 1,4,5,6-tetrahydro-pyrimidine, 2-pyrrolinyl, 3-pyrrolinyl, 2-imidazolinyl, 2-pyrazolinyl, and the like. Exemplary oxaheterocyclenyl groups include 3,4-dihydro-2H-pyran, dihydrofuranyl, and fluorodihydro-furanyl. An exemplary multicyclic oxaheterocyclenyl group is 7-oxabicyclo[2.2.1]heptenyl. Exemplary monocyclic thiaheterocyclenyl rings include dihydrothiophenyl and dihydrothiopyranyl.

"Heterocyclyl" means a non-aromatic saturated monocyclic or multicyclic ring system of about 3 to about 10 carbon atoms, preferably about 4 to about 6 carbon atoms (lower heterocyclyl), in which one or more of the carbon atoms in the ring system is/are hetero element(s) other than carbon, for example nitrogen, oxygen or sulfur. Preferably, the ring system contains from 1 to 3 heteroatoms. Encompassed by heterocyclyl are fused arylheterocyclyl and fused heteroarylheterocyclyl as defined herein when bonded through the heterocyclyl moiety thereof. The designation of the aza, oxa or thia as a prefix before heterocyclyl define that at least a nitrogen, oxygen or sulfur atom is present respectively as a ring atom. "Substituted heterocyclyl" means a heterocyclyl group as defined above which is substituted with one or more "ring group substituents" (preferably 1 to 3) which may be the same or different and are as defined herein The nitrogen atom of an heterocyclyl may be a basic nitrogen atom. The nitrogen or sulfur atom of the heterocyclyl may also be optionally oxidized to 20 the corresponding N-oxide, S-oxide or S,S-dioxide. Exemplary monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Hydrate" means a solvate wherein the solvent molecule{s} is/are $H_2O$.

"Hydrogenation labile amine protecting group" means an amine protecting group as defined herein which is readily removed by hydrogenation while remaining relatively stable to other reagents. A preferred hydrogenation labile amine protecting group is Cbz.

"Hydrogenation labile acid protecting group" means an acid protecting group as defined herein which is readily removed by hydrogenation while remaining relatively stable to other reagents. A preferred hydrogenation labile acid protecting group is benzyl.

"Patient" includes both human and other mammals.

"Pharmaceutically acceptable prodrugs" as used herein refers to those prodrugs of the compounds of the present invention which are, within the scope of sound medical judgment, suitable for use in contact with the tissues of patients with undue toxicity, irritation, allergic response, and the like, commensurate with a reasonable benefit/risk ratio, and effective for their intended use of the compounds of the invention. The term "prodrug" refers to compounds that are rapidly transformed in vivo to yield the parent compound of the above formula, for example by hydrolysis in blood. Functional groups that may be rapidly transformed, by metabolic cleavage, in vivo form a class of groups reactive with the carboxyl group of the compounds of this invention. They include, but are not limited to such groups as alkanoyl (such as acetyl, propanoyl, butanoyl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds of this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion is provided in Design of Prodrugs, H. Bundgaard, ed., Elsevier (1985); Methods in Enzymology; K. Widder et al, Ed., Academic Press, 42, 309-396 (1985); A Textbook of Drug Design and Development, Krogsgaard-Larsen and H. Bandaged, ed., Chapter 5; "Design and Applications of Prodrugs" 113-191 (1991); Advanced Drug Delivery Reviews, H. Bundgard, 8, 1-38, (1992); J. Pharm. Sci., 77, 285 (1988); Chem. Pharm. Bull., N. Nakeya et al, 32, 692 (1984); Pro-drugs as Novel Delivery Systems, T. Higuchi and V. Stella, 14 A.C.S. Symposium Series, and Bioreversible Carriers in Drug Design, E.B. Roche, ed., American Pharmaceutical Association and Pergamon Press, 1987, which are incorporated herein by reference.

"Pharmaceutically acceptable salts" refers to the relatively non-toxic, inorganic and organic acid addition salts, and base addition salts, of compounds of the present invention. These: salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-β-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," *J. Pharm. Sci.*, 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabiethylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

"Quaternary derivative" means a sp3 hybridized amine that is alkylated with a lower alkyl group.

"Ring group substituents" mean substituents attached to aromatic or non-aromatic ring systems inclusive of aryl, heteroaryl, hydroxy, alkoxy, cyclyloxy, aryloxy, heteroaryloxy, acyl or its thioxo analogue, cyclylcarbonyl or its thioxo analogue, aroyl or its thioxo analogue heteroaroyl or its thioxo analogue, acyloxy, cyclylcarbonyloxy, aroyloxy, heteroaroyloxy, halo, nitro, cyano, carboxy (acid), —C(O)—NHOH—C(O)—CH$_2$0H, —C(O)—CH$_2$SH—C(O)—NH—CN, sulfo, phosphono, alkylsulfonylcarbamoyl, tetrazolyl, arylsulfonylcarbamoyl, N-methoxycarbamoyl. heteroarylsulfonylcarbamoyl, 3-hydroxy-3-cyclobutene-1,2-dione, 3,5-dioxo-1,2,4-oxadiazolidinyl or hydroxyheteroaryl such as 3-hydroxyisoxazolyl,3-hydroxy-1-methylpyrazoly, alkoxycarbonyl, cyclyloxycarbonyl, aryloxycarbonyl, heteroaryloxycarbonyl, alkylsulfonyl. cyclylsulfonyl, arylsulfonyl, heteroarylsulfonyl, alkylsulfinyl, cyclylsulfinyl, arylsulfinyl, heteroarylsulfinyl, alkylthio, cyclylthio, arylthio, heteroarylthio, cyclyl, aryldiazo, heteroaryldiazo, thiol, $Y^1Y^2N$—, $Y^1Y^2NC(O)$—, $Y^1Y^2NC(O)O$—, $Y^1Y^2NC(O)NY^3$— or $Y^1Y^2NSO_2$—, wherein $Y^1$, $Y^2$ and $Y^3$ are independently hydrogen, alkyl, aryl or heteroaryl. or for where the substituent is $Y^1Y^2N$—, then one of $Y^1$ and $Y^2$ may be acyl, cyclylcarbonyl, aroyl, heteroaroyl, alkoxycarbonyl, cyclyloxycarbonyl, aryloxycarbonyl or heteroaryloxycarbonyl, as defined herein and the other of $Y^1$ and $Y^2$ is as defined previously, or for where the substituent is $Y^1Y^2NC(O)$—, $Y^1Y^2NC(O)O$—, $Y^1Y^2NC(O)NY^3$— or $Y^1Y^2NSO_2$—, $Y^1$ and $Y^2$ may also be taken together with the N atom through which $Y^1$ and $Y^2$ are linked to form a 4 to 7 membered azaheterocyclyl or azaheterocyclenyl. When a ring system is saturated or partially saturated, the "ring group substituents" further include, methylene (H2C=), oxo (O=) and thioxo (S=). Acidic/amide ring group substituents are carboxy (acid). —C(O)—NHOH, —C(O)—CH$_2$OH, —C(O)—CH$_2$SH, —C(O)—NH—CN, sulfo, phosphono, alkylsulfonylcarbamoyl, tetrazolyl, arylsulfonylcarbamoyl, N-methoxycarbamoyl, heteroarylsulfonylcarbamoyl, 3-hydroxy-3-cyclobutene-1,2-dione, 3,5-dioxo-1,2,4-oxadiazolidinyl or hydroxyheteroaryl such as 3-hydroxyisoxazolyl, 3-hydroxy-1-methylpyrazoly and $Y^1Y^2NCO$—. Non-acidic polar ring group substituents are hydroxy, oxo (O=), thioxo (S=), acyl or its thioxo analogue, cyclylcarbonyl or its thioxo analogue, aroyl or its thioxo analogue, heteroaroyl or its thioxo analogue, alkoxycarbonyl, cyclyloxycarbonyl, aryloxycarbonyl, heteroaryloxycarbonyl, acyloxy, cyclylcarbonyloxy, aroyloxy, heteroaroyloxy, alkylsulfonyl, cyclylsulfonyl, arylsulfonyl, heteroarylsulfonyl, alkylsulfinyl, cyclylsulfinyl, arylsulfinyl, heteroarylsulfinyl, thiol, $Y^1Y^2N$—, $Y^1Y^2NC(O)$—, $Y^1Y^2NC(O)O$—, $Y^1Y^2NC(O)NY^3$— or $Y^1Y^2NSO_2$.

"Solvate" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, and the like.

EMBODIMENTS

With reference to inventions described herein, below are particular embodiments related thereto.

A particular embodiment according to the invention is wherein $R^1$ is optionally substituted phenyl($C_{1-3}$ alkyl) or optionally substituted phenylcyclopropyl.

Another particular embodiment according to the invention is wherein $R^1$ is optionally substituted phenyl($C_{1-3}$ alkyl).

Another particular embodiment according to the invention is wherein $R^1$ is optionally substituted phenyl($C_{2-3}$ alkyl).

Another particular embodiment according to the invention is wherein $R^1$ is optionally substituted phenyl(ethyl).

Another particular embodiment according to the invention is wherein $R^1$ is phenylethyl.

Another particular embodiment according to the invention is wherein $R^1$ is optionally substituted phenylcyclopropyl.

Another particular embodiment according to the invention is wherein the optionally substituted phenyl in $R^1$ is substituted by halo.

Another particular embodiment according to the invention is wherein the optionally substituted phenyl in $R^1$ is substituted by chloro or fluoro.

Another particular embodiment according to the invention is wherein the optionally substituted phenyl in $R^1$ is substituted by chloro or fluoro.

Another particular embodiment according to the invention is wherein the optionally substituted phenyl in $R^1$ is mono substituted by chloro or fluoro.

Another particular embodiment according to the invention is wherein the optionally substituted phenyl in $R^1$ is ortho mono substituted by chloro.

Another particular embodiment according to the invention is wherein the optionally substituted phenyl in $R^1$ is para mono substituted by chloro.

Another particular embodiment according to the invention is wherein the optionally substituted phenyl in $R^1$ is meta mono substituted by chloro.

Another particular embodiment according to the invention is wherein the optionally substituted phenyl in $R^1$ is para mono substituted by fluoro.

Another particular embodiment according to the invention is wherein the optionally substituted phenyl in $R^1$ is di substituted by chloro or fluoro.

Another particular embodiment according to the invention is wherein the optionally substituted phenyl in $R^1$ is ortho, para di substituted by chloro.

Another particular embodiment according to the invention is wherein the optionally substituted phenyl in $R^1$ is ortho, para di substituted by fluoro.

Another particular embodiment according to the invention is wherein $R^2$ is H or methyl.

Another particular embodiment according to the invention is wherein $R^2$ is H.

Another particular embodiment according to the invention is wherein $R^3$ is optionally substituted phenyl, optionally substituted thiazolyl, pyridyl, or thienyl.

Another particular embodiment according to the invention is wherein $R^3$ is optionally substituted indolidonyl.

Another particular embodiment according to the invention is wherein the optionally substituted phenyl in $R^3$ is substituted by halo, carboxy or alkoxycarbonyl.

Another particular embodiment according to the invention is wherein the optionally substituted phenyl in $R^3$ is mono substituted by chloro or fluoro.

Another particular embodiment according to the invention is wherein the optionally substituted phenyl in $R^3$ is ortho mono substituted by chloro.

Another particular embodiment according to the invention is wherein the optionally substituted phenyl in $R^3$ is para mono substituted by chloro.

Another particular embodiment according to the invention is wherein the optionally substituted phenyl in $R^3$ is meta mono substituted by chloro.

Another particular embodiment according to the invention is wherein the optionally substituted phenyl in $R^3$ is di substituted by fluoro.

Another particular embodiment according to the invention is wherein the optionally substituted phenyl in $R^3$ is ortho, para di substituted by fluoro.

Another particular embodiment according to the invention is wherein the optionally substituted phenyl in $R^3$ is substituted by carboxy or alkoxycarbonyl.

Another particular embodiment according to the invention is wherein the optionally substituted phenyl in $R^3$ is mono substituted by carboxy or alkoxycarbonyl.

Another particular embodiment according to the invention is wherein the optionally substituted phenyl in $R^3$ is meta mono substituted by carboxy or alkoxycarbonyl.

Another particular embodiment according to the invention is wherein the optionally substituted phenyl in $R^3$ is para mono substituted by carboxy or alkoxycarbonyl.

Another particular embodiment according to the invention is wherein the optionally substituted phenyl in $R^3$ is 2-thienyl Another particular embodiment according to the invention is wherein the optionally substituted phenyl in $R^3$ is 3-thienyl.

Another particular embodiment according to the invention is wherein the optionally substituted phenyl in $R^3$ is optionally substituted thiazolyl.

Another particular embodiment according to the invention is wherein the optionally substituted phenyl in $R^3$ is methyl substituted thiazolyl.

Another particular embodiment according to the invention is wherein $R^4$ is H.

Another particular embodiment according to the invention is wherein $R^5$ is JGZ.

Another particular embodiment according to the invention is wherein Z is a bond.

Another particular embodiment according to the invention is wherein Z is a CO.

Another particular embodiment according to the invention is wherein G is lower alkyl.

Another particular embodiment according to the invention is wherein G is $C_{1-3}$ lower alkyl.

Another particular embodiment according to the invention is wherein G is $C_{2-3}$ lower alkyl.

Another particular embodiment according to the invention is wherein J is $R^8R^7N$.

Another particular embodiment according to the invention is wherein $R^7$ and $R^8$ are H or lower alkyl.

Another particular embodiment according to the invention is wherein $R^7$ and $R^8$ are lower alkyl.

Another particular embodiment according to the invention is wherein $R^7$ and $R^8$ are $C_{1-2}$ lower alkyl.

Another particular embodiment according to the invention is wherein $R^7$ and $R^8$ are $C_1$ lower alkyl.

Another particular embodiment according to the invention is wherein one of $R^7$ and $R^8$ is H and the other of $R^7$ and $R^8$ is lower alkyl.

Another particular embodiment according to the invention is wherein $R^9$ and $R^{10}$ are H.

Another particular embodiment according to the invention is wherein $R^9$ and $R^{10}$ are lower alkyl.

Another particular embodiment according to the invention is wherein $R^9$ and $R^{10}$ are methyl.

Another particular embodiment according to the invention is wherein J is optionally (lower alkyl or halo) substituted 3-7 membered heterocyclyl.

Another particular embodiment according to the invention is wherein J is optionally (lower alkyl or halo) substituted 3-7 membered azaheterocyclyl.

Another particular embodiment according to the invention is wherein J as optionally (lower alkyl or halo) substituted 3-7 membered heterocyclyl is N-methyl piperidin-4-yl.

Another particular embodiment according to the invention is wherein $R^5$ is $R^8R^7NQ^1$ lower alkyl.

Another particular embodiment according to the invention is wherein $Q^1$ is carbonyl.

Another particular embodiment according to the invention is wherein $Q^1$ is carbonyl and J is $R^8R^7N$ or optionally (lower alkyl or halo) substituted 3-7 membered azaheterocyclyl.

Another particular embodiment according to the invention is wherein Y is CO.

Another particular embodiment according to the invention is wherein Y is $SO_2$.

Another particular embodiment according to the invention is wherein A and $R^5$ taken together form a 4-6 membered spiro azaheterocyclyl of the following formula

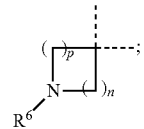

n and p are independently 0, 1, 2, 3, 4, or 5 so long as n and $p \geq 2$ but $\leq 5$.

Another particular embodiment according to the invention is wherein A and $R^5$ taken together form azetidine, pyrrolidine or piperidine, each of which is optionally N-substituted by lower alkyl.

Another preferred embodiment of the invention is a compound selected from the group of the following formulae:

-continued
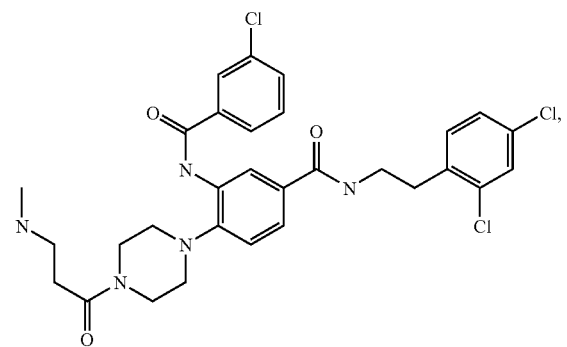
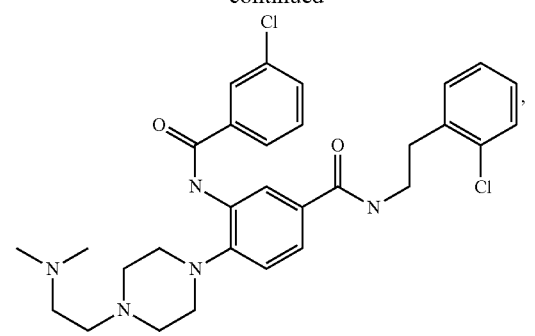
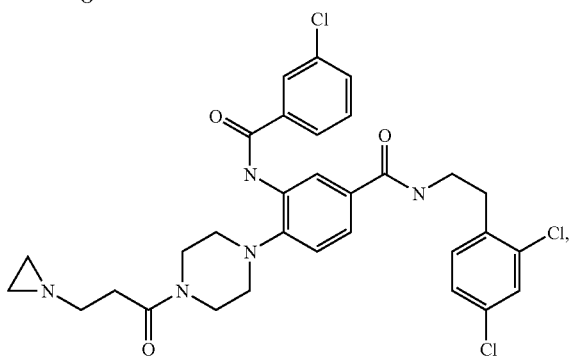
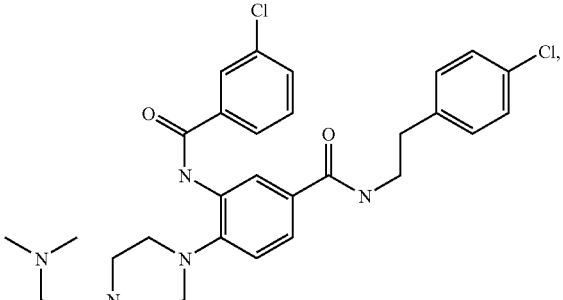
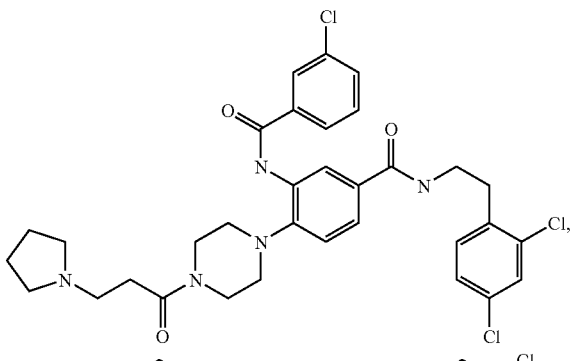
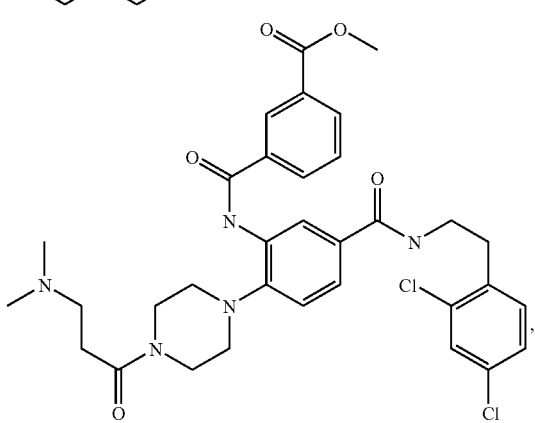
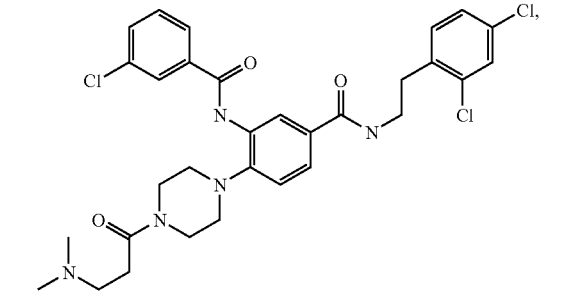
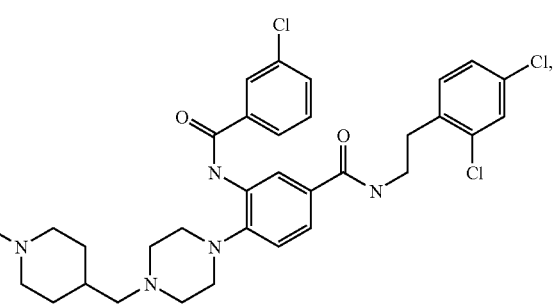
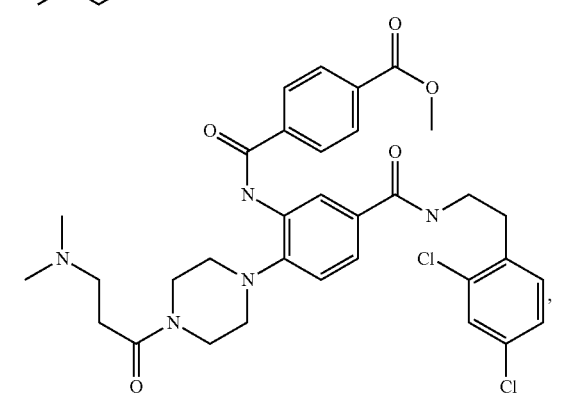
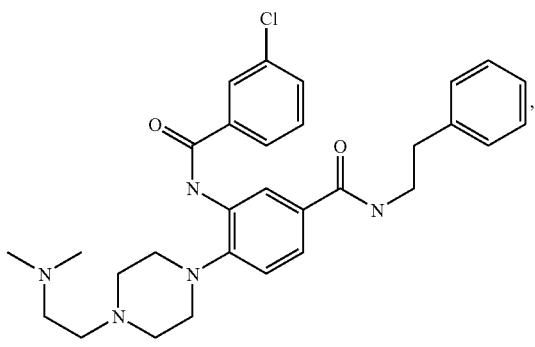

25
-continued
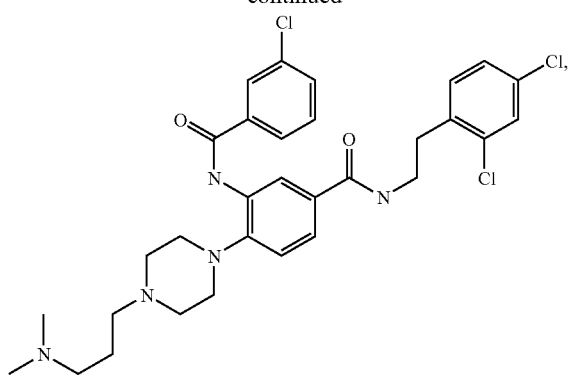
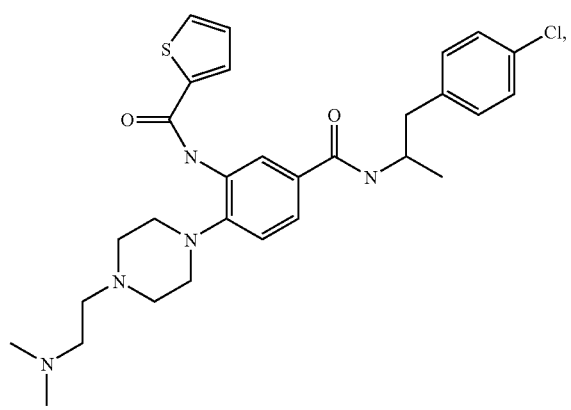
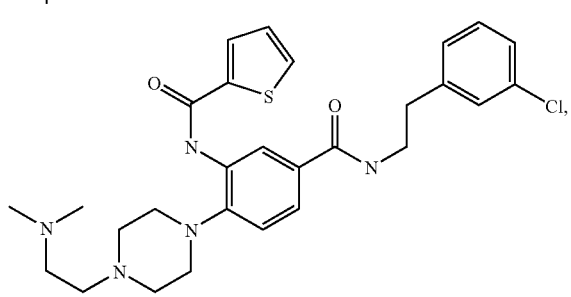
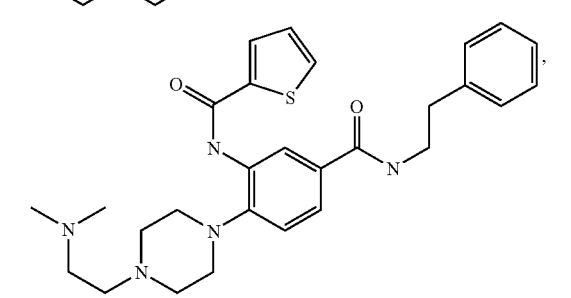
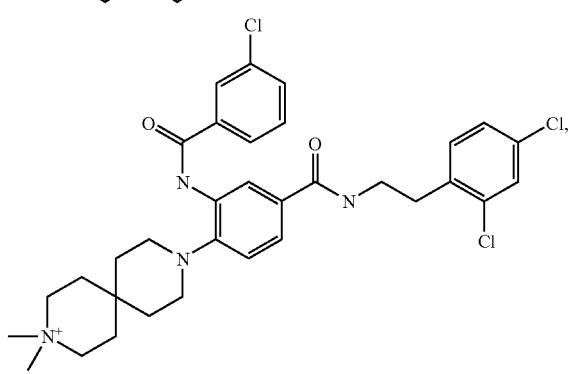
26
-continued
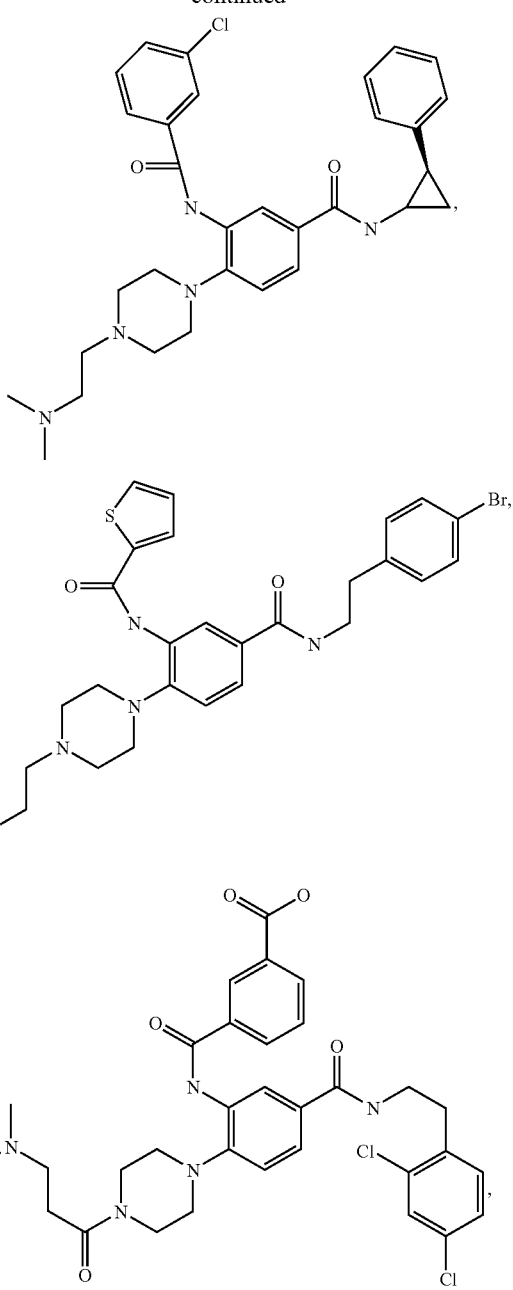
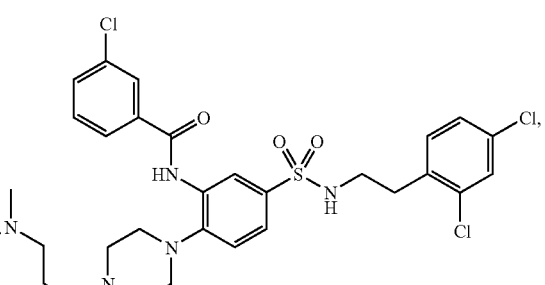

-continued

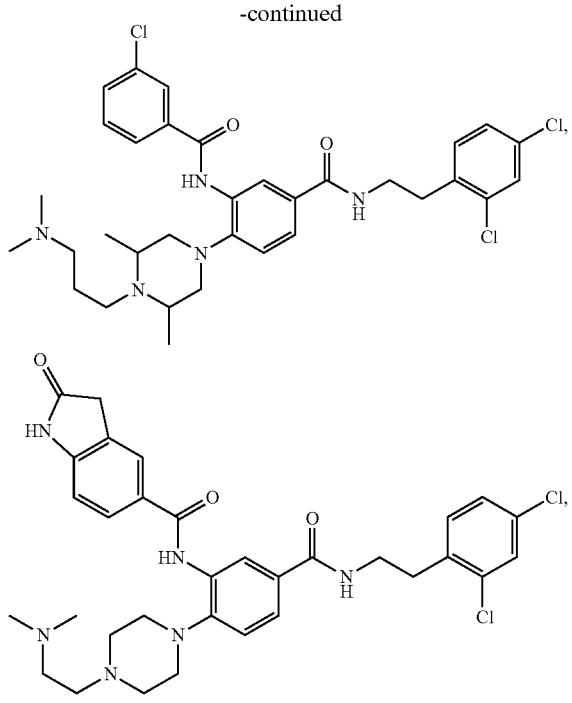

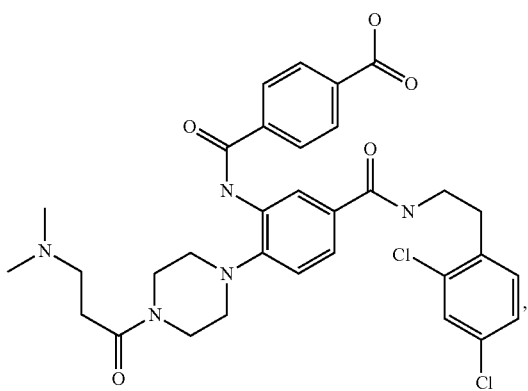

or pharmaceutically acceptable salt or prodrug thereof, or a solvate of such a compound, its salt or its prodrug.

The compounds of the invention optionally are supplied as salts. Those salts that are pharmaceutically acceptable are of particular interest since they are useful in administering the foregoing compounds for medical purposes. Salts that are not pharmaceutically acceptable are useful in manufacturing processes, for isolation and purification purposes, and in some instances, for use in separating stereoisomeric forms of the compounds of this invention. The latter is particularly true of amine salts prepared from optically active amines.

Acid addition salts are formed with the compounds of the invention in which a basic function such as an imino nitrogen, amino or mono or disubstituted group is present. A particular acid addition salt is the pharmaceutically acceptable acid addition salt, i.e., a salt whose anion is non-toxic to a patient in a pharmaceutical dose of the salt, so that the beneficial effects inherent in the free acid are not initiated by side effects ascribable to the anion. The salts chosen are chosen optimally to be compatible with the customary pharmaceutical vehicles and adapted for oral or parenteral administration. Acid addition salts of the compounds of this invention may be prepared by reaction of the free base with the appropriate acid, by the application or adaptation of known methods. For example, the acid addition salts of the compounds of this invention may be prepared either by dissolving the fee base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution. Some suitable acids for use in the preparation of such salts are hydrochloric acid, hydrobromic acid, phosphoric acid, sulfuric acid, various organic carboxylic and sulfonic acids, such as acetic acid, citric acid, propionic acid, succinic acid, benzoic acid, tartaric acid, fumaric acid, mandelic acid, ascorbic acid, malic acid, methanesulfonic acid, toluenesulfonic acid, fatty acid, mandelic acid, ascorbic acid, malic acid, methanesulfonic acid, toluenesulfonic acid, fatty acids, adipate alginate, ascorbate, aspartate, benzenesulfonate, benzoate, cyclopentanepropionate, digluconate, dodecylsulfate, bisulfate, butyrate, lactate, laurate, lauryl sulfate, maleate, hydroiodide, 2-hydroxyethanesulfonate, glycerophosphate, picrate, pivalate, pamoate, pectinate, persulfate, 3-phenylpropionate, thiocyanate, 2-naphthalenesulfonate, undecanoate, nicotinate, hemisulfate, heptonate, hexanoate, camphorate, camphorsulfonate, and others.

The acid addition salts of the compounds of this invention can be regenerated from the salts by the application or adaptation of known methods. For example, parent compounds of the invention can be regenerated from their acid addition salts by treatment with an alkali, e.g., aqueous sodium bicarbonate solution or aqueous ammonia solution.

Base addition salts may be formed where the compound of the invention contains a carboxy group, or a sufficiently acidic bioisostere. The bases which can be used to prepare the base addition salts include preferably those which produce, when combined with the free acid, pharmaceutically acceptable salt, i.e., salt whose cation is non-toxic to a patient in a pharmaceutical dose of the salt, so that the beneficial effects inherent in the free base are not vitiated by side effects ascribable to the cation.

Pharmaceutically acceptable salts, including those derived from alkali and alkaline earth metal salts within the scope of the invention include those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline. N,N'-dibenzylethylenediamine, chloroprocaine, diethanolamine, procaine, N-benzylphenethylamine, diethylamine, piperazine, tris(hydroxymethyl)-aminomethane. tetramethylammonium hydroxide, and the like.

Compounds of this invention can be regenerated from their base addition salts by the application or adaptation of known methods. For example, parent compounds of the invention can be regenerated from their base addition salts by treatment with an acid, e.g., hydrochloric acid.

Compounds of the present invention may be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Compounds of formula 1 may be prepared by the application or adaptation of known methods as used heretofore or described in the literature, or by methods according to this invention herein.

It is a further object of the invention to provide a method for preparing an intermediate compound that is useful in preparing the compound of formula 1.

Preparation of Compounds of the Invention

The starting materials and intermediates of compounds of the invention may be prepared by the application or adaptation of known methods, for example methods as described in the Reference Examples or their obvious chemical equivalents.

Compounds of the invention may be prepared by the application or adaptation of known methods, by which is meant methods used heretofore or described in the literature, for example those described by R. C. Larock in Comprehensive Organic Transformations, VCH publishers (1989).

Experimental Part

General Procedures

Starting materials used in the synthesis are obtained from chemical vendors such as Aldrich, Acros, Sigma, Fluka, Nova Biochem, Advanced Chemtech, Bachem, Lancaster and others.

General solid-phase synthesis methodology is used to produce the compounds of the invention. Such methods are described, for example, by Steward and Young, Solid Phase Peptide Synthesis (Freeman & Co., San Francisco, 1969), which is incorporated herein by reference. Occasionally traditional solution phase synthesis is used as well.

Unless indicated otherwise, compounds are synthesized using FMPE polystyrene HL Resin (01-64-0254 or 01-64-0399 (NovaBiochem, EMD Biosciences, Inc.). The resin contains the 'Ameba' linker. This type of linkage can be introduced to any type of amino polystyrene resin by procedure described by E. Hernandez, et al. Tetrahedron Lett. 2002, 43, 4741, and D. Weber et al. J. Peptide Sci. 2002, 8, 461 and is incorporated herein.

In the first step of the synthesis (for general synthetic scheme, see FIG. 1), resin is

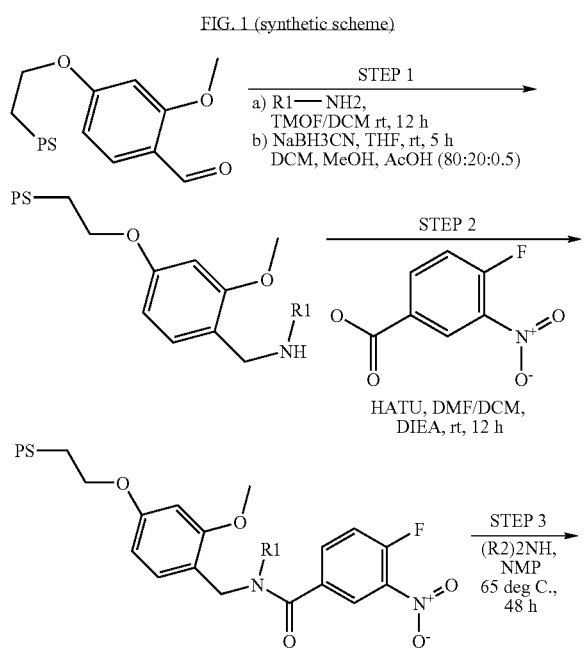

FIG. 1 (synthetic scheme)

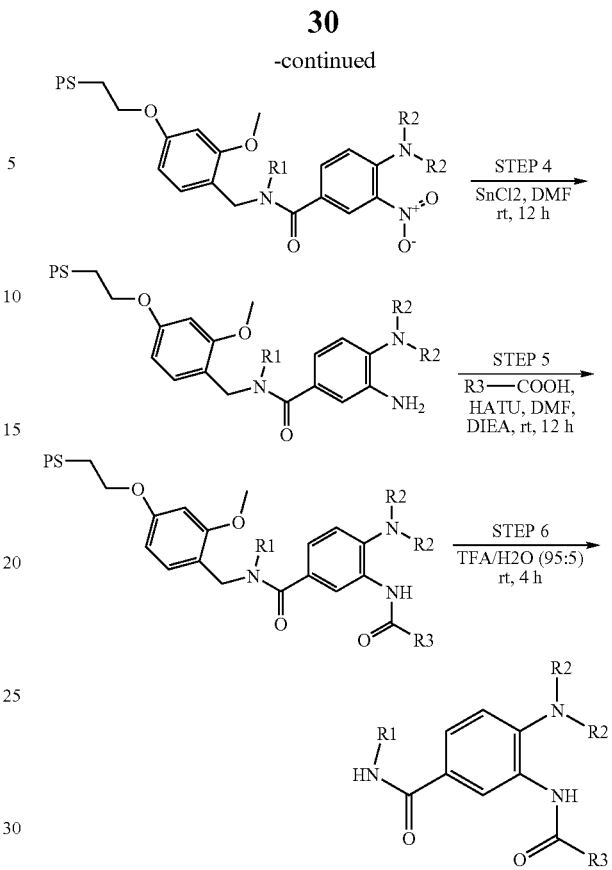

treated with 0.5M solution of an amine in DCM/TMOF (1:1) 12 h at ambient temperature to create the Schiff base. After 2 washes using THF, reduction of the Schiff base is achieved via treatment of resin with mixture of 1 part of 1 M NaBH$_3$CN in THF and 3 parts of THF:MeOH:AcOH (80:20:0.5) at ambient temperature for 5 h. The resin is washed ending up swollen in DMF.

To the resulting secondary amine on the resin, 4-fluoro-3-nitro benzoic acid is coupled (see scheme 1). Coupling is performed using DIC/HOAt or HATU/DIEA, usually in DMF/DCM mixture (1:1). This coupling is done at ambient temperature (RT) for 12 h. The resin is washed several times using a sequence of solvents including such as DMF, THF, AN ending up swollen in DMF.

Fluorine substitution is accomplished via treatment of resin using 0.5M solution of particular secondary amine in NMP for 48 h at 65° C. The resin is washed several times using a sequence of solvents including such as DMF, THF, AN ending up swollen in DMF.

The nitro group is reduced via treatment of resin with 1 M solution of SnCl$_2$ as in example 12 in DMF at ambient temperature for 12 h. The resin is washed several times using a sequence of solvents including such as DMF, THF, AN ending up swollen in DMF.

Final acylation of anilinic nitrogen is accomplished via HATU coupling of acid in DMF overnight (12 h) at ambient temperature using DIEA as base.

After completion of the compound precursor assembly on the resin, the resin is then washed several times using a sequence of solvents including such as DMF, THF, AN ending up swollen in THF and dried in vacuum.-

Cleavage is achieved via treatment of resin with 95:5 mixture of TFA and water at ambient temperature for 4 h. Resin is then extracted 3× by the same mixture and combined extracts evaporated to the oily residue.

If modifications of piperazine substructure are necessary, appropriate reactions are performed on resin in stage of 'nitro' construct attached (described vide supra for each compound).

It will be appreciated that compounds of the present invention may contain asymmetric centers. These asymmetric centers may independently be in either the R or S configuration. It is to be understood that the present invention includes individual stereoisomers and mixtures thereof, including racemic mixtures, of compounds according to the invention. Such isomers can be separated from their mixtures, by the application or adaptation of known methods, for example chromatographic techniques and recrystallization techniques, or they are separately prepared from the appropriate isomers of their intermediates.

For the purpose herein it is understood that where appropriate tautomeric forms are included in the recitation of a given group, e.g., thioxo/mercapto or oxo/hydroxyl.

The dried compound is subjected to purification where two systems are used alternatively as needed. Referring to RP-HPLC Beckman system means using an appropriate gradient of 0.1% TFA in water and acetonitrile (AN) on system consisting of Beckman 125P Solvent Deliver System, Beckamn 166 Programmable Detector Module controlled by Data Station with Gold Nouveau software and YMC ODS-AM 20×250 mm column (S-5 (5 um), YMC, Inc. Wilmington, N.C., USA) at 270 nm (if not specified otherwise) and flow rate 10 ml/min. Referring to Waters mass-triggered-LCMS purification means using an appropriate gradient of 0.1% TFA in water and acetonitrile (AN) on Waters 2525 gradient solvent delivery system coupled with Waters-Micromass ZQ, and Waters 2487 UV detector at 220 nm (if not specified otherwise), controlled by MassLynx software data station. YMC ODS-AM 20×50 mm column (S-5 (5 um), YMC, Inc. Wilmington, N.C., USA) is used at flow rate 32 ml/min. After collecting the peak containing the intended synthetic product, the compound solution is lyophilized and the compound is subjected to an identification process, which included electrospray mass spectrum (LC/MS) and/or NMR analysis to confirm that the correct compound is synthesized.

Analytical LC/MS is performed using PE Sciex API 150EX with Sciex MassChrom software and equiped with Gilson 215 liquid handler, two Shimadzu LC-10AD liquid modules, Shimadzu SPD-10A detector, Keystone Betasil C-18 column (2×30 mm, 3 um, flow 0.7 ml/min of acetonitrile/water/0.1% TFA gradient) in ES+mode.

For structural confirmation NMR spectra are measured for some compounds. Referring to NMR, spectra are collected on two alternative instruments which are used respectively as needed. Bruker 300 MHz means Bruker Avance DPX 300 MHz instrument, Bruker 600 MHz means Bruker Avance DPX 600 MHz instrument. Samples are measured in DMSO-$d_6$ (Aldrich) or in $CDCl_3$ (Aldrich) respectively as solvents.

The starting materials, intermediates and products may be prepared by the application or adaptation of known methods, or example methods as described in the Examples or their obvious chemical equivalents.

EXAMPLE 1

Solution Phase Precursor Preparations

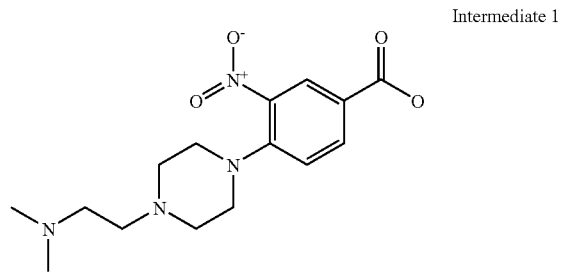

Intermediate 1

Step 1: 3.7 g of 4-fluoro-3-nitro benzoic acid is treated with 1 M solution of 4-(dimethylaminoethyl)-piperazine in DMF for 120 min at 100° C. The reaction mixture is first checked by LCMS, then partially evaporated and crystallized from AN. Pure product (3 g) is obtained.

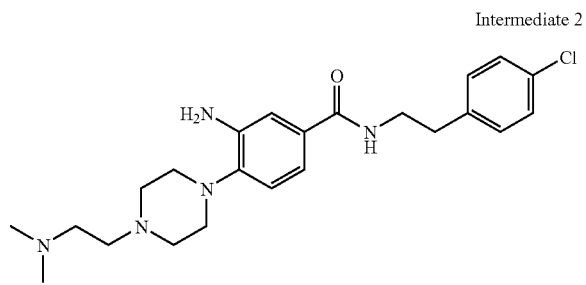

Intermediate 2

Step 2: 322 mg (1 mmol) of product from the previous reaction is dissolved in 5 ml of DMF, together with 139 mg (1.1 mmol) of DIC and 459 mg (=3 mmol) of HOBt and 171 mg (1.1 mmol) of 4-chloro-phenethyl amine. After 2 h at ambient temperature ⅔ of solvent is evaporated, and oily residue is purified via several injections using Waters mass-triggered-LCMS purification system. Proper fractions are lyophilized to yield of 115 mg of desired material.

Step 3: 100 mg of the product from the previous reaction is dissolved in 8 mL of methanol and 100 mg of 5% Pd/C added. After evacuation in a Parr apparatus, 35 psi of hydrogen is introduced. The reaction is shaken 12 h at ambient temperature. Analytical LCMS shows product and side product of dehalogenation. Catalyst is filtered off via 5 μm frit filtration and methanol evaporated on ROTAVAP. Using Waters mass-triggered-LCMS purification system two main fractions are obtained, which after lyophilization yields desired product and as side product a dehalogenated compound.

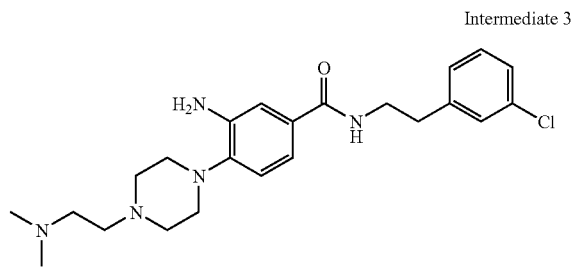

Intermediate 3

Step 2: 322 mg (1 mmol) of the product from the previous reaction is dissolved in 5 ml of DMF, together with 139 mg (1.1 mmol) of DIC and 459 mg (=3 mmol) of HOBt and 171 mg (1.1 mmol) of 3-chloro-phenethyl amine. After 2 h at ambient temperature ⅔ of solvent is evaporated, and oily residue is purified via several injections using Waters mass-triggered-LCMS purification system. Proper fractions are lyophilized to yield of 115 mg of desired material.

Step 3: 100 mg of the product from the previous reaction is dissolved in 8 mL of methanol and 100 mg of 5% Pd/C added. After evacuation in a Parr apparatus, 35 psi of hydrogen is introduced. The reaction is shaken for 2 h at ambient temperature. Analytical LCMS shows product and side product of dehalogenation. Catalyst is filtered off via fit filtration and methanol evaporated on ROTAVAP. Using Waters mass-triggered-LCMS purification system provided main fraction, which after lyophilization gave desired product.

Intermediate 4

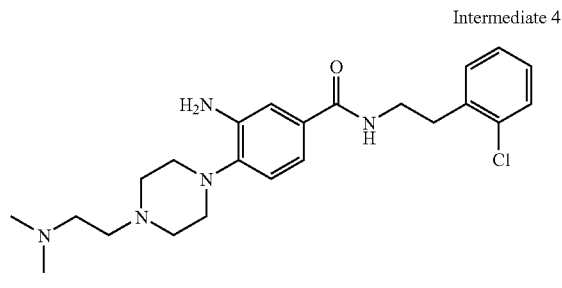

Step 2: 322 mg (1 mmol) of the product from the previous reaction is dissolved in 5 ml of DMF, together with 139 mg (1.1 mmol) of DIC and 459 mg (=3 mmol) of HOBt and 171 mg (1.1 mmol) of 2-chloro-phenethyl amine. After 2 h at ambient temperature ⅔ of solvent is evaporated, and an oily residue is purified via several injections using Waters mass-triggered-LCMS purification system. Proper fractions are lyophilized to yield of 115 mg of desired material.

Step 3: 100 mg of the product from the previous reaction is dissolved in 8 mL of methanol and 100 mg of 5% Pd/C added. After evacuation in Parr apparatus, 35 psi of hydrogen introduced. The reaction is shaken 2 h at ambient temperature. Analytical LCMS shows product and side product of dehalogenation. Catalyst is filtered off via frit filtration and methanol evaporated on ROTAVAP. Using Waters mass-triggered-LCMS purification system provided main fraction, which after lyophilization gave desired product.

EXAMPLE 2

N-{5-[2-(4-Chloro-phenyl)-ethylcarbamoyl]-2-[4-(2-dimethylamino-ethyl)-piperazin-1-yl]-phenyl}-isonicotinamide

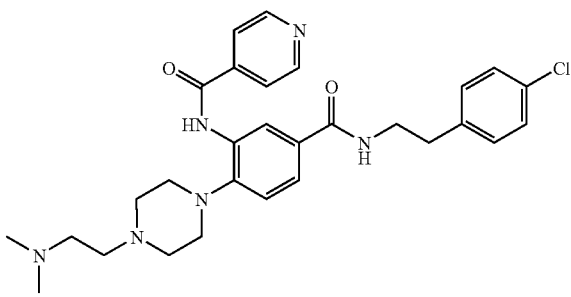

Starting from intermediate 2 HATU mediated coupling where 22 mg (0.05 mmol) of starting material, 0.15 mmol (57 mg) of HATU, 0.15 mmol (19 mg) of isonicotinic acid, and 0.3 mmol (39 mg=44 µL) of DIEA at ambient temperature is reacted for 3 h. LCMS check shows desired product, which is isolated after partial evaporation via Waters mass-triggered-LCMS purification system. Lyophilization yields desired product. MW=534.25 Da (calc. monoisotopic for $C_{29}H_{35}ClN_6O_2$), measured $(M+H)^+$=535.3 Da with appropriate Cl-isotope pattern, UV {220} based purity 83.7%.

EXAMPLE 3

N-{5-[2-(3-Chloro-phenyl)-ethylcarbamoyl]-2-[4-(2-dimethylamino-ethyl)-piperazin-1-yl]-phenyl}-isonicotinamide

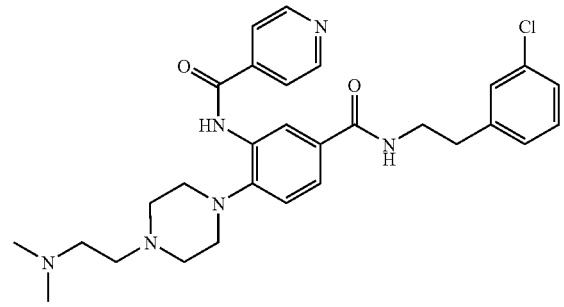

Starting from intermediate 3 HATU mediated coupling where 22 mg (0.05 mmol) of starting material, 0.15 mmol (57 mg) of HATU, 0.15 mmol (19 mg) of isonicotinic acid, and 0.3 mmol (39 mg=44 µL) of DIEA at ambient temperature is reacted for 3 h. LCMS check shows desired product, which is isolated after partial evaporation via Waters mass-triggered-LCMS purification system. Lyophilization yields desired product. MW=534.25 Da (calc. monoisotopic for $C_{29}H_{35}ClN_6O_2$), measured $(M+H)^+$=535.3 Da with appropriate Cl-isotope pattern, UV {220} based purity 90.9%.

EXAMPLE 4

N-{5-[2-(2-Chloro-phenyl)-ethylcarbamoyl]-2-[4-(2-dimethylamino-ethyl)-piperazin-1-yl]-phenyl}-isonicotinamide

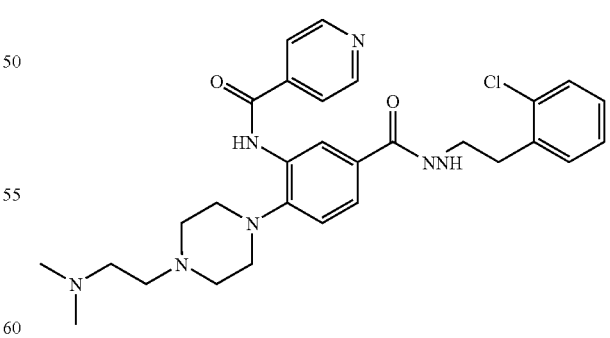

Starting from intermediate 4 HATU mediated coupling where 22 mg (0.05 mmol) of starting material, 0.15 mmol (57 mg) of HATU, 0.15 mmol (19 mg) of isonicotinic acid, and 0.3 mmol (39 mg=44 µL) of DIEA at ambient temperature is reacted for 3 h. LCMS check shows desired product, which is isolated after partial evaporation via Waters mass-triggered- LCMS purification system. Lyophilization yields desired product. MW=534.25 Da (calc. monoisotopic for $C_{29}H_{35}ClN_6O_2$), measured (M+H)$^+$=535.3 Da with appropriate Cl-isotope pattern, UV {220} based purity 100%.

EXAMPLE 5

Thiophene-2-carboxylic acid {2-[4-(2-dimethylamino-ethyl)-piperazin-1-yl]-5-[2-(2-chloro-phenyl)-ethylcarbamoyl]-phenyl}-amide

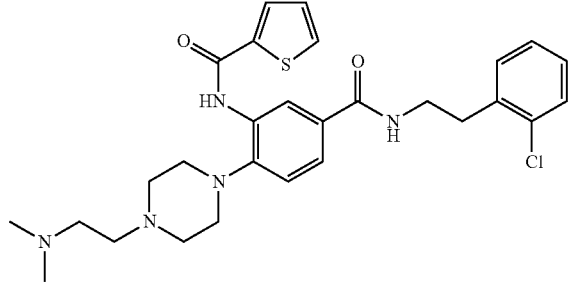

Starting from intermediate 4 HATU mediated coupling where 22 mg (0.05 mmol) of starting material, 0.15 mmol (57 mg) of HATU, 0.15 mmol (19 mg) of thiophene-2-carboxylic acid, and 0.3 mmol (39 mg=44 µL) of DIEA at ambient temperature is reacted for 3 h. LCMS check shows desired product, which is isolated after partial evaporation via Waters mass-triggered-LCMS purification system. Lyophilization yields desired product. MW=539.21 Da (calc. monoisotopic for $C_{28}H_{34}ClN_5O_2S$), measured (M+H)$^+$=540.2 Da with appropriate Cl-isotope pattern, UV {220} based purity 97.6%.

EXAMPLE 7

Thiophene-2-carboxylic acid {2-[4-(2-dimethylamino-ethyl)-piperazin-1-yl]-5-[2-(3-chloro-phenyl)-ethylcarbamoyl]-phenyl}-amide

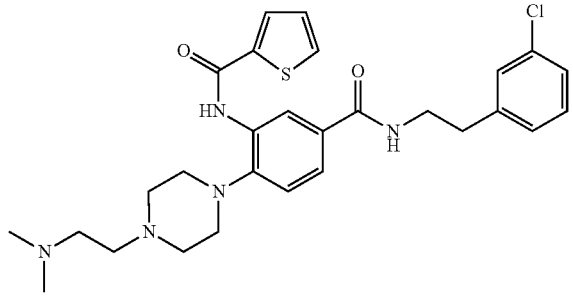

Starting from intermediate 3 HATU mediated coupling where 22 mg (0.05 mmol) of starting material, 0.15 mmol (57 mg) of HATU, 0.15 mmol (19 mg) of thiophene-2-carboxylic acid, and 0.3 mmol (39 mg=44 µL) of DIEA at ambient temperature is reacted for 3 h. LCMS check shows desired product, which is isolated after partial evaporation via Waters mass-triggered-LCMS purification system. Lyophilization yields desired product. MW=539.21 Da (calc. monoisotopic for $C_{28}H_{34}ClN_5O_2S$), measured (M+H)$^+$=540.2 Da with appropriate Cl-isotope pattern, UV {220} based purity 97.1%.

EXAMPLE 8

Thiophene-2-carboxylic acid {2-[4-(2-dimethylamino-ethyl)-piperazin-1-yl]-5-[2-(4-chloro-phenyl)-ethylcarbamoyl]-phenyl}-amide

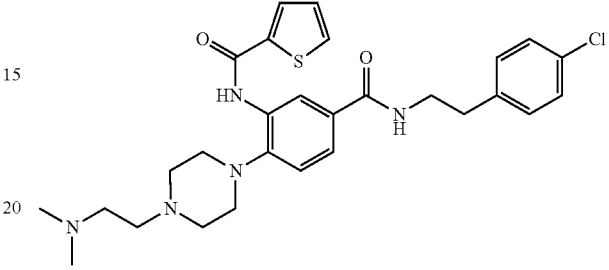

Starting from intermediate 2 HATU mediated coupling where 22 mg (0.05 mmol) of starting material, 0.15 mmol (57 mg) of HATU, 0.15 mmol (19 mg) of thiophene-2-carboxylic acid, and 0.3 mmol (39 mg=44 µL) of DIEA at ambient temperature is reacted for 3 h. LCMS check shows desired product, which is isolated after partial evaporation via Waters mass-triggered-LCMS purification system. Lyophilization yields desired product. MW=539.21 Da (calc. monoisotopic for $C_{28}H_{34}ClN_5O_2S$), measured (M+H)$^+$=540.2 Da with appropriate Cl-isotope pattern, UV {220} based purity 76.9%.

EXAMPLE 9

3-(3-Chloro-benzoylamino)-N-[2-(2-chloro-phenyl)-ethyl]-4-[4-(2-di methylamino-ethyl)-piperazin-1-yl]-benzamide

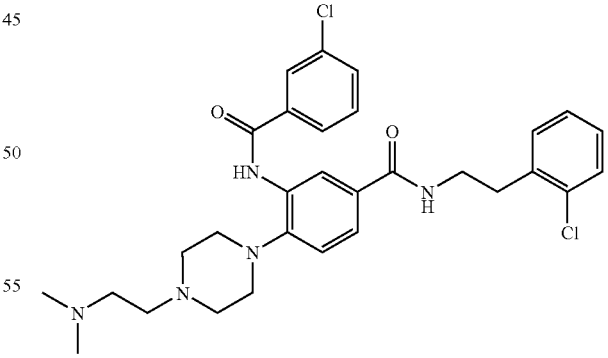

Starting from intermediate 4 HATU mediated coupling where 22 mg (0.05 mmol) of starting material, 0.15 mmol (57 mg) of HATU, 0.15 mmol (24 mg) of 3-chloro benzoic acid, and 0.3 mmol (39 mg=44 µL) of DIEA at ambient temperature is reacted for 3 h. LCMS check shows desired product, which is isolated after partial evaporation via Waters mass-triggered-LCMS purification system. Lyophilization yields desired product. MW=567.22 Da (calc. monoisotopic for $C_{30}H_{35}Cl_2N_5O_2$), measured (M+H)$^+$=568.2 Da with appropriate Cl-isotope pattern, UV {220} based purity 62.4%.

EXAMPLE 10

3-(3-Chloro-benzoylamino)-N-[2-(3-chloro-phenyl)-ethyl]-4-[4-(2-di methylamino-ethyl)-piperazin-1-yl]-benzamide

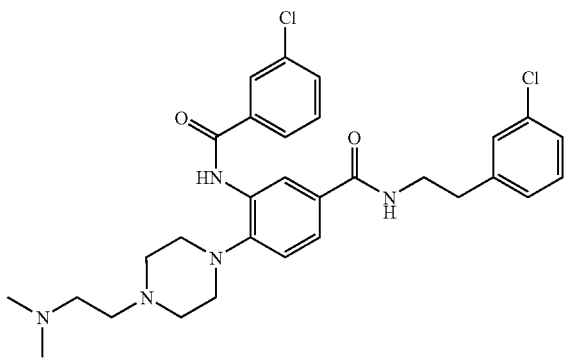

Starting from intermediate 3 HATU mediated coupling where 22 mg (0.05 mmol) of starting material, 0.15 mmol (57 mg) of HATU, 0.15 mmol (24 mg) of 3-chloro benzoic acid, and 0.3 mmol (39 mg=44 µL) of DIEA at ambient temperature is reacted for 3 h. LCMS check shows desired product, which is isolated after partial evaporation via Waters mass-triggered-LCMS purification system. Lyophilization yields desired product. MW=567.22 Da (calc. monoisotopic for $C_{30}H_{35}Cl_2N_5O_2$), measured (M+H)$^+$=568.2Da with appropriate Cl-isotope pattern, UV {220} based purity 54.5%.

EXAMPLE 11

3-(3-Chloro-benzoylamino)-N-[2-(4-chloro-phenyl)-ethyl]-4-[4-(2-di methylamino-ethyl)-piperazin-1-yl]-benzamide

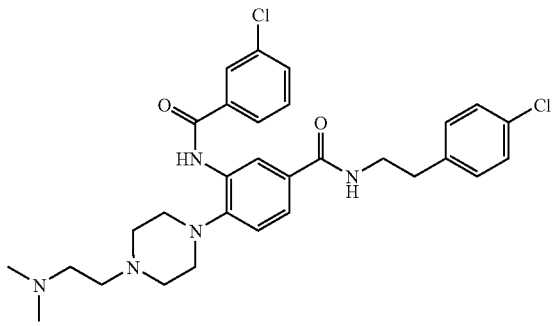

Starting from intermediate 2 HATU mediated coupling where 22 mg (0.05 mmol) of starting material, 0.15 mmol (57 mg) of HATU, 0.15 mmol (24 mg) of 3-chloro benzoic acid, and 0.3 mmol (39 mg=44 µL) of DIEA at ambient temperature is reacted for 3 h. LCMS check shows desired product, which is isolated after partial evaporation via Waters mass-triggered-LCMS purification system. Lyophilization yields desired product. MW=567.22 Da (calc. monoisotopic for $C_{30}H_{35}Cl_2N_5O_2$), measured (M+H)$^+$=568.2 Da with appropriate Cl-isotope pattern, UV {220} based purity 88.5%.

EXAMPLE 12

3-(3-Chloro-benzoylamino)-N-[2-(2,4-dichloro-phenyl)-ethyl]-4-[4-(2-di methylamino-ethyl)-piperazin-1-yl]-benzamide

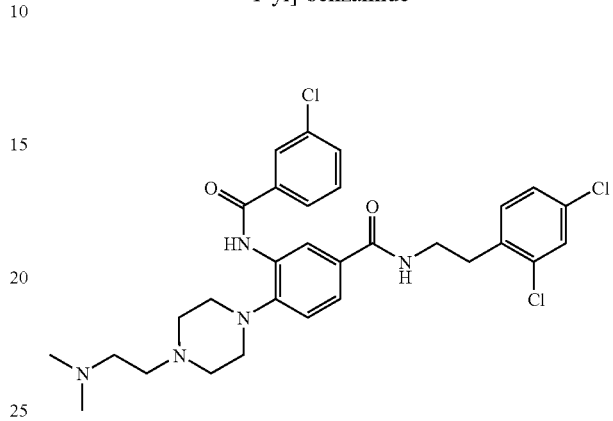

Step 1 : 0.2 g of FMPE polystyrene HL Resin cat #01-64-0254 (NovaBiochem—'Ameba' S=1.54 mmol/g, EMD Biosciences, Inc.) in 10 mL syringe is swollen in DCM for 60 min, then the resin is treated with 1 mL of 0.4M solution (2 mmol) of 2,4-dichloro-phenethyl amine in DCM/TMOF (1:1) 12 h at ambient temperature to create the Schiff base. After 2 quick washes using THF, reduction of the Schiff base is achieved via treatment of resin with NaBH(OAc)$_3$ which is added as solid (5 eq.) and then shaken at ambient temperature for 16 h. The resin is washed 1×MeOH, 2× by DMF, 2×MeOH, 5×DCM, and 5×DMF.

Step 2: To the resin, is added a solution of 185 mg (1 mmol) 4-fluoro-3-nitro benzoic acid, 1 mmol (380 mg) of HOAt, 1 mmol (126 mg) DIC in 4 ml DMF/DCM mixture (1:1). This coupling is done at ambient temperature (RT) for 12 h. The resin is washed 3×DMF, 2×DCM, 2×DMF, (ending up with swollen resin in DMF).

Step 3: Fluorine substitution is accomplished via treatment of resin using 3 ml of 0.5M solution of 4-[2-(N,N-dimethylamino]-ethyl]-piperazine in NMP for 48 h at 65° C. The resin is washed 3×DMF, 2×DCM, 2×DMF, (ending up with swollen resin in DMF).

Step 4: The nitro group is reduced via treatment of resin with 1 M solution of SnCl$_2$ in DMF at ambient temperature for 12 h. The resin is washed 3×DMF, 2×DCM, 2×DMF, (ending up with swollen resin in DMF).

Step 5: To the resin, is added a solution of 156 mg (1 mmol) 3-chloro benzoic acid, 1 mmol (380 mg) of HATU, and 3 mmol (385 mg=420 µL) of DIEA in 2 mL of DMF. This coupling is done at ambient temperature (RT) for 12 h. The resin is washed 3×DMF, 3×DCM, and dried in vacuum.

For cleavage, 1.5 ml of mixture TFA/water 95:5 are added to the dry resin and shaken at room temperature for 4 h. The resin is filtered off, washed with mixture AN and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=601.18 Da

EXAMPLE 13

3-(3-Chloro-benzoylamino)-N-[2-(2,4-dichloro-phenyl)-ethyl]-4-[4-(3-di methylamino-propyl)-piperazin-1-yl]-benzamide

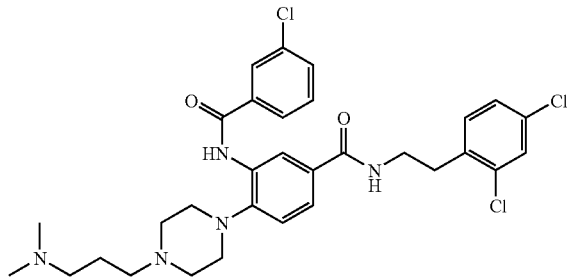

Step 1: Is undertaken as in example 12
Step 2: Is undertaken as in example 12
Step 3: Fluorine substitution is accomplished via treatment of resin using 3 ml 0.5M solution of 4-[2-(N,N-dimethylamino]-propyl]-piperazine in NMP for 48 h at 65° C. The resin is washed 3×DMF, 2×DCM, 2×DMF, (ending up with swollen resin in DMF).
Step 4: The nitro group is reduced via treatment of resin with 1 M solution of SnCl$_2$ as in example 12 in DMF at ambient temperature for 12 h. The resin is washed 3×DMF, 2×DCM, 2×DMF, (ending up with swollen resin in DMF).
Step 5: To the resin, is added a solution of 156 mg (1 mmol) 3-chloro benzoic acid, 1 mmol (380 mg) of HATU, and 3 mmol (385 mg=420 µL) of DIEA in 2 mL of DMF. This coupling is done at ambient temperature (RT) for 12 h. The resin is washed 3×DMF, 3×DCM, and dried in vacuum.

For cleavage, 1.5 ml of mixture TFA/water 95:5 are added to the dry resin and shaken at room temperature for 4 h. The resin is filtered off, washed with mixture AN and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=615.19 Da (calc. monoisotopic for $C_{31}H_{36}Cl_3N_5O_2$), measured $(M+H)^+$= 616.2 Da with appropriate Cl-isotope pattern, UV {220} based purity 93.1%.

EXAMPLE 14

4-[4-(2-Amino-ethyl)-piperazin-1-yl]-3-(3-chlorobenzoylamino)-N-[2-(2,4-dichloro-phenyl)-ethyl] benzamide

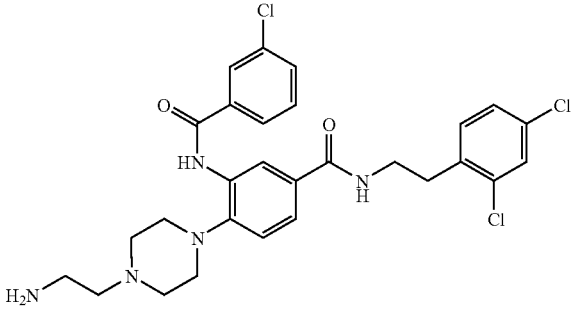

Step 1: Is undertaken as in example 12
Step 2: Is undertaken as in example 12
Step 3: Fluorine substitution is accomplished via treatment of resin using 0.5M solution of boc-4-(2-amino-ethyl)-piperazine in NMP for 48 h at 65° C. The resin is washed 3×DMF, 2×DCM, 2×DMF, (ending up with swollen resin in DMF).
Step 4: The nitro group is reduced via treatment of resin with 1 M solution of SnCl$_2$ as in example 12 in DMF at ambient temperature for 12 h. The resin is washed 3×DMF, 2×DCM, 2×DMF, (ending up with swollen resin in DMF).
Step 5: To the resin, is added a solution of 156 mg (1 mmol) 3-chloro benzoic acid, 1 mmol (380 mg) of HATU, and 3 mmol (385 mg=420 µL) of DIEA in 2 mL of DMF. This coupling is done at ambient temperature (RT) for 12 h. The resin is washed 3×DMF, 3×DCM, and dried in vacuum.

For cleavage, 1.5 ml of mixture TFA/water 95:5 are added to the dry resin and shaken at room temperature for 4 h. The resin is filtered off, washed with mixture AN and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=573.15 Da (calc. monoisotopic for $C_{28}H_{30}Cl_3N_5O_2$), measured $(M+H)^+$= 574.1 Da with appropriate Cl-isotope pattern, UV {220} based purity 67.7%.

EXAMPLE 15

3-(3-Chloro-benzoylamino)-N-[2-(2,4-dichloro-phenyl)-ethyl]-4-[4-(2-hydroxy-ethyl)-piperazin-1-yl]-benzamide

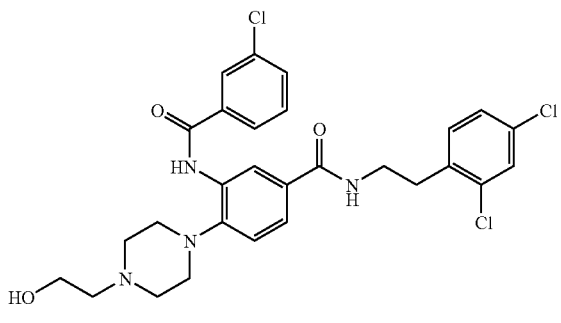

Step 1: Is undertaken as in example 12
Step 2: Is undertaken as in example 12
Step 3: Fluorine substitution is accomplished via treatment of resin using 0.5M solution of 2-(2-piperazin-1-yl)-ethanol in NMP for 48 h at 65° C. The resin is washed 3×DMF, 2×DCM, 2×DMF, (ending up with swollen resin in DMF).
Step 4: The nitro group is reduced via treatment of resin with 1 M solution of SnCl$_2$ as in example 12 in DMF at ambient temperature for 12 h. The resin is washed 3×DMF, 2×DCM, 2×DMF, (ending up with swollen resin in DMF).
Step 5: To the resin, is added a solution of 156 mg (1 mmol) 3-chloro benzoic acid, 1 mmol (380 mg) of HATU, and 3 mmol (385 mg=420 µL) of DIEA in 2 mL of DMF. This coupling is done at ambient temperature (RT) for 12 h. The resin is washed 3×DMF, 3×DCM, and dried in vacuum.

For cleavage, 1.5 ml of mixture TFA/water 95:5 are added to the dry resin and shaken at room temperature for 4 h. The resin is filtered off, washed with mixture AN and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=574.13 Da (calc. monoisotopic for $C_{28}H_{29}Cl_3N_4O_3$), measured $(M+H)^+ = 575.1$ Da with appropriate Cl-isotope pattern, UV {220} based purity 92.3%.

EXAMPLE 16

(4-{2-(3-Chloro-benzoylamino)-4-[2-(2,4-dichloro-phenyl)-ethylcarbamoyl]-phenyl}-piperazin-1-yl)-acetic acid ethyl ester

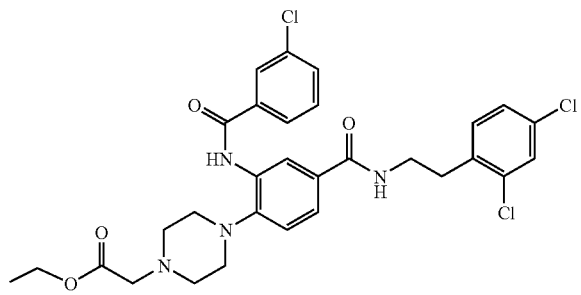

Step 1: Is undertaken as in example 12

Step 2: Is undertaken as in example 12

Step 3: Fluorine substitution is accomplished via treatment of resin using 0.5M solution of 4-(ethoxycarbonyl-methyl)-piperazine in NMP for 48 h at 65° C. The resin is washed 3×DMF, 2×DCM, 2×DMF, (ending up with swollen resin in DMF).

Step 4: The nitro group is reduced via treatment of resin with 1 M solution of $SnCl_2$ as in example 12 in DMF at ambient temperature for 12 h. The resin is washed 3×DMF, 2×DCM, 2×DMF, (ending up with swollen resin in DMF).

Step 5: To the resin, is added a solution of 156 mg (1 mmol) 3-chloro benzoic acid, 1 mmol (380 mg) of HATU, and 3 mmol (385 mg=420 µL) of DIEA in 2 mL of DMF. This coupling is done at ambient temperature (RT) for 12 h. The resin is washed 3×DMF, 3×DCM, and dried in vacuum.

For cleavage, 1.5 ml of mixture TFA/water 95:5 are added to the dry resin and shaken at room temperature for 4 h. The resin is filtered off, washed with mixture AN and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=616.14 Da (calc. monoisotopic for $C_{30}H_{31}Cl_3N_4O_4$), measured $(M+H)^+ = 617.1$ Da with appropriate Cl-isotope pattern, UV {220} based purity 87.5%.

EXAMPLE 17

3-(3-Chloro-benzoylamino)-N-[2-(2,4-dichloro-phenyl)-ethyl]-4-(4-ethyl-piperazin-1-yl)-benzamide

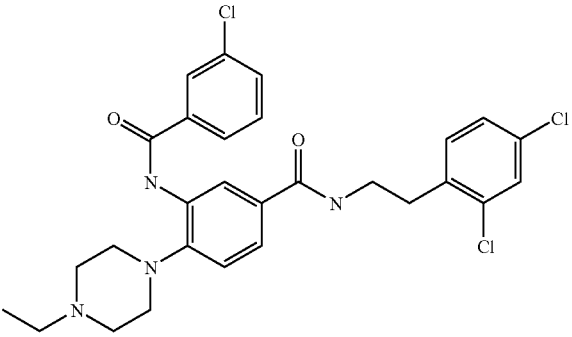

Step 1: Is undertaken as in example 12

Step 2: Is undertaken as in example 12

Step 3: Fluorine substitution is accomplished via treatment of resin using 0.5M solution of 4-ethyl-piperazine in NMP for 48 h at 65° C. The resin is washed 3×DMF, 2×DCM, 2×DMF, (ending up with swollen resin in DMF).

Step 4: The nitro group is reduced via treatment of resin with 1 M solution of $SnCl_2$ as in example 12 in DMF at ambient temperature for 12 h. The resin is washed 3×DMF, 2×DCM, 2×DMF, (ending up with swollen resin in DMF).

Step 5: To the resin, is added a solution of 156 mg (1 mmol) 3-chloro benzoic acid, 1 mmol (380 mg) of HATU, and 3 mmol (385 mg=420 µL) of DIEA in 2 mL of DMF. This coupling is done at ambient temperature (RT) for 12 h. The resin is washed 3×DMF, 3×DCM, and dried in vacuum.

For cleavage, 1.5 ml of mixture TFA/water 95:5 are added to the dry resin and shaken at room temperature for 4 h. The resin is filtered off, washed with mixture AN and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=558.14 Da (calc. monoisotopic for $C_{28}H_{29}Cl_3N_4O_2$), measured $(M+H)^+ = 559.1$ Da with appropriate Cl-isotope pattern, UV {220} based purity 100%.

EXAMPLE 18

3-(3-Chloro-benzoylamino)-N-[2-(2,4-dichloro-phenyl)-ethyl]-4-{-4,2-(2-hydroxy-ethoxy)-ethyl]-piperazin-1-yl}-benzamide

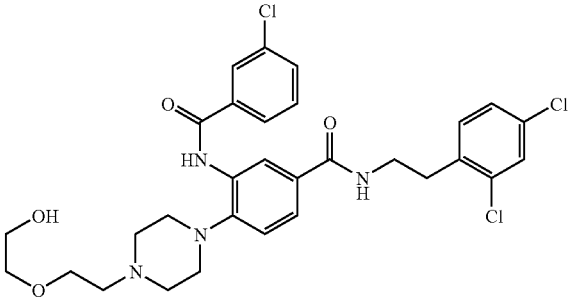

Step 1: Is undertaken as in example 12

Step 2: Is undertaken as in example 12

Step 3: Fluorine substitution is accomplished via treatment of resin using 0.5M solution of 2-(2-piperazin-1-yl-ethoxy)-ethanol in NMP for 48 h at 65° C. The resin is washed 3×DMF, 2×DCM, 2×DMF, (ending up with swollen resin in DMF).

Step 4: The nitro group is reduced via treatment of resin with 1 M solution of $SnCl_2$ as in example 12 in DMF at ambient temperature for 12 h. The resin is washed 3×DMF, 2×DCM, 2×DMF, (ending up with swollen resin in DMF).

Step 5: To the resin, is added a solution of 156 mg (1 mmol) 3-chloro benzoic acid, 1 mmol (380 mg) of HATU, and 3 mmol (385 mg=420 μL) of DIEA in 2 mL of DMF. This coupling is done at ambient temperature (RT) for 12 h. The resin is washed 3×DMF, 3×DCM, and dried in vacuum.

For cleavage, 1.5 ml of mixture TFA/water 95:5 are added to the dry resin and shaken at room temperature for 4 h. The resin is filtered off, washed with mixture AN and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=618.16 Da (calc. monoisotopic for $C_{30}H_{33}Cl_3N_4O_4$), measured $(M+H)^+= 619.2$ Da with appropriate Cl-isotope pattern, UV {220} based purity 97%.

EXAMPLE 19

3-(3-Chloro-benzoylamino)-N-[2-(2,4-dichloro-phenyl)-ethyl]-4-[4-(1-methyl-piperidin-4-yl)-piperazin-1-yl]-benzamide

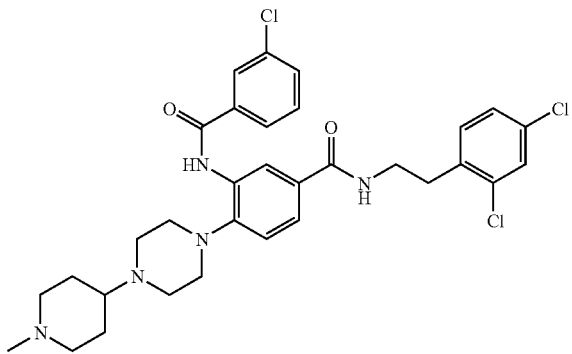

Step 1: Is undertaken as in example 12
Step 2: Is undertaken as in example 12
Step 3: Fluorine substitution is accomplished via treatment of resin using 0.5M solution of 1-(1-Methyl-piperidin-4-yl)-piperazine in NMP for 48 h at 65° C. The resin is washed 3×DMF, 2×DCM, 2×DMF, (ending up with swollen resin in DMF).

Step 4: The nitro group is reduced via treatment of resin with 1 M solution of $SnCl_2$ as in example 12 in DMF at ambient temperature for 12 h. The resin is washed 3×DMF, 2×DCM, 2×DMF, (ending up with swollen resin in DMF).

Step 5: To the resin, is added a solution of 156 mg (1 mmol) 3-chloro benzoic acid, 1 mmol (380 mg) of HATU, and 3 mmol (385 mg=420 μL) of DIEA in 2 mL of DMF. This coupling is done at ambient temperature (RT) for 12 h. The resin is washed 3×DMF, 3×DCM, and dried in vacuum.

For cleavage, 1.5 ml of mixture TFA/water 95:5 are added to the dry resin and shaken at room temperature for 4 h. The resin is filtered off, washed with mixture AN and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=627.19 Da (calc. monoisotopic for $C_{32}H_{36}Cl_3N_5O_2$), measured $(M+H)^+= 628.2$ Da with appropriate Cl-isotope pattern, UV {220 nm} based purity 83.2%.

Preloaded Resin I

This preloaded resin is used for preparation of compound in examples 20-21, 24, 61, 63-64, and 71.

Preparation of Preloaded Resin I:

Step 1: 20 g of FMPE polystyrene HL Resin cat #01-64-0254 (NovaBiochem—'Ameba' S=0.92 mmol/g, EMD Biosciences, Inc.) in 250 ml plastic bottle is treated with a mixture of 29.1 g 2,4-dichloro-phenethyl amine and 32.6 g of in DCM/TMOF (1:1) 16 h at ambient temperature to create and subsequently reduce the Schiff base. The resin is then washed with 2×MeOH, 3× by 10% AcOH in DMF, 3× by DMF, 3×DCM.

Step 2: 15 g of resin from previous reaction, is treated with 4.27 g of 4-fluoro-3-nitro benzoic acid, 8.78 g of HATU, and 12.06 ml of DIEA in DMF/DCM mixture (1:1). This coupling is done at ambient temperature (RT) for 12 h. The resin is washed 3×DMF, 3×DCM, 2×DMF, (ending up with swollen resin in DMF).

Step 3: Fluorine substitution is accomplished via treatment of 5 g resin using 0.5M solution of piperazine in NMP for 48 h at 65° C. The resin is washed 3×DMF, 2×DCM, 2×DMF, (ending up with swollen resin in DMF).

EXAMPLE 21

3-(3-Chloro-benzoylamino)-N-[2-(2,4-dichloro-phenyl)-ethyl]-4-[4-(1-methyl-piperidin-4-ylmethyl)-piperazin-1-yl]-benzamide

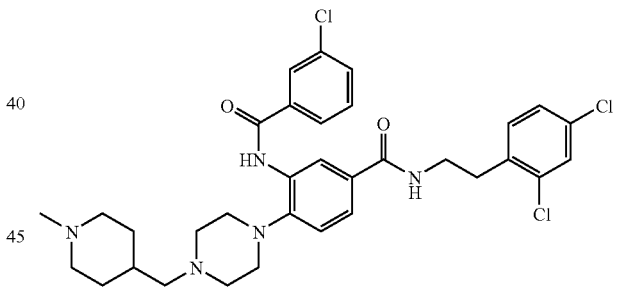

200 mg of preloaded resin I (after step 1 and 2) is converted to final product as follows:

Step 3: Fluorine substitution is accomplished via treatment of 5 g resin using 0.5M solution of 4-(1-methyl-piperidin-4-ylmethyl)-piperazine in NMP for 16 h at 80° C. The resin is washed 3×DMF, 2×DCM, 2×DMF, (ending up with swollen resin in DMF).

Step 4: The nitro group is reduced via treatment of resin with 1 M solution of $SnCl_2$ as in example 12 in DMF at ambient temperature for 12 h. The resin is washed 3×DMF, 2×DCM, 2×DMF, (ending up with swollen resin in DMF).

Step 5: To the resin, is added a solution of 156 mg (1 mmol) 3-chloro benzoic acid, 1 mmol (380 mg) of HATU, and 3 mmol (385 mg=420 μL) of DIEA in 3.5 mL of DMF. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using RP-HPLC Beckman system and procedure outlined in the General procedures section. MW=641.21 Da (calc. monoisotopic for $C_{33}H_{38}Cl_3N_5O_2$), measured $(M+H)^+$=642.2 Da with appropriate Cl-isotope pattern, UV {220} based purity 79.7%.

EXAMPLE 21

4-[1,4']Bipiperidinyl-1'-yl-3-(3-chloro-benzoylamino)-N-[2-(4-chloro-phenyl)-ethyl]-benzamide

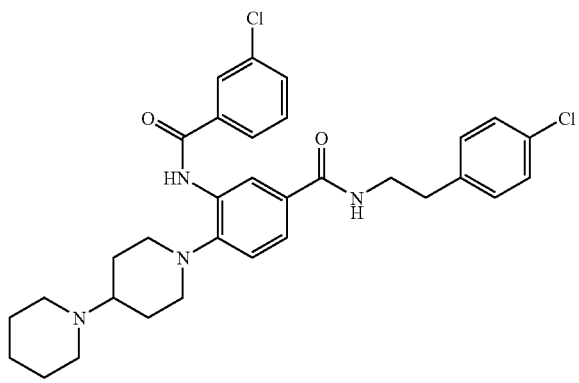

200 mg of preloaded resin I (after step 1 and 2) is converted to final product as follows:

Step 3: Fluorine substitution is accomplished via treatment of resin using 2 M solution of [1,4']Bipiperidinyl in NMP for 16 h at 80° C. The resin is washed 3×DMF, 2×DCM, 2×DMF, (ending up with swollen resin in DMF).

Step 4: The nitro group is reduced via treatment of resin with 1 M solution of $SnCl_2$ as in example 12 in DMF at ambient temperature for 12 h. The resin is washed 3×DMF, 2×DCM, 2×DMF, (ending up with swollen resin in DMF).

Step 5: To the resin, is added a solution of 156 mg (1 mmol) 3-chloro benzoic acid, 1 mmol (380 mg) of HATU, and 3 mmol (385 mg=420 μL) of DIEA in 3.5 mL of DMF. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using RP-HPLC Beckman system and procedure outlined in the General procedures section. MW=578.22 Da (calc. monoisotopic for $C_{32}H_{36}Cl_2N_4O_2$), measured $(M+H)^+$=579.2 Da with appropriate Cl-isotope pattern, UV {220} based purity 92.3%.

EXAMPLE 22

3-(3-Chloro-benzoylamino)-N-[2-(2,4-dichloro-phenyl)-ethyl]-4-[4-(2-morpholin-4-yl-ethyl)-piperazin-1-yl]-benzamide

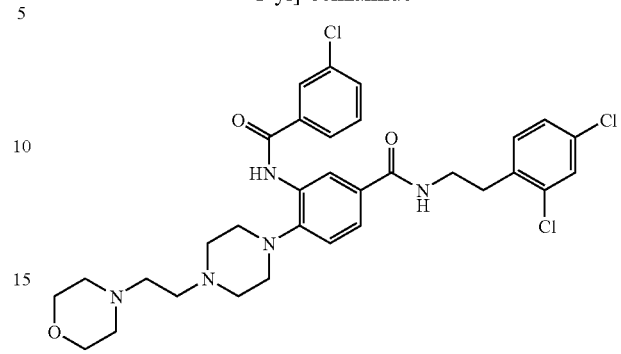

Step 1: Is undertaken as in example 12
Step 2: Is undertaken as in example 12
Step 3: Fluorine substitution is accomplished via treatment of resin using 0.5M solution of 4-(2-morpholin-4-yl-ethyl)-piperazine in NMP for 48 h at 65° C. The resin is washed 3×DMF, 2×DCM, 2×DMF, (ending up with swollen resin in DMF).

Step 4: The nitro group is reduced via treatment of resin with 1 M solution of $SnCl_2$ as in example 12 in DMF at ambient temperature for 12 h. The resin is washed 3×DMF, 2×DCM, 2×DMF, (ending up with swollen resin in DMF).

Step 5: To the resin, is added a solution of 156 mg (1 mmol) 3-chloro benzoic acid, 1 mmol (380 mg) of HATU, and 3 mmol (385 mg=420 μL) of DIEA in 2 mL of DMF. This coupling is done at ambient temperature (RT) for 12 h. The resin is washed 3×DMF, 3×DCM, and dried in vacuum.

For cleavage, 1.5 ml of mixture TFA/water 95:5 are added to the dry resin and shaken at room temperature for 4 h. The resin is filtered off, washed with mixture AN and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=643.19 Da (calc. monoisotopic for $C_{32}H_{36}Cl_3N_5O_3$), measured $(M+H)^+$= 644.2 Da with appropriate Cl-isotope pattern, UV {220} based purity 62.8%.

EXAMPLE 23

3-(3-Chloro-benzoylamino)-N-[2-(2,4-dichloro-phenyl)-ethyl]-4-(4-dimethylcarbamoylmethyl-piperazin-1-yl)-benzamide

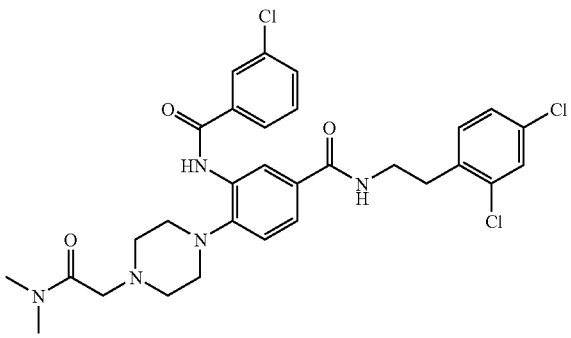

Step 1: Is undertaken as in example 12
Step 2: Is undertaken as in example 12

Step 3: Fluorine substitution is accomplished via treatment of resin using 0.5M solution of piperazino-acetic acid-dimethylamide in NMP for 48 h at 65° C. The resin is washed 3×DMF, 2×DCM, 2×DMF, (ending up with swollen resin in DMF).

Step 4: The nitro group is reduced via treatment of resin with 1 M solution of SnCl$_2$ as in example 12 in DMF at ambient temperature for 12 h. The resin is washed 3×DMF, 2×DCM, 2×DMF, (ending up with swollen resin in DMF).

Step 5: To the resin, is added a solution of 156 mg (1 mmol) 3-chloro benzoic acid, 1 mmol (380 mg) of HATU, and 3 mmol (385 mg=420 µL) of DIEA in 2 mL of DMF. This coupling is done at ambient temperature (RT) for 12 h. The resin is washed 3×DMF, 3×DCM, and dried in vacuum.

For cleavage, 1.5 ml of mixture TFA/water 95:5 are added to the dry resin and shaken at room temperature for 4 h. The resin is filtered off, washed with mixture AN and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=615.16 Da (calc. monoisotopic for $C_{30}H_{32}Cl_3N_5O_3$), measured (M+H)$^+$= 616.2 Da with appropriate Cl-isotope pattern, UV {220} based purity 99.1%.

EXAMPLE 24

3-(3-Chloro-benzoylamino)-N-[2-(2,4-dichloro-phenyl)-ethyl]-4-[4-(2-dimethylamino-acetyl)-piperazin-1-yl]-benzamide

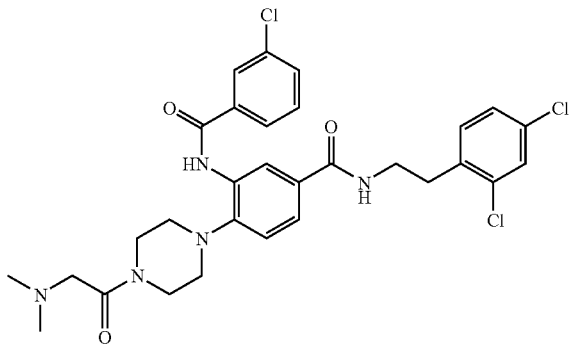

200 mg of preloaded resin I (after step 1, 2 and 3) is converted to final product as follows:

Step 4: HATU coupling of N,N-dimethyl-Glycine is achieved via reaction of 2 mmol of the N,N-dimethyl-Glycine, 2 mmol HATU, 6 mmol of DIEA in 6 ml DMF at ambient temperature for 12 h. The resin is washed 3×DMF, 3×DCM, 3×DMF—end up swollen in DMF.

Step 4: The nitro group is reduced via treatment of resin with 1 M solution of SnCl$_2$ as in example 12 in DMF at ambient temperature for 12 h. The resin is washed 3×DMF, 2×DCM, 2×DMF, (ending up with swollen resin in DMF).

Step 5: To the resin, is added a solution of 156 mg (1 mmol) 3-chloro benzoic acid, 1 mmol (380 mg) of HATU, and 3 mmol (385 mg=420 µL) of DIEA in 3.5 mL of DMF. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using RP-HPLC Beckman system and procedure outlined in the General procedures section. MW=615.16 Da (calc. monoisotopic for $C_{30}H_{32}Cl_3N_5O_3$), measured (M+H)$^+$=616.2 Da with appropriate Cl-isotope pattern, UV (220) based purity 94.7%.

EXAMPLE 25

3-(3-Chloro-benzoylamino)-N-[2-(2,4-dichloro-phenyl)-ethyl]-4-(4-pyridin-2-ylmethyl-piperazin-1-yl)-benzamide

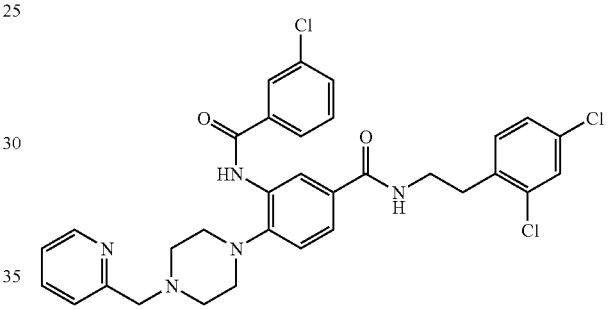

Step 1: Is undertaken as in example 12

Step 2: Is undertaken as in example 12

Step 3: Fluorine substitution is accomplished via treatment of resin using 0.5M solution of 4-(pyridin-2-yl-methyl)-piperazine in NMP for 48 h at 65° C. The resin is washed 3×DMF, 2×DCM, 2×DMF, (ending up with swollen resin in DMF).

Step 4: The nitro group is reduced via treatment of resin with 1 M solution of SnCl$_2$ as in example 12 in DMF at ambient temperature for 12 h. The resin is washed 3×DMF, 2×DCM, 2×DMF, (ending up with swollen resin in DMF).

Step 5: To the resin, is added a solution of 156 mg (1 mmol) 3-chloro benzoic acid, 1 mmol (380 mg) of HATU, and 3 mmol (385 mg=420 µL) of DIEA in 2 mL of DMF. This coupling is done at ambient temperature (RT) for 12 h. The resin is washed 3×DMF, 3×DCM, and dried in vacuum.

For cleavage, 1.5 ml of mixture TFA/water 95:5 are added to the dry resin and shaken at room temperature for 4 h. The resin is filtered off, washed with mixture AN and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=621.15 Da (calc. monoisotopic for $C_{32}H_{30}Cl_3N_5O_2$), measured (M+H)$^+$= 622.1 Da with appropriate Cl-isotope pattern, UV {220} based purity 99.3%.

EXAMPLE 26

3-(3-Chloro-benzoylamino)-N-[2-(2,4-dichloro-phenyl)-ethyl]-4-(4-pyridin-3-ylmethyl-piperazin-1-yl)-benzamide

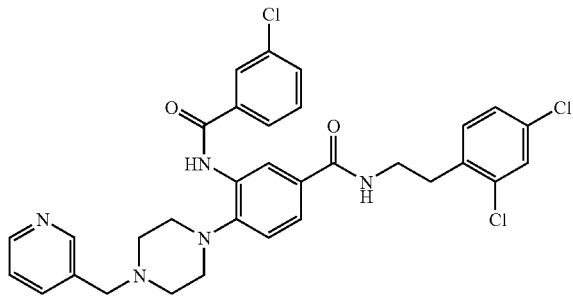

Step 1: Is undertaken as in example 12
Step 2: Is undertaken as in example 12
Step 3: Fluorine substitution is accomplished via treatment of resin using 0.5M solution of 4-(pyridin-3-yl-methyl)-piperazine in NMP for 48 h at 65° C. The resin is washed 3×DMF, 2×DCM, 2×DMF, (ending up with swollen resin in DMF).
Step 4: The nitro group is reduced via treatment of resin with 1 M solution of SnCl$_2$ as in example 12 in DMF at ambient temperature for 12 h. The resin is washed 3×DMF, 2×DCM, 2×DMF, (ending up with swollen resin in DMF).
Step 5: To the resin, is added a solution of 156 mg (1 mmol) 3-chloro benzoic acid, 1 mmol (380 mg) of HATU, and 3 mmol (385 mg=420 μL) of DIEA in 2 mL of DMF. This coupling is done at ambient temperature (RT) for 12 h. The resin is washed 3×DMF, 3×DCM, and dried in vacuum.

For cleavage, 1.5 ml of mixture TFA/water 95:5 are added to the dry resin and shaken at room temperature for 4 h. The resin is filtered off, washed with mixture AN and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=621.15 Da (calc. monoisotopic for $C_{32}H_{30}Cl_3N_5O_2$), measured (M+H)$^+$= 622.1 Da with appropriate Cl-isotope pattern, UV {220} based purity 96.4%.

EXAMPLE 27

3-(3-Chloro-benzoylamino)-N-[2-(2,4-dichloro-phenyl)-ethyl]-4-[4-(tetrahydro-furan-2-ylmethyl)-piperazin-1-yl]-benzamide

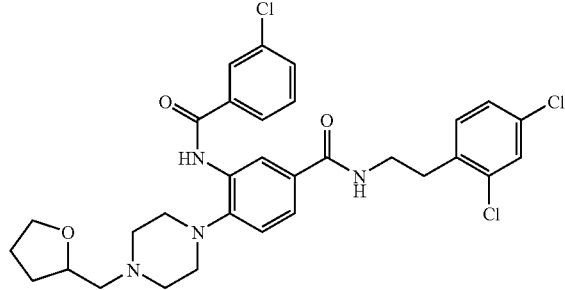

Step 1: Is undertaken as in example 12
Step 2: Is undertaken as in example 12
Step 3: Fluorine substitution is accomplished via treatment of resin using 0.5M solution of 1-(Tetrahydro-furan-2-ylmethyl)-piperazine in NMP for 48 h at 65° C. The resin is washed 3×DMF, 2×DCM, 2×DMF, (ending up with swollen resin in DMF).
Step 4: The nitro group is reduced via treatment of resin with 1 M solution of SnCl$_2$ as in example 12 in DMF at ambient temperature for 12 h. The resin is washed 3×DMF, 2×DCM, 2×DMF, (ending up with swollen resin in DMF).
Step 5: To the resin, is added a solution of 156 mg (1 mmol) 3-chloro benzoic acid, 1 mmol (380 mg) of HATU, and 3 mmol (385 mg=420 μL) of DIEA in 2 mL of DMF. This coupling is done at ambient temperature (RT) for 12 h. The resin is washed 3×DMF, 3×DCM, and dried in vacuum.

For cleavage, 1.5 ml of mixture TFA/water 95:5 are added to the dry resin and shaken at room temperature for 4 h. The resin is filtered off, washed with mixture AN and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=614.16 Da (calc. monoisotopic for $C_{31}H_{33}Cl_3N_4O_3$), measured (M+H)$^+$= 615.2 Da with appropriate Cl-isotope pattern, UV {220} based purity 96.1%.

EXAMPLE 28

3-(3-Chloro-benzoylamino)-N-[2-(2,4-dichloro-phenyl)-ethyl]-4-[4-(2-dimethylamino-ethyl)-piperidin-1-yl]-benzamide

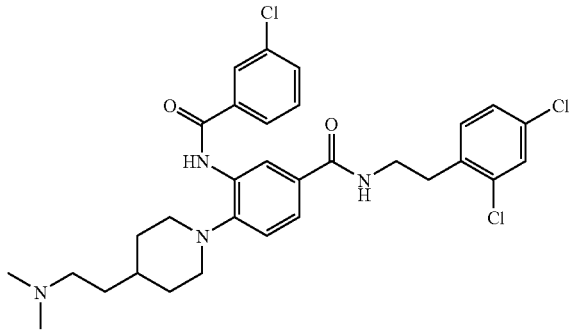

Step 1: Is undertaken as in example 12
Step 2: Is undertaken as in example 12
Step 3: Fluorine substitution is accomplished via treatment of resin using 0.5M solution of 4-(2-dimethylamino-ethyl)-piperidine in NMP for 48 h at 65° C. The resin is washed 3×DMF, 2×DCM, 2×DMF, (ending up with swollen resin in DMF).
Step 4: The nitro group is reduced via treatment of resin with 1 M solution of SnCl$_2$ as in example 12 in DMF at ambient temperature for 12 h. The resin is washed 3×DMF, 2×DCM, 2×DMF, (ending up with swollen resin in DMF).
Step 5: To the resin, is added a solution of 156 mg (1 mmol) 3-chloro benzoic acid, 1 mmol (380 mg) of HATU, and 3 mmol (385 mg=420 μL) of DIEA in 2 mL of DMF. This coupling is done at ambient temperature (RT) for 12 h. The resin is washed 3×DMF, 3×DCM, and dried in vacuum.

For cleavage, 1.5 ml of mixture TFA/water 95:5 are added to the dry resin and shaken at room temperature for 4 h. The resin is filtered off, washed with mixture AN and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=600.18 Da (calc. monoisotopic for $C_{31}H_{35}Cl_3N_4O_2$), measured $(M+H)^+$= 601.2 Da with appropriate Cl-isotope pattern, UV {220} based purity 62%.

EXAMPLE 29

3-(3-Chloro-benzoylamino)-N-[2-(2,4-dichloro-phenyl)-ethyl]-4-[4-(2-methoxy-ethyl)-piperazin-1-yl]-benzamide

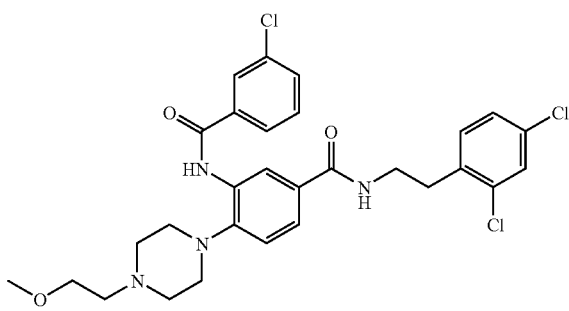

Step 1: Is undertaken as in example 12
Step 2: Is undertaken as in example 12
Step 3: Fluorine substitution is accomplished via treatment of resin using 0.5M solution of 4-(2-methoxy-ethyl)-piperazine in NMP for 48 h at 65° C. The resin is washed 3×DMF, 2×DCM, 2×DMF, (ending up with swollen resin in DMF).
Step 4: The nitro group is reduced via treatment of resin with 1 M solution of $SnCl_2$ as in example 12 in DMF at ambient temperature for 12 h. The resin is washed 3×DMF, 2×DCM, 2×DMF, (ending up with swollen resin in DMF).
Step 5: To the resin, is added a solution of 156 mg (1 mmol) 3-chloro benzoic acid, 1 mmol (380 mg) of HATU, and 3 mmol (385 mg=420 μL) of DIEA in 2 mL of DMF. This coupling is done at ambient temperature (RT) for 12 h. The resin is washed 3×DMF, 3×DCM, and dried in vacuum.

For cleavage, 1.5 ml of mixture TFA/water 95:5 are added to the dry resin and shaken at room temperature for 4 h. The resin is filtered off, washed with mixture AN and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=588.15 Da (calc. monoisotopic for $C_{29}H_{31}Cl_3N_4O_3$), measured $(M+H)^+$= 589.1 Da with appropriate Cl-isotope pattern, UV {220} based purity 99.5%.

Preloaded resin II

The following procedures are used to prepare appropriate construct-preloaded resins for final preparation of compounds described in Examples 30-53.

8 20 ml syringes are charged each with 1 g of FMPE polystyrene HL Resin cat #01-64-0254 (NovaBiochem-'Ameba' S=1.54 mmol/g, EMD Biosciences, Inc.) and let to swell in DCM for 1 h. The following procedures are applied.

Step 1: Swollen resin in each syringe is treated with 12 mL of 0.4 M solution (4.8 mmol) of corresponding amine in DCM/TMOF (1:1) 12 h at ambient temperature to create the Schiff base. Amines used: 2'-fluoro-phenethylamine, 4'-bromo-phenethylamine, 4'-fluorophenethyl amine, 1-(4'-chlorophenethyl)-2-amino-propane, 1,2-diphenyl-ethyl-amine, trans-2-phenyl-1-amino-cyclopropane, 2',6'-dichloro-phenethylamine, 2-phenyl-propylamine. After 2 quick washes using THF, reduction of the Schiff base is achieved via treatment of resin with $NaBH(OAc)_3$ which is added as solid (5 eq.) and then shaken at ambient temperature for 16 h. The resin is then washed 2×MeOH, 2× by DMF, 2×MeOH, 5×DCM, and 5×DMF.

Step 2: To the resin, is added a solution of 1110 mg (6 mmol) 4-fluoro-3-nitro benzoic acid, 6 mmol (2280 mg) of HATU, 2 ml DIEA in 10 ml DMF/DCM mixture (1:1). This coupling is done at ambient temperature (RT) for 12 h. The resin is washed 5×DMF, 5×DCM, 2×DMF, (ending up with swollen resin in DMF).

Step 3: Fluorine substitution is accomplished via treatment of resin using 12 ml of 0.5M solution of 4-[2-(N,N-dimethylamino]-ethyl]-piperazine in NMP for 48 h at 65° C. The resin is washed 3×DMF, 3×DCM, 3×DMF, (ending up with swollen resin in DMF).

Step 4: The nitro group is reduced via treatment of resin with 1 M solution of $SnCl_2$ as in example 12 in DMF at ambient temperature for 16 h. The resin is washed 3×DMF, 3×DCM, 3×DMF, (ending up with swollen resin in DMF).

Preloaded resins are split into 5 syringes each using 200 mg of resin each.

EXAMPLE 30

Thiophene-3-carboxylic acid {2-[4-(2-dimethylamino-ethyl)-piperazin-1-yl]-5-[2-(2-fluoro-phenyl)-ethylcarbamoyl]-phenyl}-amide

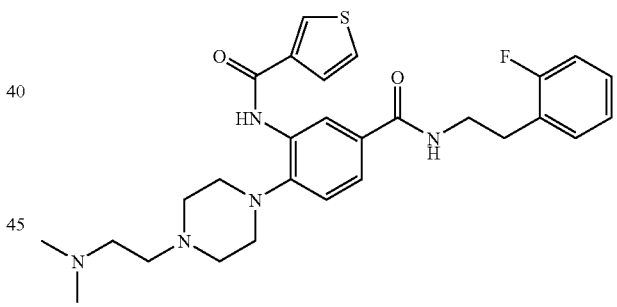

Step 5: To a syringe with 200 mg preloaded resin II with 2'-fluoro-phenethylamine construct, a solution of 128 mg (1 mmol) thiophene-3-carboxylic acid, 1 mmol (380 mg) of HATU, and 3 mmol (385 mg=420 μL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=523.24 Da (calc. monoisotopic for $C_{28}H_{34}FN_5O_2S$), measured $(M+H)^+$=524.2 Da, UV {220} based purity 99.1%.

EXAMPLE 31

Thiophene-3-carboxylic acid {5-[2-(4-chloro-phenyl)-1-methyl-ethylcarbamoyl]-2-[4-(2-dimethylamino-ethyl)-piperazin-1-yl]-phenyl}-amide

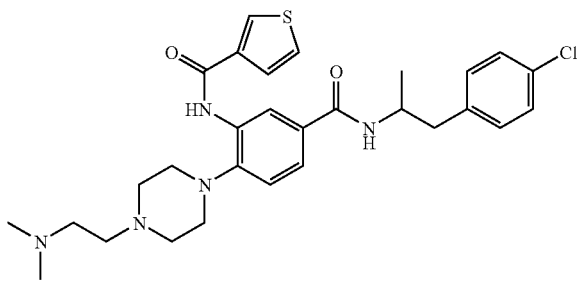

Step 5: To a syringe with 200 mg preloaded resin II with 1-(4'-chlorophenyl)-2-amino-propane construct, a solution of 128 mg (1 mmol) thiophene-3-carboxylic acid, 1 mmol (380 mg) of HATU, and 3 mmol (385 mg=420 µL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=553.23 Da (calc. monoisotopic for $C_{29}H_{36}ClN_5O_2S$), measured $(M+H)^+$=554.2 Da with appropriate Cl-isotope pattern, UV {220} based purity 99.3%.

EXAMPLE 32

Thiophene-3-carboxylic acid {2-[4-(2-dimethylamino-ethyl)-piperazin-1-yl]-5-[2-(4-fluoro-phenyl)-ethylcarbamoyl]-phenyl}-amide

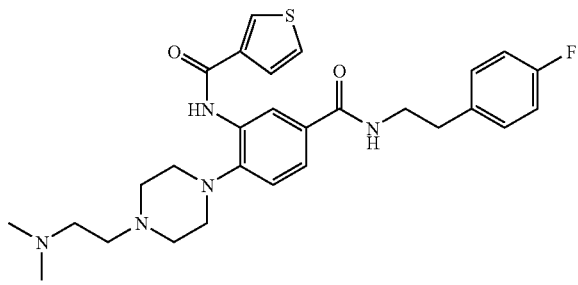

Step 5: To a syringe with 200 mg preloaded resin II with 4'-fluoro-phenethylamine construct, a solution of 128 mg (1 mmol) thiophene-3-carboxylic acid, 1 mmol (380 mg) of HATU, and 3 mmol (385 mg=420 µL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=523.24 Da (calc. monoisotopic for $C_{28}H_{34}FN_5O_2S$), measured $(M+H)^+$=524.2 Da, UV {220} based purity 95.4%.

EXAMPLE 33

Thiophene-3-carboxylic acid {5-[2-(4-bromo-phenyl)-ethylcarbamoyl]-2-[4-(2-dimethylamino-ethyl)-piperazin-1-yl]-phenyl}-amide

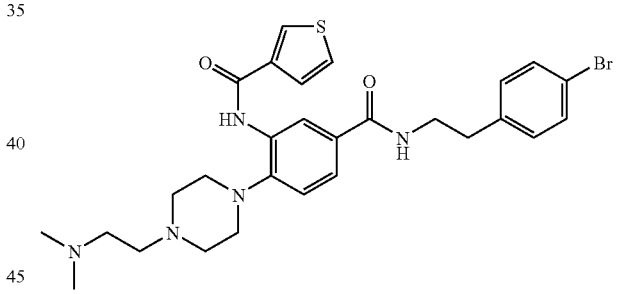

Step 5: To a syringe with 200 mg preloaded resin II with 4'-bromo-phenethylamine construct, a solution of 128 mg (1 mmol) thiophene-3-carboxylic acid, 1 mmol (380 mg) of HATU, and 3 mmol (385 mg=420 µL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=583.16 Da (calc. monoisotopic for $C_{28}H_{34}BrN_5O_2S$), measured $(M+H)^+$=584.2 Da with appropriate Br-isotope pattern, UV {220} based purity 98.7%.

EXAMPLE 34

Thiophene-3-carboxylic acid [2-[4-(2-dimethylamino-ethyl)-piperazin-1-yl]-5-(2-phenyl-propylcarbamoyl)-phenyl]-amide

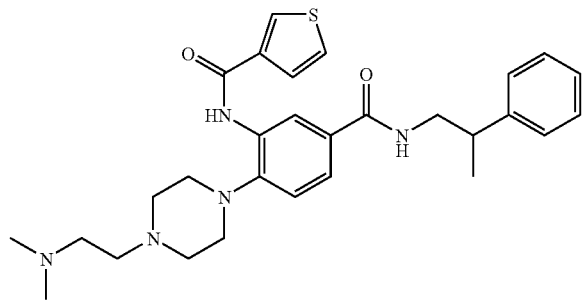

Step 5: To a syringe with 200 mg preloaded resin II with 2-phenyl-amino propane construct, a solution of 128 mg (1 mmol) thiophene-3-carboxylic acid, 1 mmol (380 mg) of HATU, and 3 mmol (385 mg=420 µL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=519.27 Da (calc. monoisotopic for $C_{29}H_{37}N_5O_2S$), measured $(M+H)^+$=520.3 Da, UV {220} based purity 97.7%.

EXAMPLE 35

Thiophene-3-carboxylic acid {5-[2-(2,6-dichlorophenyl)-ethylcarbamoyl]-2-[4-(2-dimethylamino-ethyl)-piperazin-1-yl]-phenyl}-amide

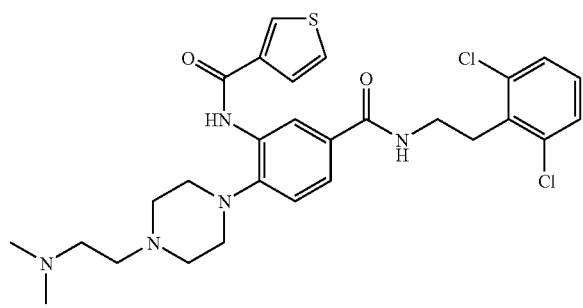

Step 5: To a syringe with 200 mg preloaded resin II with 2',6'-dichloro-phenethylamine construct, a solution of 128 mg (1 mmol) thiophene-3-carboxylic acid, 1 mmol (380 mg) of HATU, and 3 mmol (385 mg=420 µL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=573.17 Da (calc. monoisotopic for $C_{28}H_{33}Cl_2N_5O_2S$), measured $(M+H)^+$=574.2 Da with appropriate Cl-isotope pattern, UV {220} based purity 99.2%.

EXAMPLE 36

Thiophene-3-carboxylic acid [2-[4-(2-dimethylamino-ethyl)-piperazin-1-yl]-5-(2-phenyl-cyclopropylcarbamoyl)-phenyl]-amide

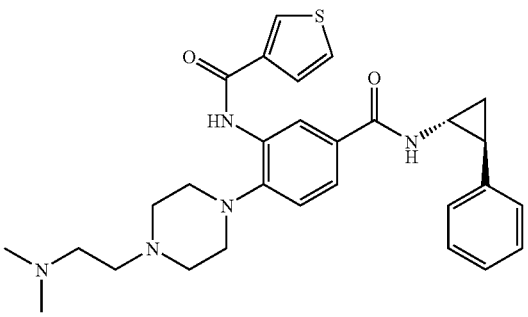

Step 5: To a syringe with 200 mg preloaded resin II with trans-2-phenyl-1-amino-cyclopropane construct, a solution of 128 mg (1 mmol) thiophene-3-carboxylic acid, 1 mmol (380 mg) of HATU, and 3 mmol (385 mg=420 µL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=517.25 Da (calc. monoisotopic for $C_{29}H_{35}N_5O_2S$), measured $(M+H)^+$=518.3 Da, UV {220} based purity 100%.

EXAMPLE 37

Thiophene-3-carboxylic acid [2-[4-(2-dimethy-lamino-ethyl)-piperazin-1-yl]-5-(1,2-diphenyl-ethyl-carbamoyl)-phenyl]-amide

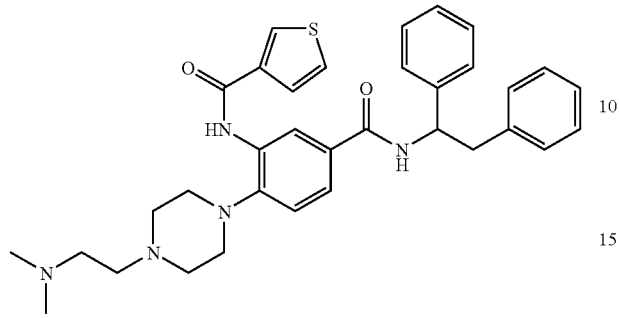

Step 5: To a syringe with 200 mg preloaded resin II with 1,2-diphenyl-ethylamine construct, a solution of 128 mg (1 mmol) thiophene-3-carboxylic acid, 1 mmol (380 mg) of HATU, and 3 mmol (385 mg=420 μL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=581.28 Da (calc. monoisotopic for $C_{34}H_{39}N_5O_2S$), measured $(M+H)^+$=582.3 Da, UV {220} based purity 99.2%.

EXAMPLE 38

Thiophene-2-carboxylic acid {5-[2-(4-chloro-phe-nyl)-1-methyl-ethylcarbamoyl]-2-[4-(2-dimethy-lamino-ethyl)-piperazin-1-yl]-phenyl}-amide

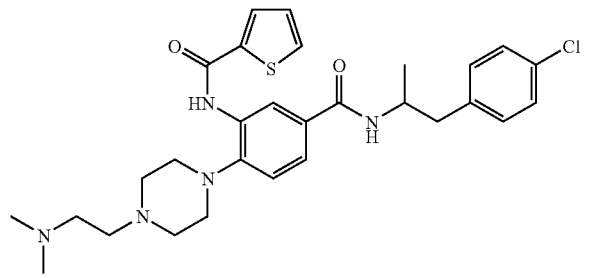

Step 5: To a syringe with 200 mg preloaded II resin with 1-(4'-chlorophenyl)-2-amino-propane construct, a solution of 128 mg (1 mmol) thiophene-2-carboxylic acid, 1 mmol (380 mg) of HATU, and 3 mmol (385 mg=420 μL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=553.23 Da (calc. monoisotopic for $C_{29}H_{36}ClN_5O_2S$), measured $(M+H)^+$=554.2 Da with appropriate Cl-isotope pattern, UV {220} based purity 99.6%.

EXAMPLE 39

Thiophene-2-carboxylic acid {2-[4-(2-dimethy-lamino-ethyl)-piperazin-1-yl]-5-[2-(4-fluoro-phe-nyl)-ethylcarbamoyl]-phenyl}-amide

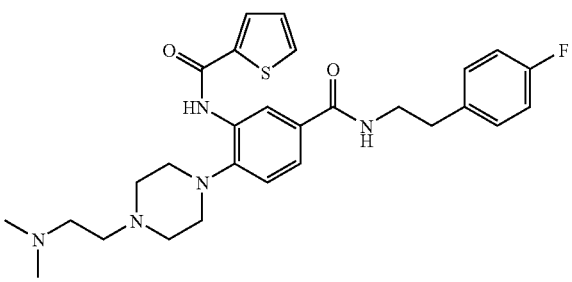

Step 5: To a syringe with 200 mg preloaded resin II with 4'-fluoro-phenethylamine construct, a solution of 128 mg (1 mmol) thiophene-2-carboxylic acid, 1 mmol (380 mg) of HATU, and 3 mmol (385 mg=420 μL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=523.24 Da (calc. monoisotopic for $C_{28}H_{34}FN_5O_2S$), measured $(M+H)^+$=524.2 Da, UV {220} based purity 94.3%.

EXAMPLE 40

Thiophene-2-carboxylic acid {5-[2-(4-bromo-phe-nyl)-ethylcarbamoyl]-2-[4-(2-dimethylamino-ethyl)-piperazin-1-yl]-phenyl}-amide

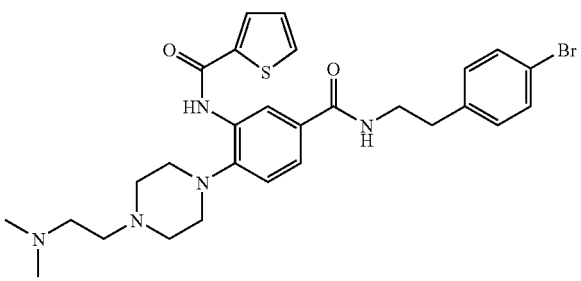

Step 5: To a syringe with 200 mg preloaded resin II with 4'-bromo-phenethylamine construct, a solution of 128 mg (1 mmol) thiophene-2-carboxylic acid, 1 mmol (380 mg) of HATU, and 3 mmol (385 mg=420 μL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=583.16 Da (calc. monoisotopic for $C_{29}H_{36}ClN_5O_2S$), measured $(M+H)^+$=584.2 Da with appropriate Br-isotope pattern, UV {220} based purity 99.5%.

EXAMPLE 41

Thiophene-2-carboxylic acid {2-[4-(2-dimethy-lamino-ethyl)-piperazin-1-yl]-5-[2-(2-fluoro-phenyl)-ethylcarbamoyl]-phenyl}-amide

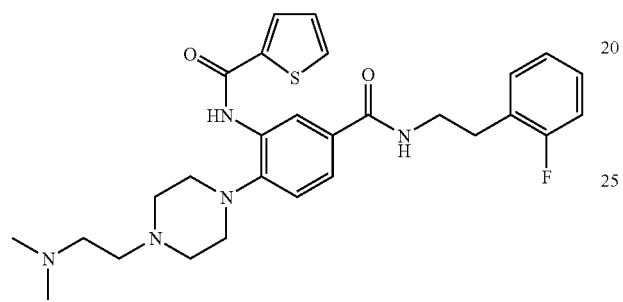

Step 5: To a syringe with 200 mg preloaded resin II with 2'-fluoro-phenethylamine construct, a solution of 128 mg (1 mmol) thiophene-2-carboxylic acid, 1 mmol (380 mg) of HATU, and 3 mmol (385 mg=420 µL) of DIEA in 3.5 mL of DMF is added. This coupling is done at ambient temperature (RT) for 12 h. The resin is washed 3×DMF, 2×DCM, 2×TI-IF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=523.24 Da (calc. monoisotopic for $C_{28}H_{34}FN_5O_2S$), measured $(M+H)^+$=524.2 Da, UV {220} based purity 100%.

EXAMPLE 42

Thiophene-2-carboxylic acid [2-[4-(2-dimethy-lamino-ethyl)-piperazin-1-yl]-5-(2-phenyl-propylcarbamoyl)-phenyl]-amide

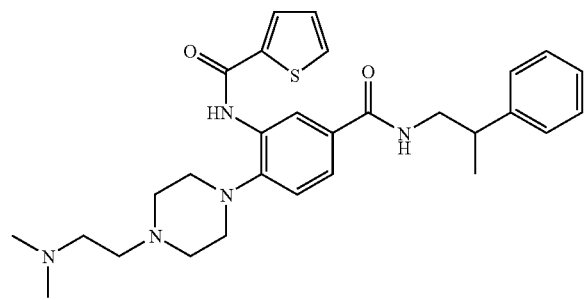

Step 5: To a syringe with 200 mg preloaded resin II with 2-phenyl-amino-propane construct, a solution of 128 mg (1 mmol) thiophene-2-carboxylic acid, 1 mmol (380 mg) of HATU, and 3 mmol (385 mg=420 µL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=519.27 Da (calc. monoisotopic for $C_{29}H_{37}N_5O_2S$), measured $(M+H)^+$=520.3 Da, UV {220} based purity 99.3%.

EXAMPLE 43

Thiophene-2-carboxylic acid {5-[2-(2,6-dichloro-phenyl)-ethylcarbamoyl]-2-[4-(2-dimethylamino-ethyl)-piperazin-1-yl]-phenyl}-amide

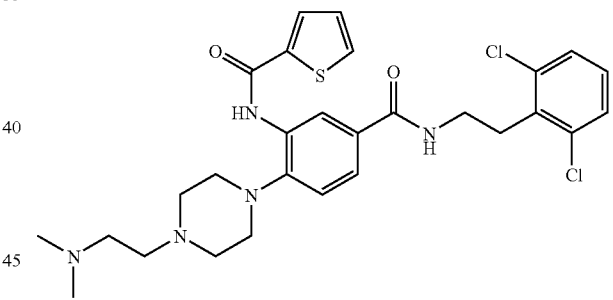

Step 5: To a syringe with 200 mg preloaded resin II with 2',6'-dichloro-phenethylamine construct, a solution of 128 mg (1 mmol) thiophene-2-carboxylic acid, 1 mmol (380 mg) of HATU, and 3 mmol (385 mg=420 µL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=573.17 Da (calc. monoisotopic for $C_{28}H_{33}Cl_2N_5O_2S$), measured $(M+H)^+$=574.2 Da with appropriate Cl-isotope pattern, UV {220} based purity 98.8%.

EXAMPLE 44

Thiophene-2-carboxylic acid [2-[4-(2-dimethylamino-ethyl)-piperazin-1-yl]-5-(2-phenyl-cyclopropylcarbamoyl)-phenyl]-amide

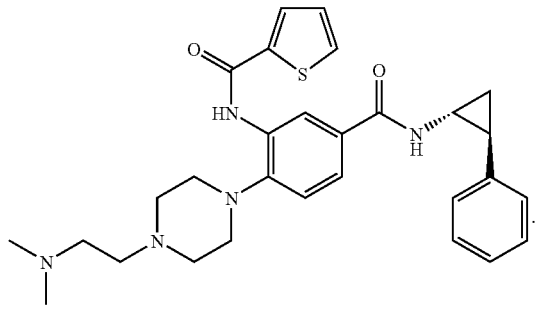

Step 5: To a syringe with 200 mg preloaded resin II with trans-2-phenyl-1-amino-cyclopone construct, a solution of 128 mg (1 mmol) thiophene-2-carboxylic acid, 1 mmol (380 mg) of HATU, and 3 mmol (385 mg=420 μL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=517.25 Da (calc. monoisotopic for $C_{29}H_{35}N_5O_2S$), measured $(M+H)^+$=518.3 Da, UV {220} based purity 100%.

EXAMPLE 45

Thiophene-2-carboxylic acid [2-[4-(2-dimethylamino-ethyl)-piperazin-1-yl]-5-(1,2-diphenyl-ethylcarbamoyl)-phenyl]-amide

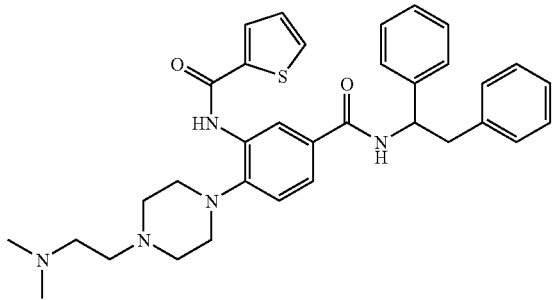

Step 5: To a syringe with 200 mg preloaded resin II with 1,2-diphenyl-ethylamine construct, a solution of 128 mg (1 mmol) thiophene-2-carboxylic acid, 1 mmol (380 mg) of HATU, and 3 mmol (385 mg=420 μL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=581.28 Da (calc. monoisotopic for $C_{34}H_{39}N_5O_2S$), measured $(M+H)^+$=582.3 Da, UV {220} based purity 99%.

EXAMPLE 46

3-(3-Chloro-benzoylamino)-N-[2-(4-chloro-phenyl)-1-methyl-ethyl]-4-[4-(2-dimethylamino-ethyl)-piperazin-1-yl]-benzamide

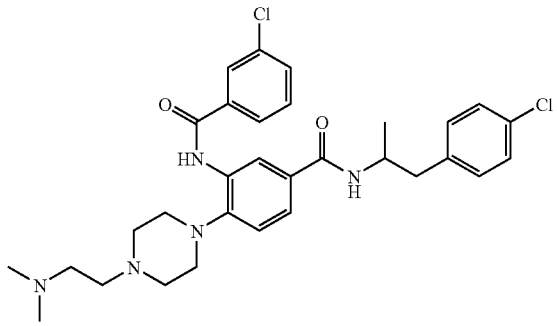

Step 5: To a syringe with 200 mg preloaded resin II with 1-(4'-chlorophenyl)-2-amino-propane construct, a solution of 156 mg (1 mmol) 3-chloro benzoic acid, 1 mmol (380 mg) of HATU, and 3 mmol (385 mg=420 μL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=581.23 Da (calc. monoisotopic for $C_{31}H_{37}Cl_2N_5O_2$), measured $(M+H)^+$=582.2 Da with appropriate Cl-isotope pattern, UV {220} based purity 83.3%.

EXAMPLE 47

3-(3-Chloro-benzoylamino)-4-[4-(2-dimethylamino-ethyl)-piperazin-1-yl]-N-[2-(4-fluoro-phenyl)-ethyl]-benzamide

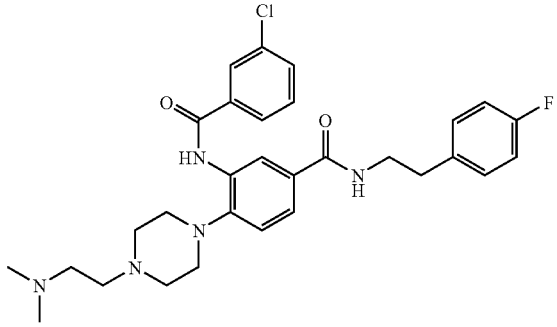

Step 5: To a syringe with 200 mg preloaded resin II with 4'-fluoro-phenethylamine construct, a solution of 156 mg (1 mmol) 3-chloro benzoic acid, 1 mmol (380 mg) of HATU, and 3 mmol (385 mg=420 μL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=551.25 Da (calc. monoisotopic for $C_{30}H_{35}ClFN_5O_2$), measured $(M+H)^+$=552.2 Da with appropriate Cl-isotope pattern, UV {220} based purity 89.4%.

EXAMPLE 48

N-[2-(4-Bromo-phenyl)-ethyl]-3-(3-chloro-benzoylamino)-4-[4-(2-dimethylamino-ethyl)-piperazin-1-yl]-benzamide

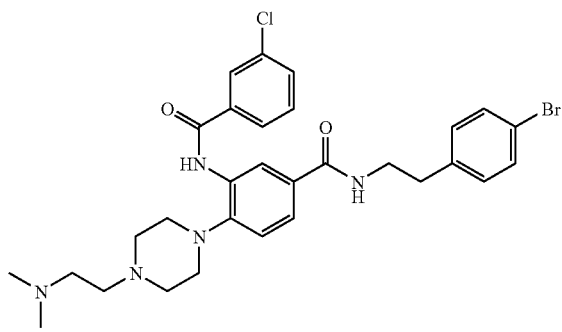

Step 5: To a syringe with 200 mg preloaded resin II with 4'-bromo-phenethylamine construct, a solution of 156 mg (1 mmol) 3-chloro benzoic acid, 1 mmol (380 mg) of HATU, and 3 mmol (385 mg=420 μL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=611.17 Da (calc. monoisotopic for $C_{30}H_{35}BrClN_5O_2$), measured $(M+H)^+$=612.2 Da with appropriate Br—Cl-isotope pattern, UV {220} based purity 98.1%.

EXAMPLE 49

3-(3-Chloro-benzoylamino)-4-[4-(2-dimethylamino-ethyl)-piperazin-1-yl]-N-[2-(2-fluoro-phenyl)-ethyl]-benzamide

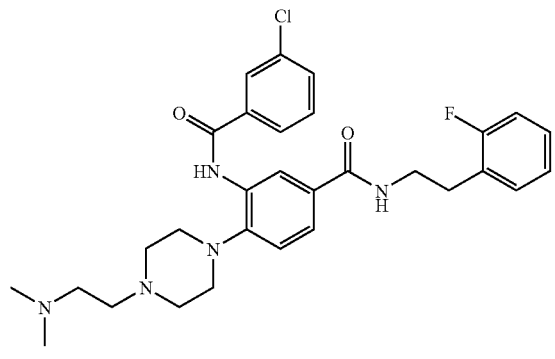

Step 5: To a syringe with 200 mg preloaded resin II with 2'-fluoro-phenethylamine construct, a solution of 156 mg (1 mmol) 3-chloro benzoic acid, 1 mmol (380 mg) of HATU, and 3 mmol (385 mg=420 μL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=551.25 Da (calc. monoisotopic for $C_{30}H_{35}ClFN_5O_2$), measured $(M+H)^+$=552.2 Da with appropriate Cl-isotope pattern, UV {220} based purity 99.2%.

EXAMPLE 50

3-(3-Chloro-benzoylamino)-4-[4-(2-dimethylamino-ethyl)-piperazin-1-yl]-N-(2-phenyl-propyl)-benzamide

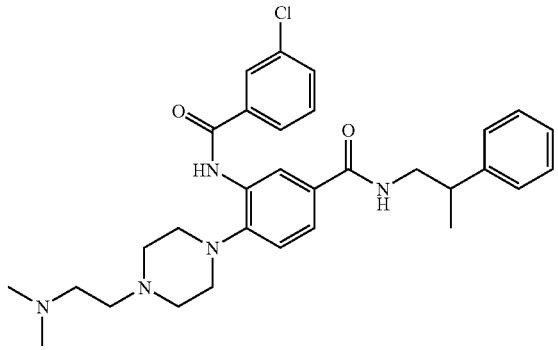

Step 5: To a syringe with 200 mg preloaded resin II with 2-phenyl-1-amino-propane construct, a solution of 156 mg (1 mmol) 3-chloro benzoic acid, 1 mmol (380 mg) of HATU, and 3 mmol (385 mg=420 μL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=547.27 Da (calc. monoisotopic for $C_{31}H_{38}ClN_5O_2$), measured $(M+H)^+=548.3$ Da with appropriate Cl-isotope pattern, UV {220} based purity 96.2%.

EXAMPLE 51

3-(3-Chloro-benzoylamino)-N-[2-(2,6-dichloro-phenyl)-ethyl]-4-[4-(2-dimethylamino-ethyl)-piperazin-1-yl]-benzamide

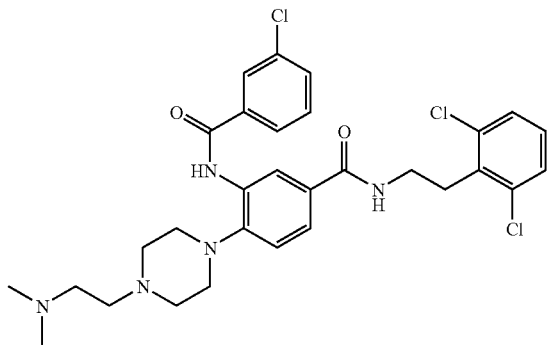

Step 5: To a syringe with 200 mg preloaded resin II with 2′,6′-dichloro-phenethylamine construct, a solution of 156 mg (1 mmol) 3-chloro benzoic acid, 1 mmol (380 mg) of HATU, and 3 mmol (385 mg=420 μL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=601.18 Da (calc. monoisotopic for $C_{30}H_{34}Cl_3N_5O_2$), measured $(M+H)^+=602.2$ Da with appropriate Cl-isotope pattern, UV {220} based purity 90.4%.

EXAMPLE 52

3-(3-Chloro-benzoylamino)-4-[4-(2-dimethylamino-ethyl)-piperazin-1-yl]-N-(2-phenyl-cyclopropyl)-benzamide

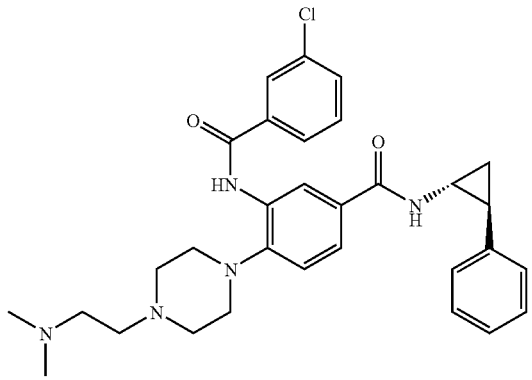

Step 5: To a syringe with 200 mg preloaded resin II with trans-2-phenyl-1-amino-cycloprone construct, a solution of 156 mg (1 mmol) 3-chloro benzoic acid, 1 mmol (380 mg) of HATU, and 3 mmol (385 mg=420 μL) of DIEA in 3.5 mL of DMF is added. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=545.26 Da (calc. monoisotopic for $C_{31}H_{36}ClN_5O_2$), measured $(M+H)^+=546.3$ Da with appropriate Cl-isotope pattern, UV {220} based purity 100%.

EXAMPLE 53

3-(3-Chloro-benzoylamino)-4-[4-(2-dimethylamino-ethyl)-piperazin-1-yl]-N-(1,2-diphenyl-ethyl)-benzamide

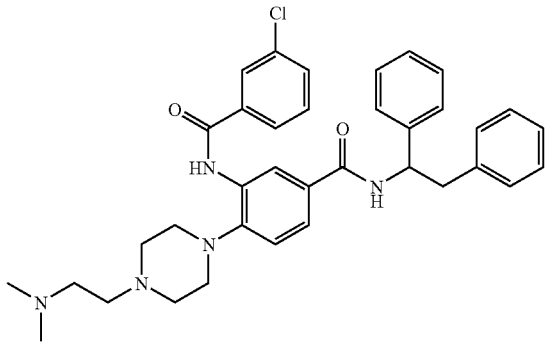

Step 5: To a syringe with 200 mg preloaded resin II with 1,2-diphenyl-ethylamine construct, a solution of 156 mg (1 mmol) 3-chloro benzoic acid, 1 mmol (380 mg) of HATU, and 3 mmol (385 mg=420 μL) of DIEA in 3.5 mL of DMF. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=609.29 Da (calc. monoisotopic for $C_{36}H_{40}ClN_5O_2$), measured $(M+H)^+$=610.3 Da with appropriate Cl-isotope pattern, UV {220} based purity 98.9%.

EXAMPLE 54

3-(3-Chloro-benzoylamino)-4-(2,8-diaza-spiro[4.5]dec-8-yl)-N-[2-(2,4-dichloro-phenyl)-ethyl]-benzamide

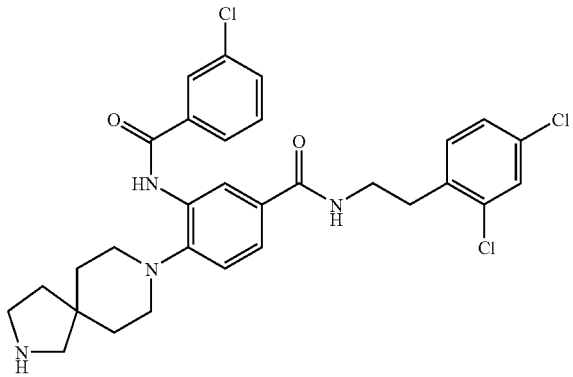

0.5 g of FMPE polystyrene HL Resin cat #01-64-0254 (NovaBiochem—'Ameba' S=1.54 mmol/g, EMD Biosciences, Inc.) in 10 mL syringe preloaded with 2,4-dichlorophenethyl amine and 4-fluoro-3-nitro benzoic acid (see 1346JU144) is submitted to Step 3 as follows.

Step 3: Fluorine substitution is accomplished via treatment of resin using 0.5M solution of Boc-2,8-Diaza-spiro[4.5]decane in NMP for 16 h at 80° C. The resin is washed 3×DMF, 2×DCM, 2×DMF, (ending up with swollen resin in DMF).

Step 4: The nitro group is reduced via treatment of resin with 1 M solution of $SnCl_2$ as in example 12 in DMF at ambient temperature for 16 h. The resin is washed 3×DMF, 2×DCM, 2×DMF, (ending up with swollen resin in DMF).

Step 5: To the resin, is added a solution of 468 mg (3 mmol) 3-chloro benzoic acid, 3 mmol (1140 mg) of HATU, and 9 mmol (1155 mg=1260 µL) of DIEA in 3.5 mL of DMF. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using RP-HPLC Beckman system and procedure outlined in the General procedures section. MW=584.15 Da (calc. monoisotopic for $C_{30}H_{31}Cl_3N_4O_2$), measured $(M+H)^+$=585.2 Da with appropriate Cl-isotope pattern, UV {220} based purity 95.3%.

EXAMPLE 55

3-(3-Chloro-benzoylamino)-N-[2-(2,4-dichloro-phenyl)-ethyl]-4-(2-methyl-2,8-diaza-spiro[4.5]dec-8-yl)-benzamide

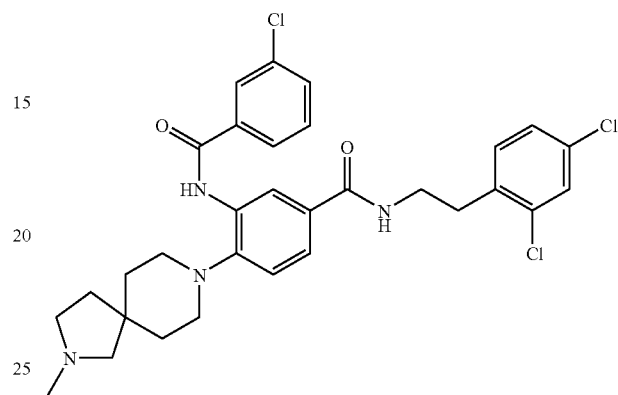

40 mg of product Example 54 is dissolved in 2 mL DCM, 50 µL of AcOH added, followed by 50 µL of 40% aqueous formaldehyde and 200 mg of cyano-borohydride resin. Reaction is shaken at ambient temperature for 3 h. LCMS indicates peak of desired product. Mixture is filtered, evaporated and purified using Waters mass-triggered-LCMS purification system. MW=598.17 Da (calc. monoisotopic for $C_{31}H_{33}Cl_3N_4O_2$), measured $(M+H)^+$=599.2 Da with appropriate Cl-isotope pattern, UV {220} based purity 98.6%.

EXAMPLE 56

3-(3-Chloro-benzoylamino)-4-(3,9-diaza-spiro[5.5]undec-3-yl)-N-[2-(2,4-dichloro-phenyl)-ethyl]-benzamide

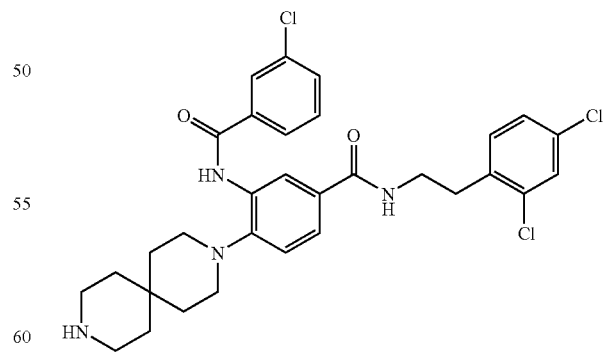

0.5 g of FMPE polystyrene HL Resin cat #01-64-0254 (NovaBiochem—'Ameba' S=1.54 mmol/g, EMD Biosciences, Inc.) in 10 mL syringe preloaded with 2,4-dichlorophenethyl amine and 4-fluoro-3-nitro benzoic acid (see 1346JU144) is submitted to Step 3 as follows.

Step 3: Fluorine substitution is accomplished via treatment of resin using 0.5M solution of boc-3,9-Diaza-spiro[5.5]undecane in NMP for 16 h at 80° C. The resin is washed 3×DMF, 2×DCM, 2×DMF, (ending up with swollen resin in DMF).

Step 4: The nitro group is reduced via treatment of resin with 1 M solution of $SnCl_2$ as in example 12 in DMF at ambient temperature for 16 h. The resin is washed 3×DMF, 2×DCM, 2×DMF, (ending up with swollen resin in DMF).

Step 5: To the resin, is added a solution of 468 mg (3 mmol) 3-chloro benzoic acid, 3 mmol (1140 mg) of HATU, and 9 mmol (1155 mg=1260 μL) of DIEA in 3.5 mL of DMF. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using RP-HPLC Beckman system and procedure outlined in the General procedures section. MW=598.17 Da (calc. monoisotopic for $C_{31}H_{32}Cl_3N_4O_2$), measured $(M+1-1)^+$=599.2 Da with appropriate Cl-isotope pattern, UV {220} based purity 88.9%.

EXAMPLE 57

3-(3-Chloro-benzoylamino)-N-[2-(2,4-dichloro-phenyl)-ethyl]-4-(9-methyl-3,9-diaza-spiro[5.5]undec-3-yl)-benzamide

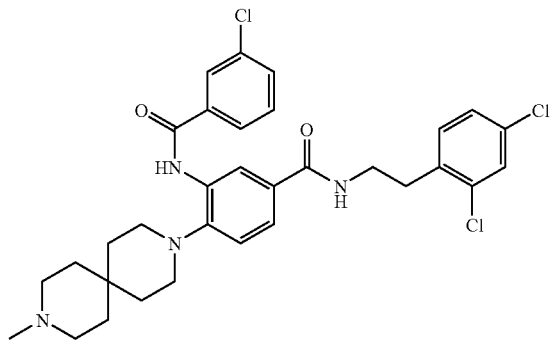

35 mg of product Example 56 is dissolved in 2 mL DCM, 50 μL of AcOH added, followed by 50 μL of 40% aqueous formaldehyde and 200 mg of cyano-borohydride resin. Reaction is shaken at ambient temperature for 3 h. LCMS indicates peak of desired product. Mixture is filtered, evaporated and purified using Waters mass-triggered-LCMS purification system. MW=612.18 Da (calc. monoisotopic for $C_{32}H_{35}Cl_3N_4O_2$), measured $(M+H)^+$=613.2 Da with appropriate Cl-isotope pattern, UV {220} based purity 100%.

EXAMPLE 58

9-{2-(3-Chloro-benzoylamino)-4-[2-(2,4-dichloro-phenyl)-ethylcarbamoyl]-phenyl}-3,3-dimethyl-9-aza-3-azonia-spiro[5.5]undecane trifluoroacetate

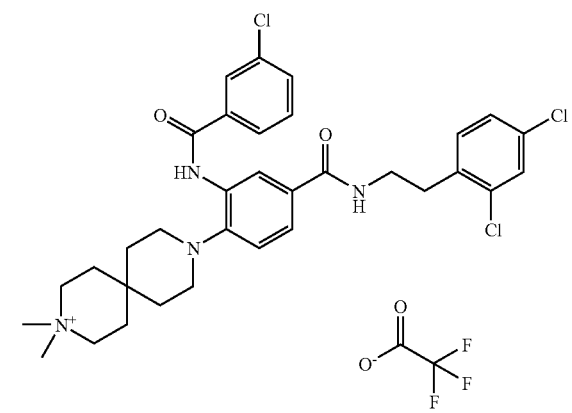

35 mg of product Example 57 is dissolved in 2 mL acetone, 200 μL of methyl iodide added, and the reaction mixture is heated to 80° C. for 1 h in a sealed tube. LCMS indicates peak of desired product. Mixture is evaporated and purified using RP-HPLC Beckman system and procedure outlined in the General procedures section. MW=627.21 Da (calc. monoisotopic for $C_{33}H_{38}Cl_3N_4O_2$), measured $(M+H)^+$=628.2 Da with appropriate Cl-isotope pattern, UV {220} based purity 100%.

EXAMPLE 59

3-(3-Chloro-benzoylamino)-4-(2,7-diaza-spiro[3.5]non-7-yl)-N-[2-(2,4-dichloro-phenyl)-ethyl]-benzamide

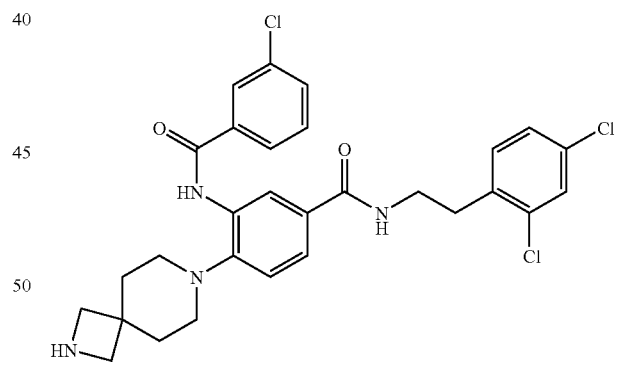

200 mg of preloaded resin I (after step 1 and 2) is converted to final product as follows:

Step 3: Fluorine substitution is accomplished via treatment of resin using 0.4M solution of 2,7-Diaza-spiro[3.5]nonane-2-carboxylic acid tert-butyl ester in NMP for 16 h at 80° C. The resin is washed 3×DMF, 2×DCM, 2×DMF, (ending up with swollen resin in DMF).

Step 4: The nitro group is reduced via treatment of resin with 1 M solution of $SnCl_2$ as in example 12 in DMF at ambient temperature for 12 h. The resin is washed 3×DMF, 2×DCM, 2×DMF, (ending up with swollen resin in DMF).

Step 5: To the resin, is added a solution of 156 mg (1 mmol) 3-chloro benzoic acid, 1 mmol (380 mg) of HATU, and 3 mmol (385 mg=420 μL) of DIEA in 3.5 mL of DMF. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using RP-HPLC Beckman system and procedure outlined in the General procedures section. MW=570.14 Da (calc. monoisotopic for $C_{29}H_{29}Cl_3N_4O_2$), measured $(M+H)^+$=571.2 Da with appropriate Cl-isotope pattern, UV {220} based purity 87%.

EXAMPLE 60

3-(3-Chloro-benzoylamino)-N-[2-(2,4-dichloro-phenyl)-ethyl]-4-(2-methyl-2,7-diaza-spiro[3.5]non-7-yl)-benzamide.

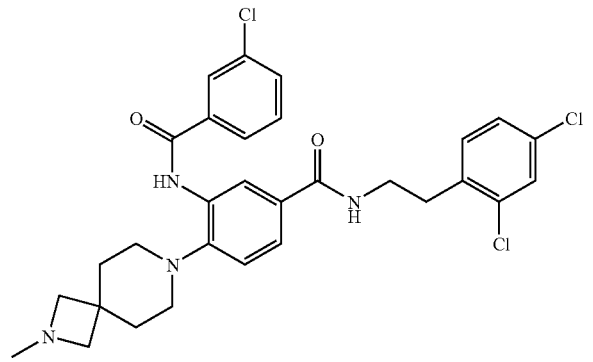

8 mg of compound from preparation of compound in example 59, is dissolved in mixture of 1.5 ml of DCE/TMOF (2:1), 300 ul of 40% $CH_2O$ in water added, shaken 20 minutes and then 100 mg of Cyanoborohydride resin added, and then shaken another 4 h at ambient temperature. Resin filtered off and washed 2×1 ml MeOH, extracts are evaporated. The pure title compound is isolated after HPLC purification using RP-HPLC Beckman system and procedure outlined in the General procedures section. MW=584.15 Da (calc. monoisotopic for $C_{30}H_{31}Cl_3N_4O_2$), measured $(M+H)^+$=583.2 Da with appropriate Cl-isotope pattern, UV {220} based purity 87%.

EXAMPLE 61

4-[4-(3-Amino-propionyl)-piperazin-1-yl]-3-(3-chloro-benzoylamino)-N-[2-(2,4-dichloro-phenyl)-ethyl]benzamide

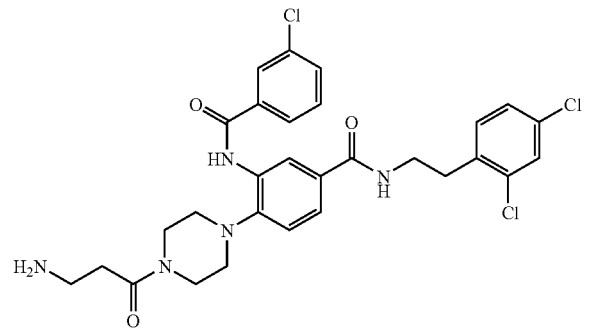

200 mg of preloaded resin I (after step 1, 2 and 3) is converted to final product as follows:

Step 4: HATU coupling Fmoc-beta Alanine is achieved via reaction of 2 mmol of the Fmoc-beta Alanine, 2 mmol HATU, 6 mmol of DIEA in 6 ml DMF at ambient temperature for 12 h. The resin is washed 3×DMF, 3×DCM, 3×DMF—end up swollen in DMF.

Step 4: The nitro group is reduced via treatment of resin with 1M solution of $SnCl_2$ as in example 12 in DMF at ambient temperature for 12 h. The resin is washed 3×DMF, 2×DCM, 2×DMF, (ending up with swollen resin in DMF).

Step 5: To the resin, is added a solution of 156 mg (1 mmol) 3-chloro benzoic acid, 1 mmol (380 mg) of HATU, and 3 mmol (385 mg=420 μL) of DIEA in 3.5 mL of DMF. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using RP-HPLC Beckman system and procedure outlined in the General procedures section. MW=601.14 Da (calc. monoisotopic for $C_{29}H_{30}Cl_3N_5O_3$), measured $(M+H)^+$=602.1 Da with appropriate Cl-isotope pattern, UV {220} based purity 91.2%.

EXAMPLE 62

3-(3-Chloro-benzoylamino)-N-[2-(2,4-dichloro-phenyl)-ethyl]-4-[4-(3-dimethylamino-propionyl)-piperazin-1-yl]-benzamide

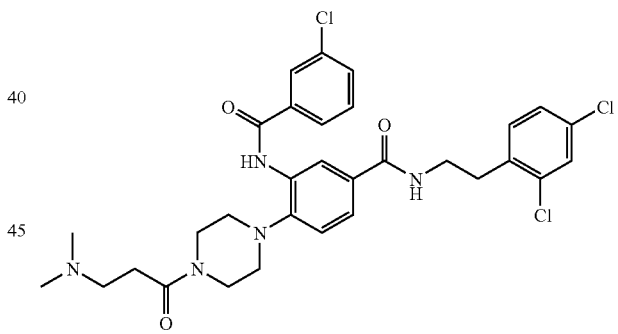

200 mg of preloaded resin I (after step 1, 2 and 3) is converted to final product as follows:

Step 4: HATU coupling of N,N-dimethyl-β alanine is achieved via reaction of 2 mmol of the N,N-dimethyl-β alanine, 2 mmol HATU, 6 mmol of DIEA in 6 ml DMF at ambient temperature for 12 h. The resin is washed 3×DMF, 3×DCM, 3×DMF—end up swollen in DMF.

Step 4: The nitro group is reduced via treatment of resin with 1M solution of $SnCl_2$ as in example 12 in DMF at ambient temperature for 12 h. The resin is washed 3×DMF, 2×DCM, 2×DMF, (ending up with swollen resin in DMF).

Step 5: To the resin, is added a solution of 312 mg (2 mmol) 3-chloro benzoic acid, 2 mmol (760 mg) of HATU, and 6 mmol (770 mg=840 μL) of DIEA in 7 mL of DMF. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=629.17 Da (calc. monoisotopic for $C_{31}H_{34}Cl_3N_5O_3$), measured $(M+H)^+$=630.2 Da with appropriate Cl-isotope pattern, UV {220} based purity 91.4%.

EXAMPLE 63

3-(3-Chloro-benzoylamino)-N-[2-(2,4-dichloro-phenyl)-ethyl]-4-[4-(3-diethylamino-propionyl)-piperazin-1-yl]-benzamide

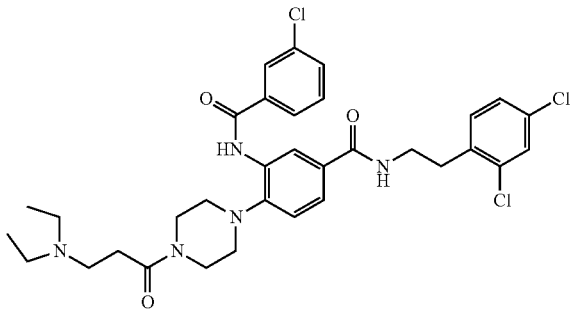

Prepared exactly as compound in Example 66 on 300 mg of preloaded resin, with modification of N,N-diethyl-β alanine being used instead of N,N-dimethyl β alanine. Cleaved compound is purified using Waters mass-triggered-LCMS purification system and procedure outlined in the General procedures section. MW=657.2 Da (calc. monoisotopic for $C_{33}H_{38}Cl_3N_5O_3$), measured $(M+H)^+$=658.2 Da with appropriate Cl-isotope pattern, UV {220} based purity 56.3%.

EXAMPLE 64

3-(3-Chloro-benzoylamino)-N-[2-(2,4-dichloro-phenyl)-ethyl]-4-[4-(3-pyrrolidin-1-yl-propionyl)-piperazin-1-yl]-benzamide

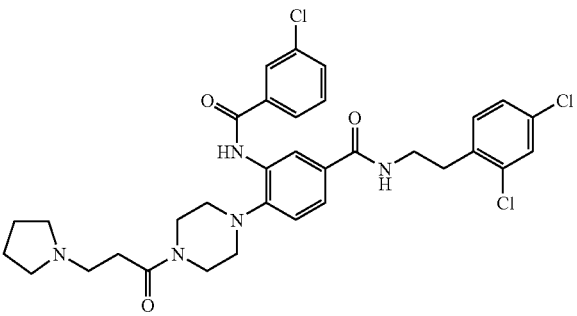

Prepared exactly as compound in Example 62 on 300 mg of preloaded resin, with modification of freshly (via Michael addition) prepared crude 3-pyrrolidino-propionic acid being used instead of N,N-dimethyl β alanine. Cleaved compound is purified using Waters mass-triggered-LCMS purification system and procedure outlined in the General procedures section. MW=655.19 Da (calc. monoisotopic for $C_{33}H_{36}Cl_3N_5O_3$), measured $(M+H)^+$=656.2 Da with appropriate Cl-isotope pattern, UV {220} based purity 96.9%.

EXAMPLE 65

3-(3-Chloro-benzoylamino)-N-[2-(2,4-dichloro-phenyl)-ethyl]-4-{4-[3-(3,3,4,4-tetrafluoro-pyrrolidin-1-yl)-propionyl]-piperazin-1-yl}-benzamide

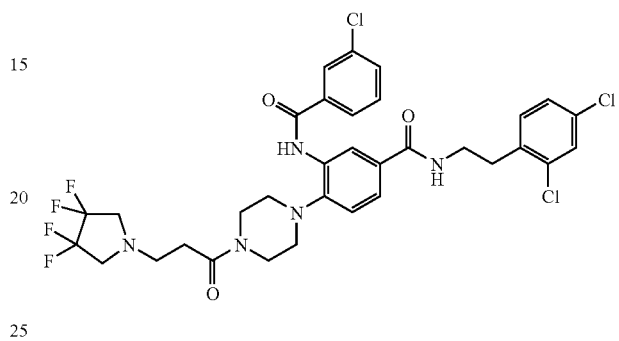

Prepared exactly as compound in Example 66 on 300 mg of preloaded resin, with modification of freshly (via Michael addition) prepared crude 3-(3',3',4',4'-tetrafluoropyrrolidino)-propionic acid being used instead of N,N-dimethyl beta-Alanine. Cleaved compound is purified using Waters mass-triggered-LCMS purification system and procedure outlined in the General procedures section. MW=727.15 Da (calc. monoisotopic for $C_{33}H_{32}Cl_3F_4N_5O_3$), measured $(M+H)^+$=728.2 Da with appropriate Cl-isotope pattern, UV {220} based purity 100%.

EXAMPLE 66

4-[4-(3-Aziridin-1-yl-propionyl)-piperazin-1-yl]-3-(3-chloro-benzoylamino)-N-[2-(2,4-dichloro-phenyl)-ethyl]-benzamide

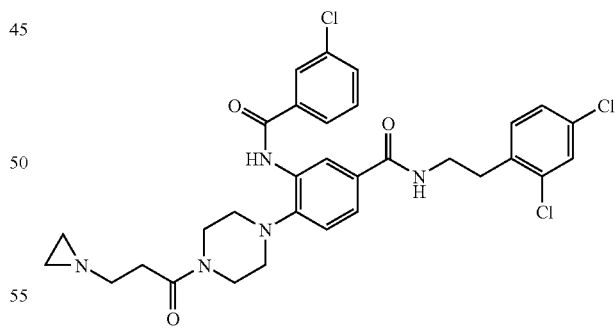

Prepared exactly as compound in Example 66 on 300 mg of preloaded resin, with modification of freshly (via Michael addition) prepared crude 3-aziridino-propionic acid being used instead of N,N-dimethyl β-alanine. Cleaved compound is purified using Waters mass-triggered-LCMS purification system and procedure outlined in the General procedures section. MW=627.16 Da (calc. monoisotopic for $C_{31}H_{32}Cl_3N_5O_3$), measured $(M+H)^+$=628.2 Da with appropriate Cl-isotope pattern, UV {220} based purity 19.1%.

EXAMPLE 67

3-(3-Chloro-benzoylamino)-N-[2-(2,4-dichloro-phenyl)-ethyl]-4-[4-(3-methylamino-propionyl)-piperazin-1-yl]-benzamide

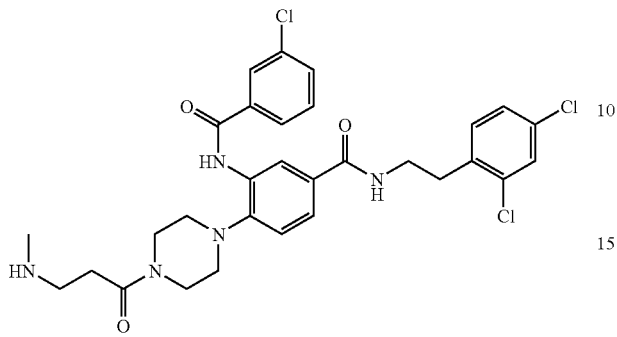

Prepared exactly as compound in Example 62 on 300 mg of preloaded resin, with modification of N-methyl-Fmoc β alanine being used instead of N,N-dimethyl β alanine. Cleaved compound is first Fmoc deprotected via 30 min ambient temperature treatment of product with 3 ml piperidine/DMF (1:1) and then purified using Waters mass-triggered-LCMS purification system and procedure outlined in the General procedures section. MW=615.16 Da (calc. monoisotopic for $C_{30}H_{32}Cl_3N_5O_3$), measured $(M+H)^+$=616.3 Da with appropriate Cl-isotope pattern.

EXAMPLE 68

3-(3-Chloro-benzoylamino)-4-[4-(2-dimethylamino-ethyl)-piperazin-1-yl]-N-methyl-N-phenethyl-benzamide

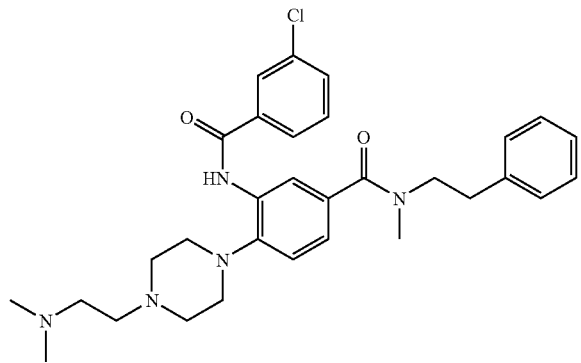

Step 2: 1288 mg (4 mmol) of intermediate 1 is dissolved in 10 ml of DMF, together with 504 mg (4 mmol) of DIC and 1836 mg (=12 mmol) of HOBt and 810 mg (6 mmol) of N-methyl-phenethyl amine in 4 ml DMF. After 2 h at ambient temperature ⅔ of solvent is evaporated, and oily residue is purified using RP-HPLC Beckman system and procedure outlined in the General procedures section. Proper fractions are lyophilized to yield of 450 mg of desired material.

Step 3: 400 mg of the product from the previous reaction is dissolved in 40 mL of methanol and 250 mg of 10% Pd/C added. After evacuation in a Parr apparatus, 30 psi of hydrogen introduced. The reaction mixture is shaken 3 h at ambient temperature. Analytical LCMS shows product. The catalyst is filtered off over pad of silica and methanol evaporated on ROTAVAP. The product used for next reaction without purification.

Standard HATU mediated coupling where 110 mg (0.25 mmol) of starting material, 1 mmol (380 mg) of HATU, 1 mmol (156 mg) of 3-chloro benzoic acid, and 3 mmol (390 mg=440 μL) of DIEA at ambient temperature is reacted for 3 h. LCMS check shows desired product, which is isolated after partial evaporation via Waters mass-triggered-LCMS purification system. Lyophilization yields desired product. MW=547.23 Da (talc. monoisotopic for $C_{31}H_{38}ClN_5O_2$), measured $(M+H)^+$=548.3 Da with appropriate Cl-isotope pattern, UV {220} based purity 98%.

EXAMPLE 69

4-{2-(3-Chloro-benzoylamino)-4-[2-(2,4-dichloro-phenyl)-ethylcarbamoyl]-phenyl}-piperazine-1-carboxylic acid ethylamide

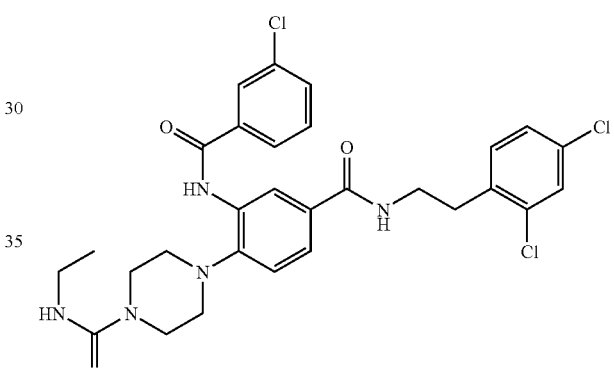

200 mg of preloaded resin I (after step 1, 2 and 3) is converted to final product as follows:

Step 4: Resin in syringe is treated with 149 mg of ethyl isocyanate in DMF for 2 hours at 50° C. Washed 3×DMF, 3×DCM, 3×DMF—end up swollen in DMF.

Step 4: The nitro group is reduced via treatment of resin with 1M solution of $SnCl_2$ as in example 12 in DMF at ambient temperature for 12 h. The resin is washed 3×DMF, 2×DCM, 2×DMF, (ending up with swollen resin in DMF).

Step 5: To the resin, is added a solution of 312 mg (2 mmol) 3-chloro benzoic acid, 2 mmol (760 mg) of HATU, and 6 mmol (770 mg=840 μL) of DIEA in 7 mL of DMF. This coupling is done at ambient temperature (RT) for 12 h. The resin is washed 3×DMF, 2×DCM, 2×THF and dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=601.14

EXAMPLE 70

N-{5-[2-(2,4-Dichloro-phenyl)-ethylcarbamoyl]-2-[4-(3-dimethylamino-propionyl)-piperazin-1-yl]-phenyl}-isophthalamic acid

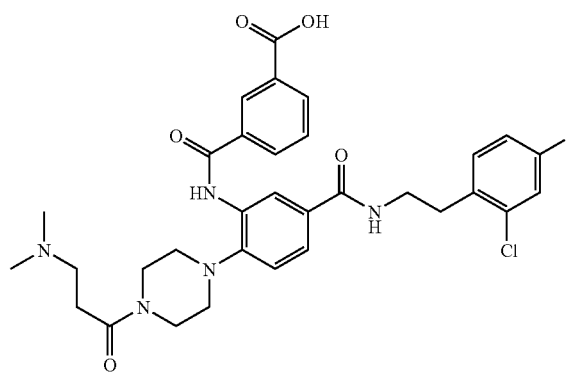

200 mg of preloaded resin I (after step 1, 2 and 3) is converted to final product as follows:

Step 4: HATU coupling of N,N-dimethyl-β alanine is achieved via reaction of 2 mmol of the N,N-dimethyl-β alanine, 2 mmol HATU, 6 mmol of DIEA in 6 ml DMF at ambient temperature for 12 h. the resin is washed 3×DMF, 3×DCM, 3×DMF—end up swollen in DMF.

Step 5: The nitro group is reduced via treatment of resin with 1M solution of $SnCl_2$ as in example 12 in DMF at ambient temperature for 12 h. The resin is washed 3×DMF, 2×DCM, 2×DMF, (ending up with swollen resin in DMF).

Step 6: Resin in syringe is treated with freshly prepared sym-anhydride of isophthalic acid (prepared by mixing of 2 mmol of amino acid with 1 mmol of DIC, 5 min) in DMF for 12 hours at ambient temperature. The resin is washed 3×DMF, 3×DCM, 3×THF—then dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=639.2 Da (calc. monoisotopic for $C_{32}H_{35}Cl_2N_5O_5$), measured $(M+H)^+$=640.2 Da with appropriate Cl-isotope pattern UV {220} based purity 94.9%.

EXAMPLE 71

N-{5-[2-(2,4-Dichloro-phenyl)-ethylcarbamoyl]-2-[4-(3-dimethylamino-propionyl)-piperazin-1-yl]-phenyl}-terephthalamic acid

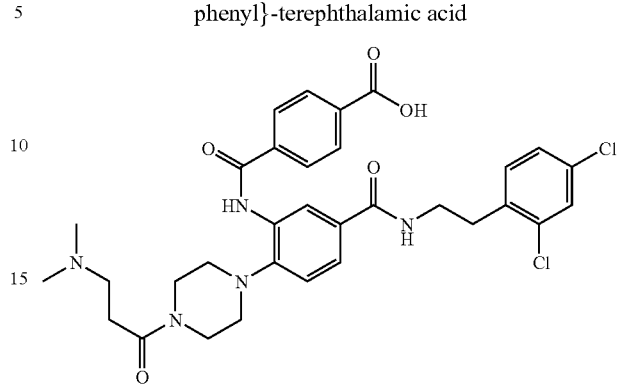

200 mg of preloaded resin I (after step 1, 2 and 3) is converted to final product as follows:

Step 4: HATU coupling of N,N-dimethyl-beta Alanine is achieved via reaction of 2 mmol of the N,N-dimethyl-β alanine, 2 mmol HATU, 6 mmol of DIEA in 6 ml DMF at ambient temperature for 12 h. The resin is washed 3×DMF, 3×DCM, 3×DMF—end up swollen in DMF.

Step 5: The nitro group is reduced via treatment of resin with 1M solution of $SnCl_2$ as in example 12 in DMF at ambient temperature for 12 h. The resin is washed 3×DMF, 2×DCM, 2×DMF, (ending up with swollen resin in DMF).

Step 6: Resin in syringe is treated with freshly prepared sym-anhydride of terephthalic acid (prepared by mixing of 2 mmol of amino acid with 1 mmol of DIC, 5 min) in DMF for 12 hours at ambient temperature. Washed 3×DMF, 3×DCM, 3×THF—then dried in vacuum.

For cleavage, 6 ml of mixture TFA/water 95:5 are added to the dry resin and shaken at room temperature for 4 h. The resin is filtered off, washed with mixture TFA/water and the combined extracts are evaporated in vacuum. The crude product is dissolved in AN/water mixture and lyophilized. The pure title compound is isolated after HPLC purification using Waters mass-triggered-LCMS purification system and procedure outlined in the General procedures section. MW=639.2 Da (calc. monoisotopic for $C_{32}H_{35}Cl_2N_5O_5$), measured $(M+H)^+$=640.2 Da with appropriate Cl-isotope pattern UV {220} based purity 94.2%.

Pharmacology

Compounds according to the invention as described herein as being useful for being able to modulate signaling through CxCR3, and thus, are also useful for treating disorders or processes depending upon CxCR3 function.

Accordingly, an invention herein is directed to a method of treating affected patients comprising contacting an efficaceous amount of a compound of formula with a composition comprising the present invention.

Furthermore, another invention herein is described to a method of treating a patient suffering from or subject to an inflammatory condition comprising administering to the patient a pharmaceutically effective amount of compound of formula 1. References herein to treating an should be understood to include prophylactic therapy to prevent or inhibit the as well as the treatment of an established acute or chronic or physiological conditions associated with to essentially cure the patient of the, inhibit the degree (amount) of or ameliorate

---

Da (calc. monoisotopic for $C_{29}H_{30}Cl_3N_5O_3$), measured $(M+H)^+$=602.1 Da with appropriate Cl-isotope pattern, UV (220) based purity 95.4%.

the physiological conditions associated therewith. "Effective amount" is meant to describe an amount of the compound of the present invention effective within the scope of reasonable biological judgment, suitable for use in contact with the cells of humans and other mammals without undue toxicity, irritation, allergic response and the like, and are commensurate with a reasonable benefit/risk ratio in treating an and thus producing the desired therapeutic effect.

Physiological conditions discussed herein include some, but not all, of the possible clinical situations where an anti-treatment is warranted. Those experienced in this field are well aware of the circumstances requiring treatment.

A particular aspect of the invention provides for a compound according to the invention to be administered in the form of a pharmaceutical composition, though the compound may be administered alone. "Pharmaceutical composition" means a composition comprising a compound of formula 1 and at least one component selected from the group comprising pharmaceutically acceptable carriers, diluents, coatings, adjuvants, excipients, or vehicles, such as preserving agents, fillers, disintegrating agents, wetting agents, emulsifying agents, emulsion stabilizing agents, suspending agents, isotonic agents, sweetening agents, flavoring agents, perfuming agents, coloring agents, antibacterial agents, antifungal agents, other therapeutic agents, lubricating agents, adsorption delaying or promoting agents, and dispensing agents, depending on the nature of the mode of administration and dosage, forms. The compositions may be presented in the form of tablets, pills, granules, powders, aqueous solutions or suspensions, injectable solutions, elixirs or syrups. Exemplary suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Exemplary antibacterial and antifungal agents for the prevention of the action of microorganisms include parabens, chlorobutanol, phenol, sorbic acid, and the like. Exemplary isotonic agents include sugars, sodium chloride and the like. Exemplary adsorption delaying agents to prolong absorption include aluminum monostearate and gelatin. Exemplary adsorption promoting agents to enhance absorption include dimethyl sulfoxide and related analogs. Exemplary carriers, diluents, solvents, vehicles, solubilizing agents, emulsifiers and emulsion stabilizers, include water, chloroform, sucrose, ethanol, isopropyl alcohol, ethyl carbonate, ethyl acetate, benzyl alcohol, tetrahydrofurfuryl alcohol, benzyl benzoate, polyols, propylene glycol, 1,3-butylene glycol, glycerol, polyethylene glycols, dimethylformamide, Tween® 60, Span® 60, cetostearyl alcohol, myristyl alcohol, glyceryl mono-stearate and sodium lauryl sulfate, fatty acid esters of sorbitan, vegetable oils (such as cottonseed oil, groundnut oil, corn germ oil, olive oil, castor oil and sesame oil) and injectable organic esters such as ethyl oleate, and the like, or suitable mixtures of these substances. Exemplary excipients include lactose, milk sugar, sodium citrate, calcium carbonate, dicalcium phosphate. Exemplary disintegrating agents include starch, alginic acids and certain complex silicates. Exemplary lubricants include magnesium stearate, sodium lauryl sulfate, talc, as well as high molecular weight polyethylene glycols.

Other therapeutic agents may be used in combination with a compound of the present invention, including other anti agents. Therapeutic agents used in combination with a compound of the present invention may be administered separately, simultaneously or sequentially. The choice of material in the pharmaceutical composition other than the compound of formula 1 is generally determined in accordance with the chemical properties of the active compound such as solubility, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets.

The pharmaceutical compositions may be presented in assorted forms such as tablets, pills, granules, powders, aqueous solutions or suspensions, injectable solutions, elixirs or syrups.

"Liquid dosage form" means the dose of the active compound to be administered to the patient is in liquid form, for, example, pharmaceutically acceptable emulsions, solutions, suspensions, syrups and elixirs. In addition to the active compounds, the liquid dosage forms may contain inert diluents commonly used in the art, such solvents, solubilizing agents and emulsifiers.

Solid compositions may also be employed as fillers in soft and hard-filled gelatin capsules using such excipients as lactose or milk sugar as well as high molecular weight polyethylene glycols, and the like.

When aqueous suspensions are used they can contain emulsifying agents or agents which facilitate suspension.

The oily phase of the emulsion pharmaceutical composition may be constituted from known ingredients in a known manner. While the phase may comprise merely an emulsifier (otherwise known as an emulgent), it desirably comprises a mixture of at least one emulsifier with a fat or an oil or with both a fat and an oil. In a particular embodiment, a hydrophilic emulsifier is included together with a lipophilic emulsifier that acts as a stabilizer. Together, the emulsifier(s) with or without stabilizer(s) make up the emulsifying wax, and the way together with the oil and fat make up the emulsifying ointment base which forms the oily dispersed phase of the cream formulations.

If desired, the aqueous phase of the cream base may include, for example, a least 30% w/w of a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound that enhances absorption or penetration of the active ingredient through the skin or other affected areas.

The choice of suitable oils or fats for a formulation is based on achieving the desired properties. Thus the cream should preferably be a non-greasy, non-staining and washable product with suitable consistency to avoid leakage from tubes or other containers. Straight or branched chain, mono- or dibasic alkyl esters such as di-isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils can be used.

In practice, a compound/pharmaceutical compositions of the present invention may be administered in a suitable formulation to humans and animals by topical or systemic administration, including oral, inhalational, rectal, nasal, buccal, sublingual, vaginal, colonic, parenteral (including subcutaneous, intramuscular, intravenous, intradermal, intrathecal and epidural), intracisternal and intraperitoneal. It will be appreciated that the preferred route may vary with for example the condition of the recipient.

"Pharmaceutically acceptable dosage forms" refers to dosage forms of the compound of the invention, and includes, for example, tablets, dragées, powders, elixirs, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in Remington's Pharmaceutical Sciences, Mack Publishing Co., Easton, Pa., latest edition.

"Formulations suitable for oral administration" may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tables may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compounds moistened with an inert liquid diluent. The tablets may optionally be coated or scored and may be formulated so as to provide slow or controlled release of the active ingredient therein.

Solid compositions for rectal administration include suppositories formulated in accordance with known methods and containing at least one compound of the invention.

If desired, and for more effective distribution, the compounds can be microencapsulated in, or attached to, a slow release or targeted delivery systems such as a biocompatible, biodegradable polymer matrices (e.g., poly(d,l-lactide co-glycolide)), liposomes, and microspheres and subcutaneously or intramuscularly injected by a technique called subcutaneous or intramuscular depot to provide continuous slow release of the compound(s) for a period of 2 weeks or longer. The compounds may be sterilized, for example, by filtration through a bacteria retaining filter, or by incorporating sterilizing agents in the form of sterile solid compositions which can be dissolved in sterile water, or some other sterile injectable medium immediately before use.

"Formulations suitable for nasal or inhalational administration" means formulations which are in a form suitable to be administered nasally or by inhalation to a patient. The formulation may contain a carrier, in a powder form, having a particle size for example in the range 1 to 500 microns (including particle sizes in a range between 20 and 500 microns in increments of 5 microns such as 30 microns, 35 microns, etc.). Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents. Inhalational therapy is readily administered by metered dose inhalers.

"Formulations suitable for oral administration" means formulations which are in a form suitable to be administered orally to a patient. The formulations may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

"Formulations suitable for parenteral administration" means formulations that are in a form suitable to be administered parenterally to a patient. The formulations are sterile and include emulsions, suspensions, aqueous and non-aqueous injection solutions, which may contain suspending agents and thickening agents and anti-oxidants, buffers, bacteriostats and solutes which render the formulation isotonic, and have a suitably adjusted pH, with the blood of the intended recipient.

"Formulations suitable for rectal or vaginal administrations" means formulations that are in a form suitable to be administered rectally or vaginally to a patient. Suppositories are a particular form for such formulations that can be prepared by mixing the compounds of this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

"Formulations suitable for systemic administration" means formulations that are in a form 20 suitable to be administered systemically to a patient. The formulation is preferably administered by injection, including transmuscular, intravenous, intraperitoneal, and subcutaneous. For injection, the compounds of the invention are formulated in liquid solutions, in particular in physiologically compatible buffers such as Hank's solution or Ringer's solution. In addition, the compounds may be formulated in solid form and redissolved or suspended immediately prior to use. Lyophilized forms are also included. Systematic administration also can be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucosal administration. In addition, detergents may be used to facilitate permeation. Transmucosal administration may be through use of nasal sprays, for example, or suppositories. For oral administration, the compounds are formulated into conventional oral administration forms such as capsules, tablets, and tonics.

"Formulations suitable for topical administration" means formulations that are in a form suitable to be administered topically to a patient. The formulation may be presented as a topical ointment, salves, powders, sprays and inhalants, gels (water or alcohol based), creams, as is generally known in the art, or incorporated into a matrix base for application in a patch, which would allow a controlled release of compound through the transdermal barrier. When formulated in an ointment, the active ingredients may be employed with either a paraffinic or a water-miscible ointment base. Alternatively, the active ingredients may be formulated in a cream with an oil-in-water cream base. Formulations suitable for topical administration in the eye include eye drops wherein the active ingredient is dissolved or suspended in a suitable carrier, especially an aqueous solvent for the active ingredient. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

"Solid dosage form" means the dosage form of the compound of the invention is solid form, for example capsules, tablets, pills, powders, dragées or granules. In such solid dosage forms, the compound of the invention is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, (i) lubricants, as for example, talc, calcium stearate, magnesium stearate, solid polyethylene glycols, sodium lauryl sulfate, (j) opacifying agents, (k) buffering agents, and agents which release the compound(s) of the invention in a certain part of the intestinal tract in a delayed manner.

Actual dosage levels of active ingredient(s) in the compositions of the invention may be varied so as to obtain an amount of active ingredient(s) that is (are) effective to obtain a desired therapeutic response for a particular composition and method of administration for a patient. A selected dosage level for any particular patient therefore depends upon a variety of factors including the desired therapeutic effect, on the route of administration, on the desired duration of treatment, the etiology and severity of the disease, the patient's condition, weight, sex, diet and age, the type and potency of each active ingredient, rates of absorption, metabolism and/or excretion and other factors.

Total daily dose of the compounds of this invention administered to a patient in single or divided doses may be in amounts, for example, of from about 0.001 to about 100 mg/kg body weight daily and preferably 0.01 to 10 mg/kg/day. For example, in an adult, the doses are generally from about 0.001 to about 100, preferably about 0.01 to about 10 mg/kg body weight per day by inhalation, from about 0.01 to about 100, preferably 0.1 to 70, more especially 0.5 to 10, mg/kg body weight per day by oral administration, and from about 0.01 to about 50, preferably 0.01 to 10, mg/kg body weight per day by intravenous administration. The percentage of active ingredient in a composition may be varied, though it should constitute a proportion such that a suitable dosage shall be obtained. Dosage unit compositions may contain such amounts of such submultiples thereof as may be used to make up the daily dose. Obviously, several unit dosage forms may be administered at about the same time. A dosage may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. It goes without saying that, for other patients, it will be necessary to prescribe not more than one or two doses per day.

The formulations can be prepared in unit dosage form by any of the methods well known in the art of pharmacy. Such methods include the step of bringing into association the active ingredient with the carrier that constitutes one or more accessory ingredients. In general the formulations are prepared by uniformly and intimately bringing into association the active ingredient with liquid carriers or finely divided solid carriers or both, and then, if necessary, shaping the product.

The formulations may be presented in unit-dose or multi-dose containers, for example sealed ampoules and vials with elastomeric stoppers, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Compounds within the scope of the present invention exhibit marked pharmacological activities according to tests described in the literature and below, which tests results are believed to correlate to pharmacological activity in humans and other mammals.

The chemical reactions described in the references cited above are generally disclosed in terms of their broadest application to the preparation of the compounds of this invention. Occasionally, the reactions may not be applicable as described to each compound included within the scope of compounds disclosed herein. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional will be applicable to the preparation of the corresponding compounds of this invention. In all preparative methods, all starting materials are known or readily prep arable from known starting materials.

The regimen for treating a patient suffering from an appropriate disease with the compounds and/or compositions of the present invention is selected in accordance with a variety of factors, including the age, weight, sex, diet, and medical condition of the patient, the severity of the infection, the route of administration, pharmacological considerations such as the activity, efficacy, pharmacokinetic, and toxicology profiles of the particular compounds employed, and whether a drug delivery system is utilized. Administration of the drug combinations disclosed herein should generally be continued over a period until acceptable, indicating that has been controlled or eradicated. Patients undergoing treatment with the drug combinations disclosed herein can be routinely monitored by measuring appropriate clinical indices to determine the effectiveness of therapy. Such metrics include, for example, FEV1 for monitoring pulmonary function in patients with COPD, range of motion for evaluating patients with arthritis, and thermal scans to quantify calor in diverse inflammatory conditions. Measurement of tissue swelling and appearance (tumor and rubor) are also useful metrics in daily clinical practice. Continuous analysis of the data obtained by these methods permits modification of the treatment regimen during therapy so that optimal amounts of each component in the combination are administered, and so that the duration of treatment can be determined as well. Thus, the treatment regimen/dosing schedule can be rationally modified over the course of therapy so that the lowest amounts of each of the compounds used in combination which together exhibit satisfactory effectiveness are administered, and so that administration of such compounds in combination is continued only so long as is necessary to successfully treat the patient.

The present invention encompasses the use of combinations of other types of compounds and compounds having CxCR3 activity as described above to treat or prevent disease where one or more of these compounds is present in a pharmaceutically effective amount, and the other(s) is(are) present in a subclinical pharmaceutically effective or nominally effective amount(s) owing to their additive or synergistic effects. As used herein, the term "additive effect" describes the combined effect of two (or more) pharmaceutically active agents that is equal to the sum of the effect of each agent given alone. A synergistic effect is one in which the combined effect of two (or more) pharmaceutically active agents is greater than the sum of the effect of each agent given alone. Various compounds can be expected to benefit patients when administered in a combination, and these possibilities depend upon the particular disease to be treated. These include nonsteroidal anti-inflammatories such as acetyl salicylic acid and its cogeners, 2-aryl propionic acid derivatives such as ibuprofen. Pain relievers may be combined such as acetaminophen, opiates and their analogs. The management of some diseases may benefit from combination with steroids such as prednisone or other glucocorticoids or cogeners. Various protein therapeutics also could be combined with the present invention, and these include cytokine-directed antibodies such as Enbrel®. Finally, some compounds that could be combined in the management of respiratory disease include beta-2 adrenergic agonists like albuterol and its cogeners, and xanthines such as theophylline and related analogs. For the presently described CxCR3-directed compounds, numerous other drug agents can be imagined that may provided added benefit when administered in a combination.

Combination therapy employing other drugs with compounds of the present invention possesses several major advantages over single drug therapy. First, by making treatment possible with lower doses of the individual drugs than would be possible if used alone, one would expect a reduction in toxicity and side effects associated with treatment. A second major benefit of combination therapy is that because the two drugs act independently, there is less chance of development of desensitization that may limit responsiveness to treatment. A third benefit of combination therapy may be reduced cost, due to the need for lower amounts of therapeutic agents required for effective treatment. Finally, a fourth benefit is better management of disease, since clinical efficacy for some patients may depend upon a combination of suitable compounds acting in different ways.

Bioactivity Measured

CxCR3 A Bioassay Method

The bioactivity of compounds is tested in a fluorometric imaging plate reader (FLIPR; Molecular Devices) using engineered CHO cells expressing the human CxCR3A coupled to a chimeric G protein (Gαi4qi4). Cells are plated the day prior to bioassay in F12 medium supplemented with 10% FBS and 0.3 mg/ml hygromycin antibiotic to maintain recombinant selection. The day of bioassay, cells are washed and dye loaded for one hour with Fluo-4-AM (Invitrogen) in Hanks Balanced Salt Solution (Gibco), buffered with 25 mM Hepes at pH 7.4 and containing 0.36 mg/ml probenicid. This buffer, but lacking the dye (aka standard buffer), also is used for making serial dilutions of test compounds. Cells are washed free of excess dye (leaving them in 25 μl of buffer), and 5 μl of each compound dilution are transferred from the source plate to the cell plate on a Beckman FX. In the FLIPR instrument, following basal readings, 20 μl of 46 nM IP10 (from R&D Systems) is added using the standard buffer supplemented with 0.1% BSA. Fluorometric images are read for a total of two minutes. Data are exported taking the maximal FLIPR value/sample and processed using XLfit to calculate $IC_{50}$s. The compounds within the scope of the present invention have activities in the above FLIPR assay of less than 25 micromolar, more particularly less than 1 micromolar, and further particularly less than 200 nanomolar $IC_{50}$.

The present invention may be embodied in other specific forms without departing from the spirit or essential attributes thereof.

What is claimed is:

1. A compound selected from the group consisting of the following formulae:

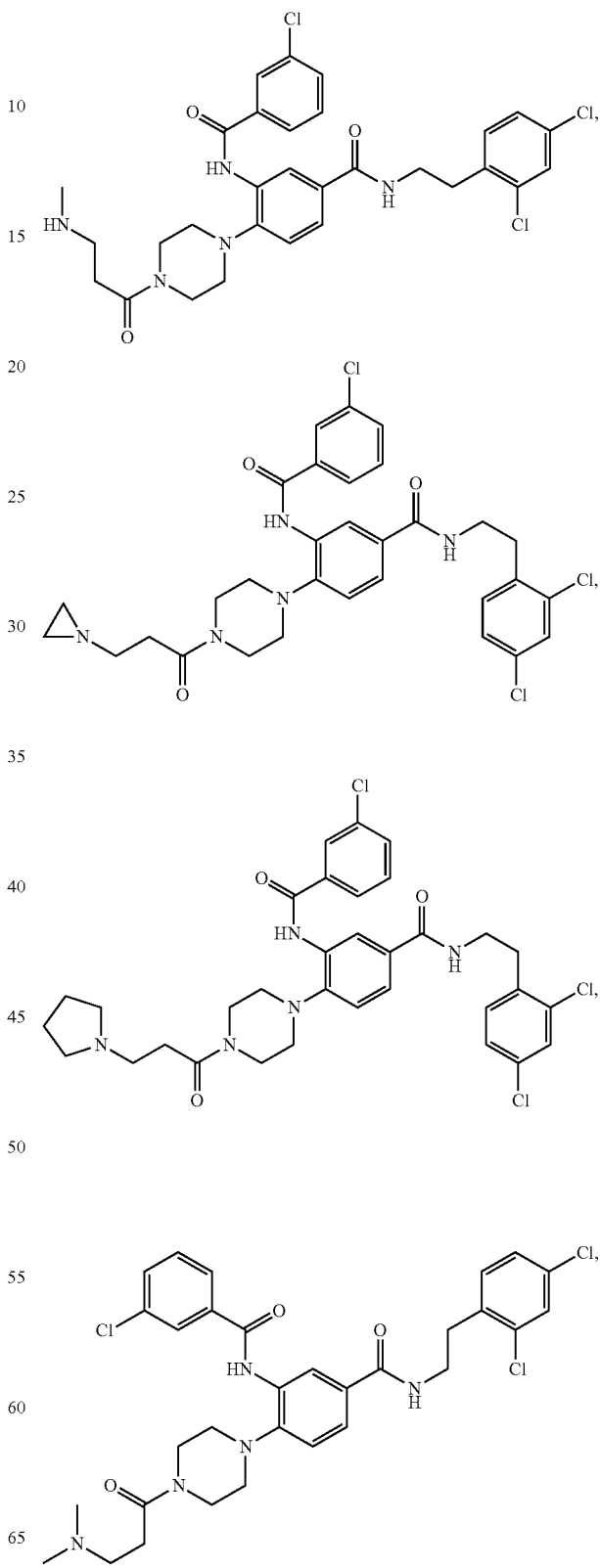

87
-continued
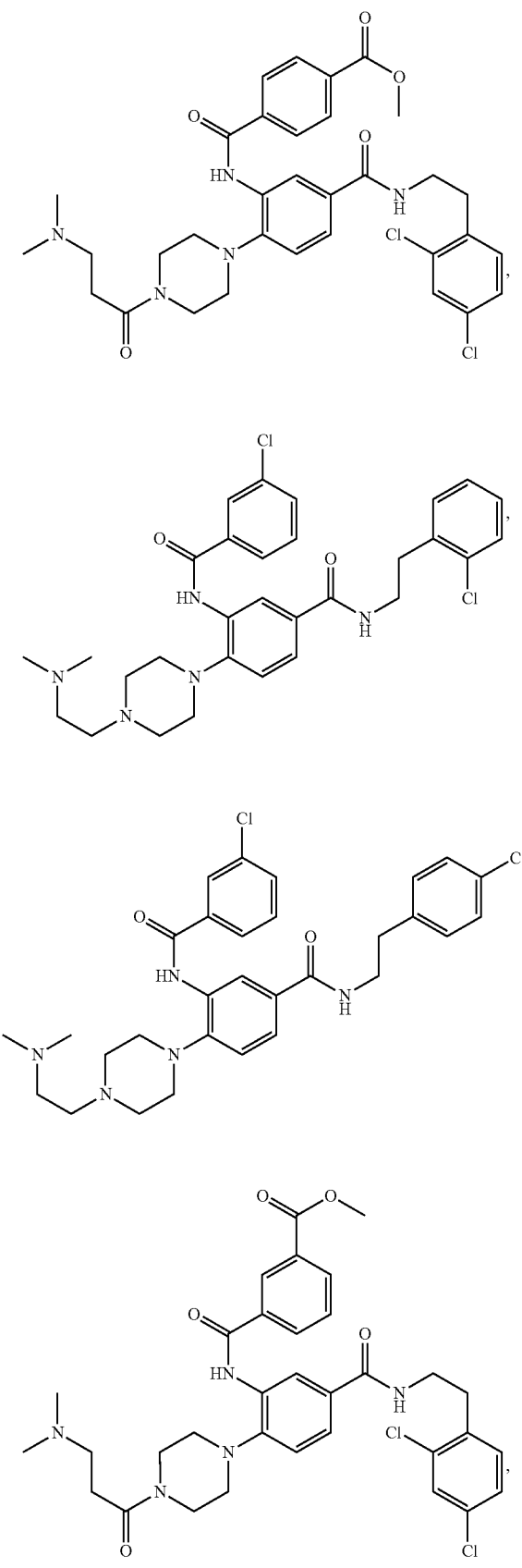
88
-continued
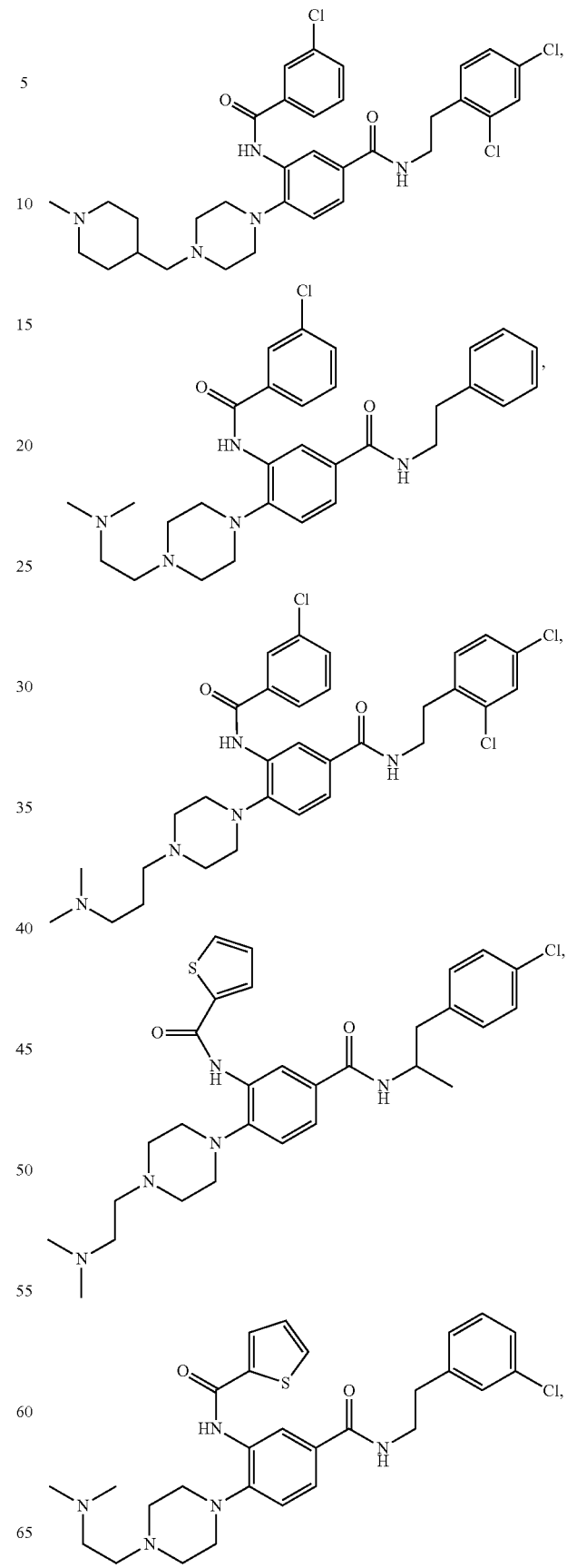

89
-continued
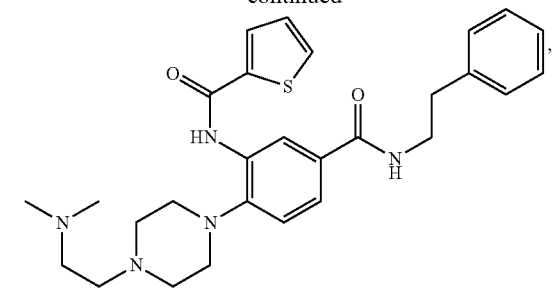
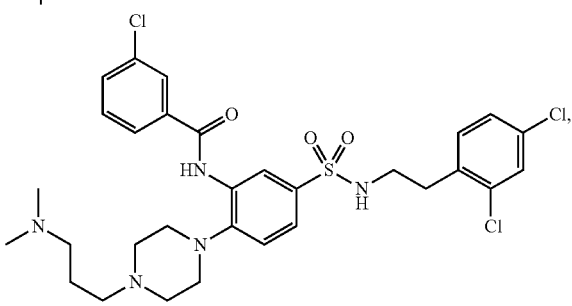
90
-continued
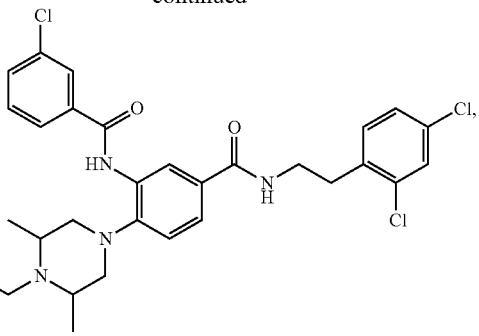
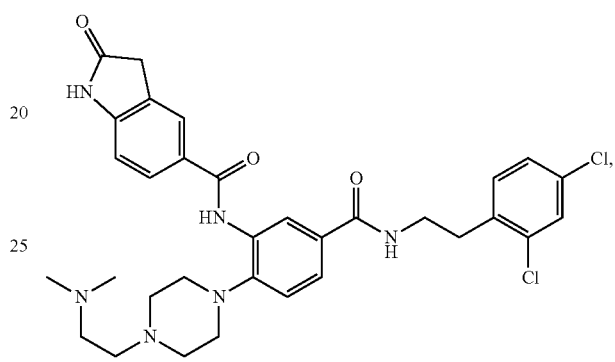
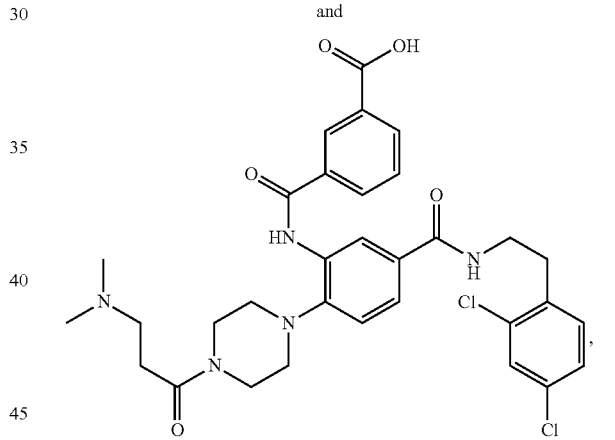
and
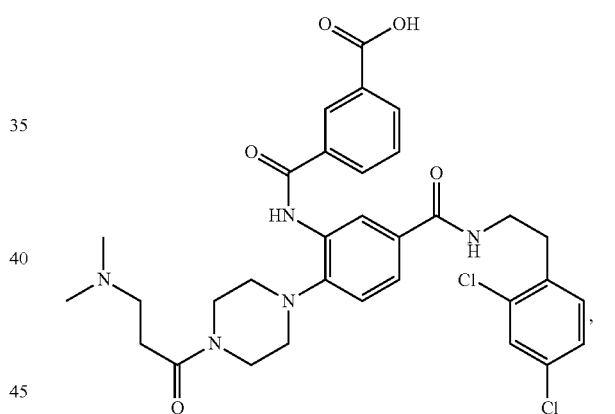
or a pharmaceutically acceptable salt, N-oxide or any combination thereof.
2. A pharmaceutical composition comprising a pharmaceutically acceptable amount of a compound according to claim 1, and a pharmaceutically acceptable additive.
* * * * *